(12) United States Patent
Heaton et al.

(10) Patent No.: US 9,701,655 B2
(45) Date of Patent: Jul. 11, 2017

(54) FUNCTIONALISED BENZOPYRAN COMPOUNDS AND USE THEREOF

(71) Applicant: NOVOGEN LIMITED, Hornsby, New South Wales (AU)

(72) Inventors: Andrew Heaton, Ithaca, NY (US); David Brown, North Ryde (AU); Graham Kelly, Wahroonga (AU)

(73) Assignee: NOVOGEN LIMITED, Hornsby (AU)

( * ) Notice: Subject to any disclaimer, the term of this patent is extended or adjusted under 35 U.S.C. 154(b) by 0 days.

(21) Appl. No.: 14/771,440

(22) PCT Filed: Feb. 5, 2015

(86) PCT No.: PCT/AU2015/050040
§ 371 (c)(1),
(2) Date: Aug. 28, 2015

(87) PCT Pub. No.: WO2015/117202
PCT Pub. Date: Aug. 13, 2015

(65) Prior Publication Data
US 2016/0340329 A1    Nov. 24, 2016

Related U.S. Application Data

(60) Provisional application No. 61/937,368, filed on Feb. 7, 2014, provisional application No. 61/987,323, filed on May 1, 2014.

(51) Int. Cl.
| | | |
|---|---|---|
| *A61K 31/352* | (2006.01) | |
| *C07D 311/04* | (2006.01) | |
| *C07D 311/58* | (2006.01) | |
| *C07D 407/04* | (2006.01) | |
| *C07D 407/10* | (2006.01) | |

(52) U.S. Cl.
CPC .......... *C07D 311/58* (2013.01); *C07D 407/04* (2013.01); *C07D 407/10* (2013.01)

(58) Field of Classification Search
CPC ............................ A61K 31/352; C07D 311/04
USPC .......................................... 514/456; 549/406
See application file for complete search history.

(56) References Cited

U.S. PATENT DOCUMENTS

| | | | |
|---|---|---|---|
| 3,340,276 A | 9/1967 | Carney et al. | |
| 3,822,287 A | 7/1974 | Bolger et al. | |
| 4,447,622 A | 5/1984 | Salman et al. | |
| 5,280,040 A | 1/1994 | Labroo et al. | |
| 5,451,603 A | 9/1995 | Piggott | |
| 5,464,862 A | 11/1995 | Labroo et al. | |
| 5,480,903 A | 1/1996 | Piggott | |
| 5,696,149 A | 12/1997 | Korsgaard et al. | |
| 5,726,202 A | 3/1998 | Shalmi et al. | |
| 5,747,059 A | 5/1998 | Korsgaard et al. | |
| 5,756,539 A | 5/1998 | Skrumsager et al. | |
| 5,780,502 A | 7/1998 | Guldhammer | |
| 5,827,873 A | 10/1998 | Korsgaard et al. | |
| 5,883,118 A | 3/1999 | Shalmi et al. | |
| 5,886,021 A | 3/1999 | Korsgaard et al. | |
| 5,919,812 A | 7/1999 | Korsgaard et al. | |
| 5,919,817 A | 7/1999 | Jacobsen et al. | |
| 5,925,771 A | 7/1999 | Treppendahl | |
| 6,008,242 A | 12/1999 | Korsgaard et al. | |
| 6,043,269 A | 3/2000 | Jacobsen et al. | |
| 6,184,005 B1 | 2/2001 | Lehmann | |
| 7,226,945 B2 | 6/2007 | Barlaam et al. | |
| 7,528,267 B2 | 5/2009 | Setchell et al. | |
| 7,601,855 B2 | 10/2009 | Heaton et al. | |
| 7,960,573 B2 | 6/2011 | Setchell et al. | |
| 8,080,675 B2 | 12/2011 | Heaton et al. | |
| 8,084,628 B2 | 12/2011 | Heaton et al. | |
| 8,163,795 B2 | 4/2012 | Heaton et al. | |
| 8,461,361 B2 | 6/2013 | Heaton et al. | |
| 8,697,891 B2 | 4/2014 | Heaton et al. | |
| 2004/0039015 A1 | 2/2004 | Barlaam et al. | |
| 2004/0167165 A1 | 8/2004 | Shankar et al. | |
| 2005/0043350 A9 | 2/2005 | Barlaam et al. | |
| 2005/0119301 A1 | 6/2005 | Husband et al. | |
| 2006/0074126 A1 | 4/2006 | Heaton et al. | |
| 2006/0074127 A1 | 4/2006 | Heaton et al. | |
| 2006/0141591 A1 | 6/2006 | Kyuuko et al. | |
| 2007/0027329 A1 | 2/2007 | Setchell et al. | |
| 2009/0221564 A1 | 9/2009 | Wang et al. | |
| 2009/0317490 A1 | 12/2009 | Heaton et al. | |
| 2010/0069653 A1 | 3/2010 | Setchell et al. | |
| 2010/0130598 A1 | 5/2010 | Brown et al. | |
| 2010/0152284 A1 | 6/2010 | Brown et al. | |
| 2011/0251246 A1 | 10/2011 | Kufe et al. | |
| 2012/0004296 A1 | 1/2012 | Heaton et al. | |
| 2012/0039917 A1 | 2/2012 | Husband et al. | |
| 2012/0114766 A1 | 5/2012 | Heaton et al. | |
| 2012/0172424 A1 | 7/2012 | Heaton et al. | |
| 2012/0251630 A1 | 10/2012 | Alvero et al. | |
| 2013/0137694 A1 | 5/2013 | Batist et al. | |
| 2013/0273177 A1 | 10/2013 | Moreno | |
| 2014/0161908 A1 | 6/2014 | Heaton et al. | |
| 2014/0170243 A1 | 6/2014 | Heaton et al. | |

FOREIGN PATENT DOCUMENTS

| | | |
|---|---|---|
| AU | 2008230055 | 6/2010 |
| BE | 891562 | 4/1982 |
| CN | 1207038 | 2/1999 |
| CN | 101210012 | 7/2008 |
| CN | 102603692 | 7/2012 |
| CN | 103408528 | 11/2013 |
| CN | 103450142 | 12/2013 |
| CN | 103585145 | 2/2014 |
| CN | 103638008 | 3/2014 |

(Continued)

*Primary Examiner* — Charanjit Aulakh
(74) *Attorney, Agent, or Firm* — K&L Gates LLP

(57) ABSTRACT

The present invention relates broadly to anti-cancer agents. In particular, the present invention relates to selected benzopyran compounds, the preparation thereof, and their use in methods for treating cancer and reducing the incidence or risk of cancer recurrence.

12 Claims, 12 Drawing Sheets

(56) References Cited

FOREIGN PATENT DOCUMENTS

| | | |
|---|---|---|
| CN | 103690525 | 4/2014 |
| CN | 103705503 | 4/2014 |
| IN | 225322 | 11/2008 |
| IN | 233470 | 3/2009 |
| WO | 9621443 | 7/1996 |
| WO | 9621444 | 7/1996 |
| WO | 9725035 | 7/1997 |
| WO | 98/18773 | 5/1998 |
| WO | 9818771 | 5/1998 |
| WO | 9833499 | 8/1998 |
| WO | 9833500 | 8/1998 |
| WO | 0107031 | 2/2001 |
| WO | 02074307 | 9/2002 |
| WO | 03063859 | 8/2003 |
| WO | 2005/049008 | 6/2005 |
| WO | 2006/032086 | 3/2006 |
| WO | 2006032086 | 3/2006 |
| WO | 2012/061409 | 5/2012 |
| WO | 2012061409 | 5/2012 |
| WO | 2013184755 | 12/2013 |

FUNCTIONALISED BENZOPYRAN COMPOUNDS AND USE THEREOF

FIELD OF THE INVENTION

The present invention relates broadly to anti-cancer agents. In particular, the present invention relates to selected benzopyran compounds, the preparation thereof, and their use in methods for treating cancer and reducing the incidence or risk of cancer recurrence.

BACKGROUND OF THE INVENTION

Cancer kills many thousands of people annually throughout the world. There have been significant breakthroughs made in the treatment and prevention of a wide variety of cancers. For example breast cancer has seen early screening programs as well as a variety of surgical techniques. However, these often prove physically and emotionally debilitating. Moreover, patients who have undergone surgery and subsequent chemotherapy often experience a recurrence. In recent years research has indicated the heterogeneous tumorigenic potential of cancer cells which has lead to the cancer stem cell (CSC) hypothesis. In brief, this hypothesis states that only a fraction of cells within a tumor have stem cell like features, including unlimited proliferative potential.

Further evidence in the literature supports the concept that tumours are complex heterogeneous organ-like systems with a hierarchical cellular organization, rather than simply as collections of homogeneous single lineage tumour cells. The initiator tumour cell retains the capacity to generate diverse progeny at various levels of differentiation, from uncommitted pluripotent stem cells, to committed progenitor cells, to fully differentiated senescent descendent cells. In this way, the tumour cell population itself is heterogeneous, adding diverse architecture afforded by the immune, stromal, and vascular cells that are also present in tumours. Some of the cells within this "cancer organ" or tumour have the potential for continued proliferation. The phylogeny of these tumor cells thus suggests the existence of a cell population that retains the ability to self-renew while also often possessing the capacity to generate progeny that differentiate. Hence, the cancer stem cell is defined as being a cell within a tumour that possesses the capacity to self-renew and to cause the heterogeneous lineages of cancer cells that comprise the tumour. Indeed laboratory evidence confirms that injection of isolated ovarian, brain, colon, breast, prostate or pancreatic cancer stem-like cells into immunocompromised mice results in the formation of tumours that are phenotypically identical to the original tumour and contain both stem-like cells and non-stem-like cells.

Hence there are two distinct populations; a relatively well-differentiated subset with limited proliferative capacity forming the bulk of the tumor which phenotypically characterises the disease, and a second smaller, less differentiated subset that contains clonogenic CSCs. Importantly CSCs exhibit multiple-drug resistance, an additional property that contributes to their longevity and metastatic potential by permitting them to survive toxic insults, including many of the drugs currently used to treat cancer. There is therefore a need to develop therapies that specifically target the self-renewal capabilities of the stem cell population, thereby abrogating the source of tumour recurrence as a result of resistance to conventional therapies.

Putative CSC markers that have been described for other malignancies, including acute myeloid leukemia (CD34-positive/CD38-negative), breast (CD44-positive/CD24-negative/-low/Linnegative), prostate (CD44-positive/_2_1-high/CD133-positive) and brain (CD133-positive/nestinpositive), have reflected those expressed by their normal tissue counterparts' original status. Recent evidence confirms that CD44+ ovarian cancer cells also posses the ability to form tumours in immunocompromised mice. As with other CSC phenotypes, ovarian cancer stem cells are slow growing, chemoresistant and form tumours in immunocompromised mice that are phenotypically identical to the original tumour in that there are mainly CD44−ve cells forming the bulk of the tumour with small pockets of CD44+ve cells.

Many advanced cancers recur despite the use of chemotherapeutic and radiation modalities that initially lead to therapeutic responses. For example, irradiation of glioblastomas can lead to significant radiographic responses, yet these tumors invariably recur and lead to patient death. Frequently, glioblastomas recur in a nodular pattern, suggesting a clonal or polyclonal source of recurrent tumor cells that are able to withstand conventional cytotoxic therapies, including radiation therapy, to cause recurrence of disease. Furthermore, recurrent tumors also demonstrate heterogeneity within the tumor cell population with regard to the presence of both CSCs and non-CSCs as well as in histologic and cytogenetic differences. This suggests that the CSCs that populated the original tumor may have withstood therapeutic intervention to repopulate the recurrent tumor even after the bulk of the tumor had been removed by resection or chemoradiation therapy, hence the concept that CSCs are the source of post-therapeutic tumour recurrence. A shift in therapeutic strategy that leads to the development of unique targeted agents that attack CSCs may enhance cancer care and prolong the survival of many patients.

The present inventors have surprisingly discovered that a selection of benzopyran compounds are able to exert powerful biological effects on non-CSCs as well as CSCs.

Such compounds offer alternative chemotherapeutic strategies for treating cancer and reducing the incidence or risk of cancer recurrence.

SUMMARY OF THE INVENTION

In a first aspect the present invention provides a compound of the general formula (I)

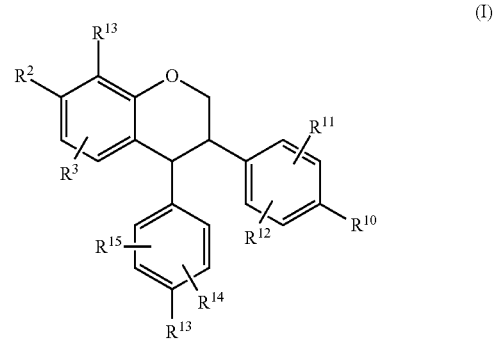

or a pharmaceutically acceptable salt, hydrate, derivative, solvate or prodrug thereof, wherein:

$R^1$ is selected from the group consisting of H and $C_1$-$C_6$ alkyl, $R^2$ is selected from the group consisting of: OH and $C_1$-$C_6$ alkoxy, $R^3$ is selected from the group consisting of: H, $C_1$-$C_6$ alkyl and halo, $R^{10}$ to $R^{12}$ are independently selected from the group consisting of: OH, $C_1$-$C_6$ alkyl, $C_1$-$C_6$ alkoxy and halo.

$R^{13}$ is selected from the group consisting of: OH, $C_1$-$C_6$ alkoxy, $NH_2$, NHMe, NHEt, $N(Me)_2$ and $N(Et)_2$, $R^{14}$ and $R^{15}$ are independently selected from the group consisting of: H, OH, $C_1$-$C_6$ alkyl and halo, or $R^{13}$ and one of $R^{14}$ and $R^{15}$ together form the following structure:

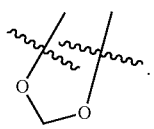 [SMILES: *OCO*]

In a second aspect the present invention provides a pharmaceutical composition comprising a compound of formula (I) according to the first aspect together with a pharmaceutically acceptable carrier, diluent or excipient.

In a third aspect the present invention provides a method for the treatment of cancer in a subject in need thereof, the method comprising administration to the subject of a therapeutically effective amount of a compound of formula (I) according to the first aspect, or a composition of the second aspect.

The method may further comprise administration of another chemotherapeutic agent.

The cancer may be a cancer that has recurred.

The cancer may be resistant to one or more chemotherapeutic agents.

The cancer may be pancreatic cancer, colorectal cancer, melanoma, prostate cancer, brain cancer (including paediatric and adult), ovarian cancer, breast cancer, lung cancer, liver cancer, uterine cancer, neuroblastoma, mesothelioma, malignant ascites or peritoneal cancer.

In a fourth aspect the present invention provides use of a compound of formula (I) according to the first aspect in the manufacture of a medicament for treating cancer.

The medicament may further comprise, or may be administered with, another chemotherapeutic agent.

In a fifth aspect the present invention provides a compound of formula (I) according to the first aspect for use in the treatment of cancer.

In a sixth aspect the present invention provides a method for reducing incidences of, or risk of, cancer recurrence in a subject deemed to be at risk of cancer recurrence, the method comprising administration to the subject of an effective amount of a compound of formula (I) according to the first aspect, or a composition of the second aspect.

The subject may be a subject who is in cancer remission. The subject may be in remission from ovarian cancer, brain cancer or some other cancer such as one or more of those recited above.

In a seventh aspect the present invention provides use of a compound of formula (I) according to the first aspect in the manufacture of a medicament for reducing incidences of, or risk of, cancer recurrence in a subject deemed to be at risk of cancer recurrence.

In an eighth aspect the present invention provides a compound of formula (I) according to the first aspect for use in reducing incidences of, or risk of, cancer recurrence in a subject deemed to be at risk of cancer recurrence.

In a ninth aspect the present invention provides a method for inducing apoptosis in, or inhibiting the proliferation of, a cancer stem cell, the method comprising contacting the cancer stem cell with an effective amount of a compound of formula (I) according to the first aspect.

The cancer stem cell may be an ovarian cancer stem cell or a brain cancer stem cell.

In a tenth aspect the present invention provides use of a compound of formula (I) according to the first aspect in the manufacture of a medicament for inducing apoptosis in, or inhibiting the proliferation of, a cancer stem cell.

In an eleventh aspect the present invention provides a method for treating a disease in a subject caused by cancer stem cells, the method comprising administration to the subject of a therapeutically effective amount of a compound of the formula (I) according to the first aspect, or a composition of the second aspect.

The disease may be cancer. The cancer. may be a metastatic cancer. The cancer stem cells may be ovarian cancer stem cells or brain cancer stem cells.

In a twelfth aspect the present invention provides use of a compound of the formula (I) according to the first aspect in the manufacture of a medicament for treating a disease caused by cancer stem cells.

In a thirteenth aspect the present invention provides a compound of the formula (I) according to the first aspect for use in treating a disease caused by cancer stem cells.

In a fourteenth aspect the present invention provides a method for preparing a compound of the formula (I) comprising the steps of:

(a) reducing a compound of formula (II) to produce a compound of formula (III):

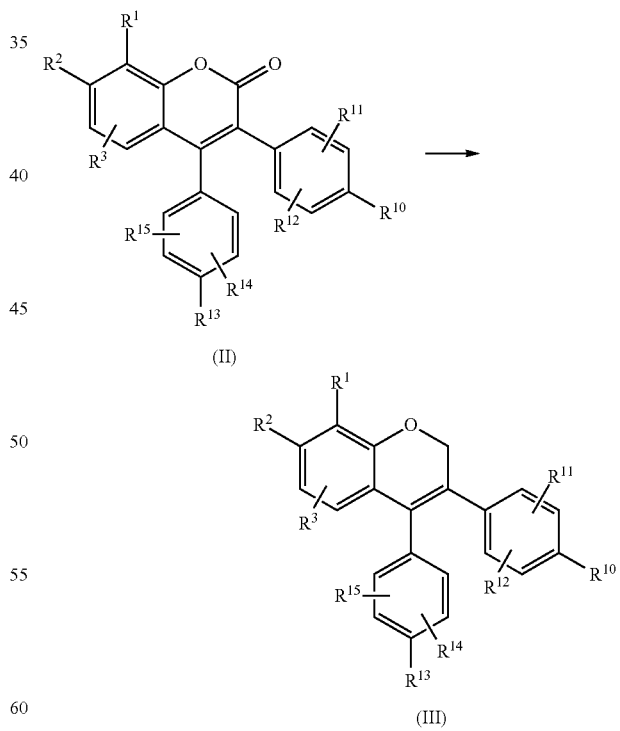

wherein in the compound of formula (II) $R^1$, $R^3$, and $R^{10}$ to $R^{15}$ are as defined in the first aspect, and $R^2$ is OAc or as defined in the first aspect, and in the compound of formula (III) $R^1$ to $R^3$ and $R^{10}$ to $R^{15}$ are as defined in the first aspect, and (b) hydrogenating a compound of formula (III) to produce a compound of formula (I),

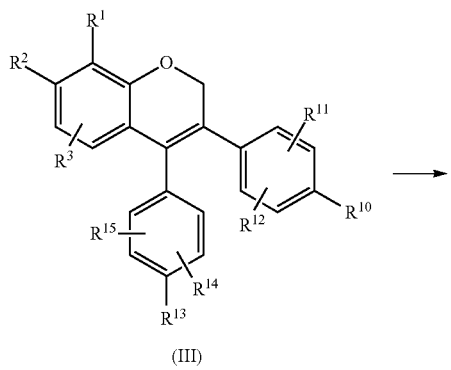

(III)

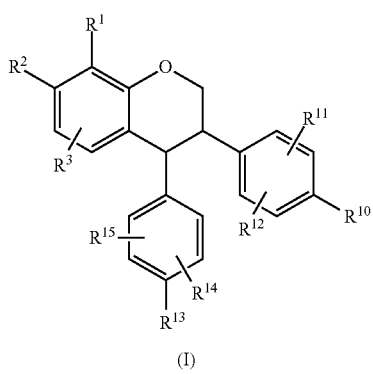

(I)

wherein $R^1$ to $R^3$, and $R^{10}$ to $R^{15}$ are as defined in the first aspect.

Step (a) may be carried out by reacting a compound of formula (II) with a borane reagent, for example borane dimethylsulfide complex, decborane, 9-BBN or borane tetrahydrofuran complex.

Step (b) may be carried out by reacting a compound of formula (III) with a heterogenous metal catalyst with a heterogenous metal catalyst under an atmosphere of hydrogen.

In one embodiment the method may further comprise:

(c) reacting a compound of formula (IV) with a compound of formula (V) to produce a compound of formula (II)

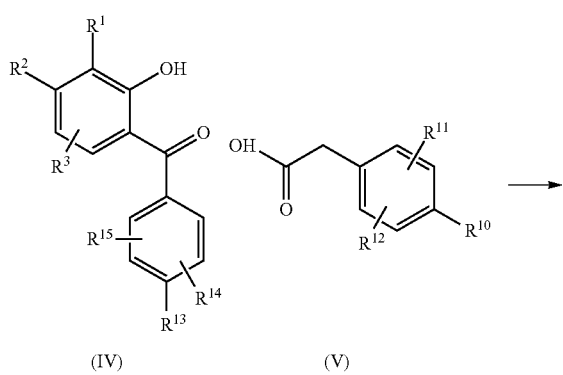

(IV)        (V)

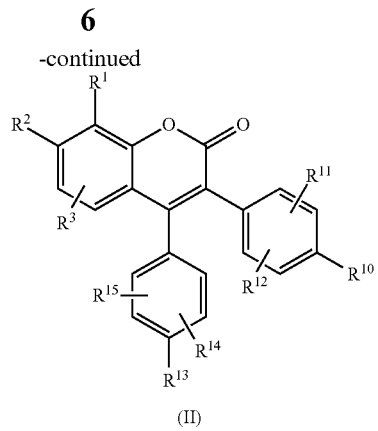

(II)

wherein in the compound of formula (II) $R^1$, $R^3$, and $R^{10}$ to $R^{15}$ are as defined in the first aspect, and $R^2$ is OAc or as defined in the first aspect, and in the compound of formula (IV) $R^1$ to $R^3$ and $R^{13}$ to $R^{15}$ are as defined in the first aspect, and in the compound of formula (V) $R^{10}$ to $R^{12}$ are as defined in the first aspect.

Step (c) may be carried out in the presence of a base.

In another embodiment the method may further comprise:

(d) reacting a compound of formula (VI) with a compound of formula (VII) to produce a compound of the formula (IV)

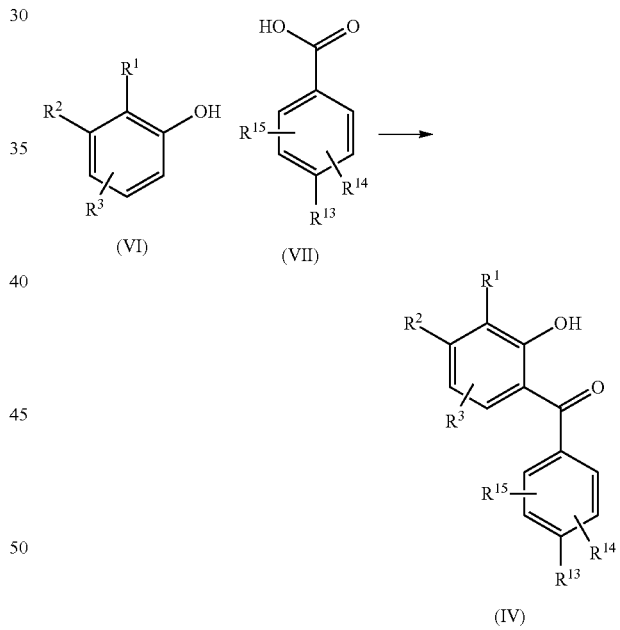

wherein $R^1$ to $R^3$, and $R^{13}$ to $R^{15}$ are as defined in the first aspect.

Step (d) may be carried out by combining compounds (VI) and (VII) in the presence of phosphorous oxychloride and zinc chloride. In an alternative embodiment step (d) may be carried out by reacting compound (VII) with thionyl chloride, followed by reaction with aluminium chloride and compound (VI).

DEFINITIONS

The following are some definitions that may be helpful in understanding the description of the present invention.

These are intended as general definitions and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

The terms "a" and "an" are used herein to refer to one or to more than one (i.e. to at least one) of the grammatical object of the article. By way of example, "an element" means one element or more than one element.

In the context of this specification, the term "alkyl" is taken to mean straight chain or branched chain monovalent saturated hydrocarbon groups having the recited number of carbon atoms. Examples of alkyl groups include, but are not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl and decyl.

In the context of this specification, the term "alkoxy" is taken to mean O-alkyl groups in which alkyl is as defined herein. Examples of alkoxy groups include, but are not limited to, methoxy, ethoxy, n-propoxy, isopropoxy, sec-butoxy and tert-butoxy.

In the context of this specification, the term "prodrug" means a compound which is able to be converted in vivo by metabolic means (e.g. by hydrolysis, reduction or oxidation) to a compound of the formula (I). For example, an ester prodrug of a compound of the formula (I) containing a hydroxy group may be hydrolysed in vivo to the parent molecule. Suitable esters are, for example, acetates, citrates, lactates, tartrates, malonates, oxalates, salicylates, propionates, succinates, fumarates and maleates.

In the context of this specification, the term "effective amount" includes a non-toxic but sufficient amount of an active compound to provide the stated effect. When used in reference to cancer recurrence "effective amount" means an amount of a compound of formula (I) that is required to reduce the incidence of, or risk of an individual experiencing cancer recurrence. Those skilled in the art will appreciate that the exact amount of a compound required will vary based on a number of factors and thus it is not possible to specify an exact "effective amount". However, for any given case an appropriate "effective amount" may be determined by one of ordinary skill in the art.

In the context of this specification, the term "therapeutically effective amount" includes a non-toxic but sufficient amount of an active compound to provide the desired therapeutic effect. Those skilled in the art will appreciate that the exact amount of a compound required will vary based on a number of factors and thus it is not possible to specify an exact "therapeutically effective amount". However, for any given case an appropriate "therapeutically effective amount" may be determined by one of ordinary skill in the art.

In the context of this specification, the terms "treating", "treatment", "preventing" and "prevention" refer to any and all uses which remedy cancer or symptoms thereof, prevent the establishment of cancer, or otherwise prevent, hinder, retard or reverse the progression of cancer or other undesirable symptoms in any way whatsoever. Thus, the terms "treating", "treatment", "preventing" and "prevention" and the like are to be considered in their broadest context. For example, treatment does not necessarily imply that a subject is treated until total recovery.

In the context of this specification, the term "subject" includes human and also non-human animals. As such, in addition to being useful in the treatment of cancer in humans, the compounds of the present invention also find use in the treatment of cancer in non-human animals, for example mammals such as companion animals and farm animals. Non-limiting examples of companion animals and farm animals include dogs, cats, horses, cows, sheep and pigs. Preferably, the subject is a human.

In the context of this specification the term "recurrence" as it relates to cancer is understood to mean the return of cancerous cells and/or a cancerous tumour after cancerous cells and/or a cancerous tumour have been successfully treated previously.

In the context of this specification the term "administering" and variations of that term including "administer" and "administration", includes contacting, applying, delivering or providing a compound or composition of the invention to an organism by any appropriate means.

DETAILED DESCRIPTION OF THE INVENTION

Figure 1:
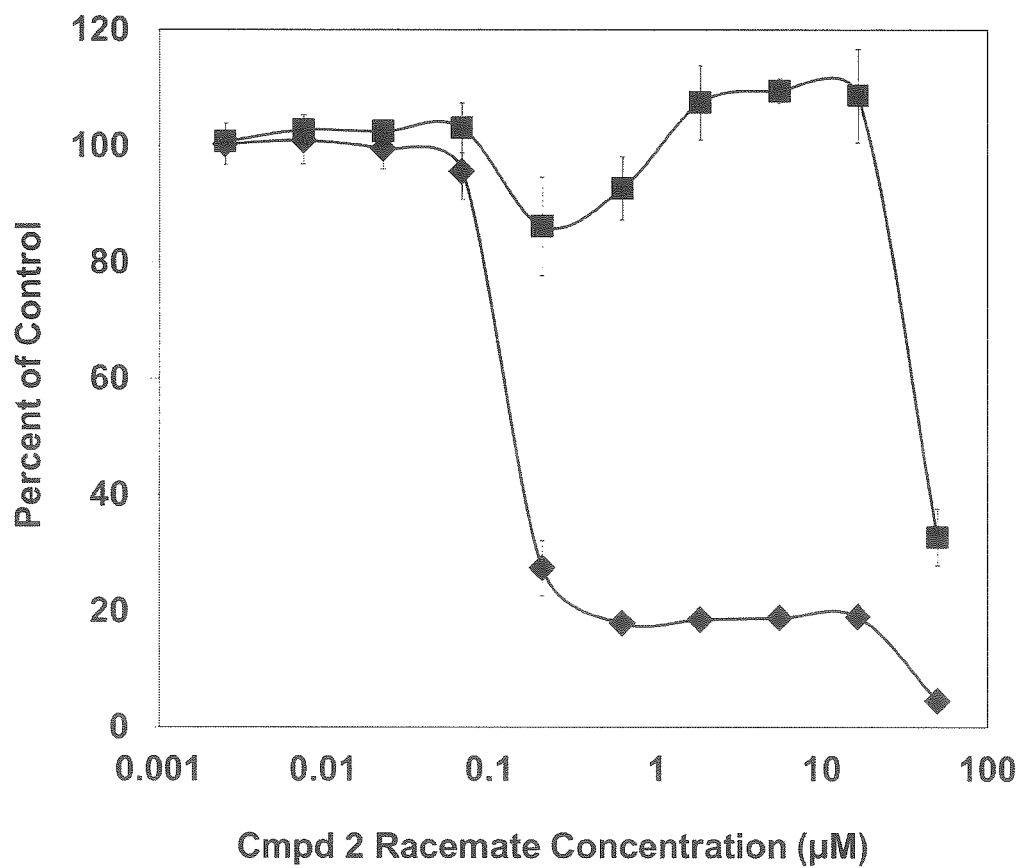
FIG. 1: Differential activity of compound 2 against two different GBM patient-derived explants; GBM14-CHA (diamonds) and ODA14-RAV (squares).

The present invention relates to selected benzopyran compounds of the general formula (I), the preparation of such compounds and their use in treating cancer and reducing the incidence of cancer recurrence. The compounds disclosed herein represent a selection invention with respect to US2012/0251630 and WO2012/061409.

In one aspect the present invention provides a compound of the general formula (I)

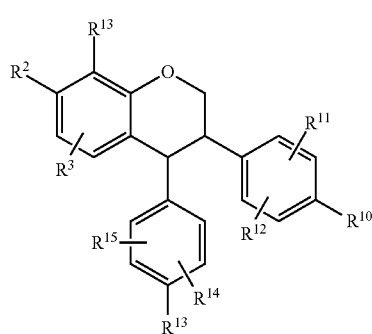

(I)

or a pharmaceutically acceptable salt, hydrate, derivative, solvate or prodrug thereof, wherein:

$R^1$ is selected from the group consisting of: H and $C_1$-$C_6$ alkyl, $R^2$ is selected from the group consisting of: OH and $C_1$-$C_6$ alkoxy, $R^3$ is selected from the group consisting of: H, $C_1$-$C_6$ alkyl and halo, $R^{10}$ to $R^{12}$ are independently selected from the group consisting of: OH, $C_1$-$C_6$ alkyl, $C_1$-$C_6$ alkoxy and halo, $R^{13}$ is selected from the group consisting of: OH, $C_1$-$C_6$ alkoxy, $NH_2$, NHMe, NHEt, $N(Me)_2$ and $N(Et)_2$.

$R^{14}$ and $R^{15}$ are independently selected from the group consisting of: H, OH, $C_1$-$C_6$ alkyl and halo, or $R^{13}$ and one of $R^{14}$ and $R^{15}$ together form the following structure:

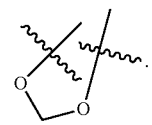

In one embodiment $R^1$ is selected from the group consisting of: H and $C_1$-$C_3$ alkyl.

In another embodiment $R^2$ is OH or OMe. In a further embodiment $R^2$ is OH.

In yet another embodiment $R^3$ is selected from the group consisting of: H, $C_1$-$C_3$ alkyl and halo. In a further embodiment $R^3$ is selected from the group consisting of: H, $C_1$-$C_3$ alkyl, F and Cl.

In still a further embodiment $R^{10}$ is selected from the group consisting of: OH, OMe and halo. In another embodiment $R^{10}$ is selected from the group consisting of: OH, OMe, F and Cl. In yet another embodiment $R^{10}$ is selected from the group consisting of: OH, OMe and F.

In a further embodiment $R^{11}$ and $R^{12}$ are independently selected from the group consisting of: OH, OMe, $C_1$-$C_4$ alkyl and F. In yet another embodiment $R^{11}$ and $R^{12}$ are independently selected from the group consisting of: OH, OMe, methyl, tert-butyl and F. In still a further embodiment $R^{11}$ and $R^{12}$ are independently selected from the group consisting of: OMe, methyl, tert-butyl and F. In yet another embodiment $R^{11}$ and $R^{12}$ are independently selected from the group consisting of: OH, OMe, tert-butyl and F. In still a further embodiment $R^{11}$ and $R^{12}$ are independently selected from the group consisting of: OMe, tert-butyl and F.

In another embodiment $R^{13}$ is selected from the group consisting of: OH, OMe, $NH_2$, NHEt and $N(Et)_2$.

In a further embodiment $R^{14}$ and $R^{15}$ are independently selected from the group consisting of: H, F, Cl and methyl.

In still a further embodiment $R^{13}$ and one of $R^{14}$ and $R^{15}$ form the following structure:

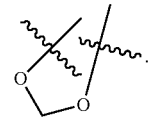

In one embodiment the compounds of formula (I) have the following structure

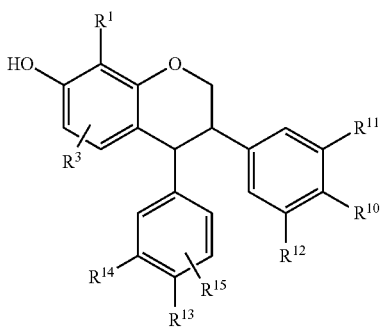

(Ia)

wherein $R^1$, $R^3$ and $R^{10}$ to $R^{15}$ are as defined above.

In one embodiment $R^1$ is selected from the group consisting of: H and $C_1$-$C_6$ alkyl. In another embodiment $R^1$ is selected from the group consisting of: H and $C_1$-$C_3$ alkyl In a further embodiment $R^3$ is selected from the group consisting of: H, $C_1$-$C_6$ alkyl and halo. In a further embodiment $R^3$ is selected from the group consisting of: H, $C_1$-$C_3$ alkyl, F and Cl.

In another embodiment $R^{10}$ is selected from the group consisting of: OH, OMe and halo. In still a further embodiment $R^{10}$ is selected from the group consisting of: OH, OMe, F and Cl. In another embodiment $R^{10}$ is selected from the group consisting of: OH, OMe and F.

In still a further embodiment $R^{11}$ is selected from the group consisting of: tert-butyl, OMe, methyl and halo. In yet another embodiment $R^{11}$ is selected from the group consisting of: tert-butyl, OMe, methyl, F and Cl. In yet another embodiment. $R^{11}$ is selected from the group consisting of: tert-butyl, OMe, methyl and F.

In a further embodiment $R^{12}$ is selected from the group consisting of: OMe, tert-butyl, methyl and halo. In yet another embodiment $R^{12}$ is selected from the group consisting of: OMe, tert-butyl, methyl, F and Cl. In still a further embodiment $R^{12}$ is selected from the group consisting of: OMe, methyl, tert-butyl and F.

In still a further embodiment $R^{11}$ is selected from the group consisting of: tert-butyl, OMe, and halo. In yet another embodiment $R^{11}$ is selected from the group consisting of: tert-butyl, OMe, F and Cl. In yet another embodiment. $R^{11}$ is selected from the group consisting of: tert-butyl, OMe and F.

In a further embodiment $R^{12}$ is selected from the group consisting of: OMe, tert-butyl and halo. In yet another embodiment $R^{12}$ is selected from the group consisting of: OMe, tert-butyl, F and Cl. In still a further embodiment $R^{12}$ is selected from the group consisting of: OMe, tert-butyl and F.

In yet another embodiment $R^{13}$ is selected from the group consisting of: OH, OMe, $NH_2$, NHEt and $NEt_2$.

In another embodiment $R^{14}$ and $R^{15}$ are independently selected from the group consisting of: H, halo and methyl. In another embodiment $R^{14}$ and $R^{15}$ are independently selected from the group consisting of: H, F, Cl and methyl.

In still a further embodiment $R^{13}$ and one of $R^{14}$ and $R^{15}$ form the following structure:

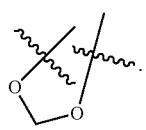

In one embodiment, $R^1$ is selected from the group consisting of: H and $C_1$-$C_3$ alkyl, $R^3$ is selected from the group consisting of: H, $C_1$-$C_3$ alkyl, F and Cl, $R^{10}$ is selected from the group consisting of: OMe, OH and F, $R^{11}$ and $R^{12}$ are independently selected from the group consisting of: tert-butyl, methyl, OMe and F, $R^{13}$ is selected from the group consisting of: OMe and OH and $R^{14}$ and $R^{15}$ are independently selected from the group consisting of: H, F, Cl and methyl.

In another embodiment, $R^1$ is selected from the group consisting of: H and $C_1$-$C_3$ $R^3$ is selected from the group consisting of: H, $C_1$-$C_3$ alkyl, F and Cl, $R^{10}$ is selected from the group consisting of: OMe, OH and F, $R^{11}$ and $R^{12}$ are independently selected from the group consisting of: tert-butyl, methyl, OMe and F, $R^{13}$ is selected from the group consisting of: OMe and OH and $R^{14}$ and $R^{15}$ are independently selected from the group consisting of: H, F, Cl and methyl, or $R^{13}$ and one of $R^{14}$ and $R^{15}$ form the following structure:

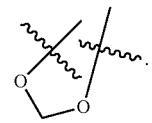

In a further embodiment. $R^1$ and $R^3$ are independently selected from the group consisting of: H, methyl or ethyl, $R^{10}$ is selected from the group consisting of: OMe, OH and F, $R^{11}$ and $R^{12}$ are independently selected from the group consisting of: tert-butyl, methyl. OMe and F, $R^{13}$ is selected from the group consisting of: OMe and OH and $R^{14}$ and $R^{15}$ are independently selected from the group consisting of: H, F and methyl. In this embodiment $R^{15}$ may be ortho or meta to $R^{13}$.

In another embodiment, $R^1$ and $R^3$ are independently selected from the group consisting of: H, methyl or ethyl, $R^{10}$ is selected from the group consisting of: OMe, OH and F, $R^{11}$ and $R^{12}$ are independently selected from the group consisting of: tert-butyl, methyl, OMe and F, $R^{13}$ is selected from the group consisting of: OMe and OH and $R^{14}$ and $R^{15}$ are independently selected from the group consisting of: H, F and methyl, or $R^{13}$ and one of $R^{14}$ and $R^{15}$ form the following structure:

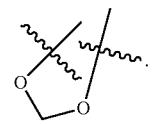

In one embodiment, $R^1$ and $R^3$ are independently selected from the group consisting of: H, methyl or ethyl, $R^{10}$ is selected from the group consisting of: OMe, OH and F, $R^{11}$ and $R^{12}$ are independently selected from the group consisting of: tert-butyl, OMe and F, $R^{13}$ is selected from the group consisting of: OMe and OH and $R^{14}$ and $R^{15}$ are independently selected from the group consisting of: H, F and methyl. In this embodiment $R^{15}$ may be ortho to $R^{13}$.

In another embodiment, $R^1$ and $R^3$ are independently selected from the group consisting of: H, methyl or ethyl, $R^{10}$ from the selected fro the group consisting of: OMe, OH and F, $R^{11}$ and $R^{12}$ are independently selected from the group consisting of: tert-butyl, OMe and F, $R^{13}$ is selected from the group consisting of: OMe and OH and $R^{14}$ and $R^{15}$ are independently selected from the group consisting of: H, F and methyl, or R[13] and one of R[14] and R[15] form the following structure:

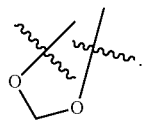

In one embodiment, R[1] is selected from the group consisting of: H and $C_1$-$C_3$ alkyl, R[3] is selected from the group consisting of: H, $C_1$-$C_3$ alkyl, F and Cl, R[10] is selected from the group consisting of: OMe, OH and F, R[11] and R[12] are independently selected from the group consisting of: tert-butyl, methyl, OMe and F, R[13] is selected from the group consisting of: OMe, OH, $NH_2$, NHEt and $NEt_2$ and R[14] and R[15] are independently selected from the group consisting of: H, F, Cl and methyl.

In another embodiment, R[1] is selected from the group consisting of: H and $C_1$-$C_3$ alkyl, R[3] is selected fro the group consisting of: H, $C_1$-$C_3$ alkyl, F and Cl, R[10] is selected from the group consisting of: OMe, OH and F, R[11] and R[12] are independently selected from the group consisting of: tert-butyl, methyl, OMe and F, R[13] is selected from the group consisting of: OMe, OH, $NH_2$, NHEt and $NEt_2$ and R[14] and R[15] are independently selected from the group consisting of: H, F, Cl and methyl, or R[13] and one of R[14] and R[15] form the following structure:

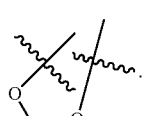

Exemplary compounds according to formula (I) include:

1

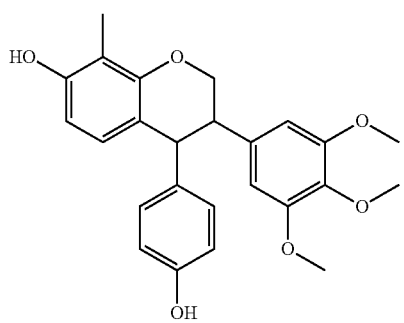

2

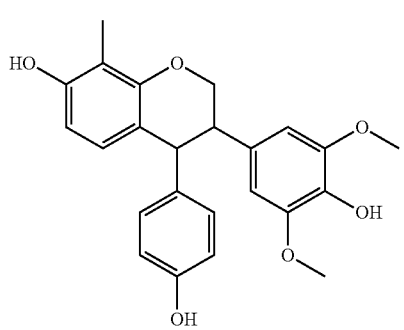

-continued

3

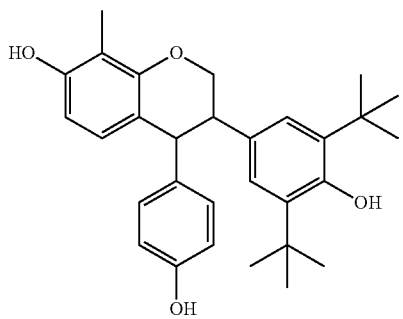

4

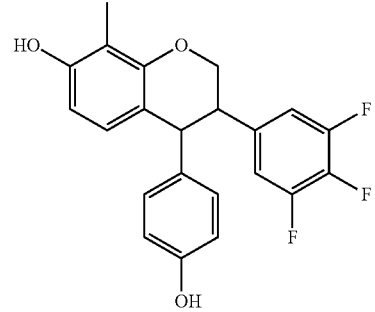

5

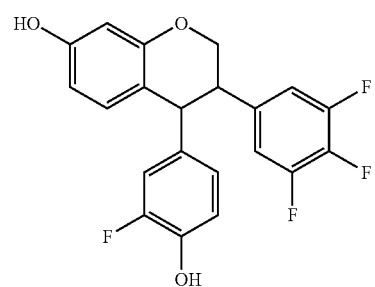

6

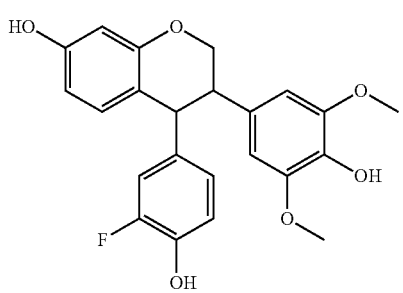

7

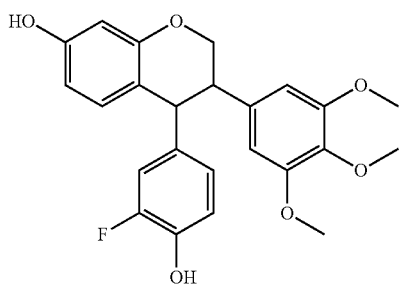

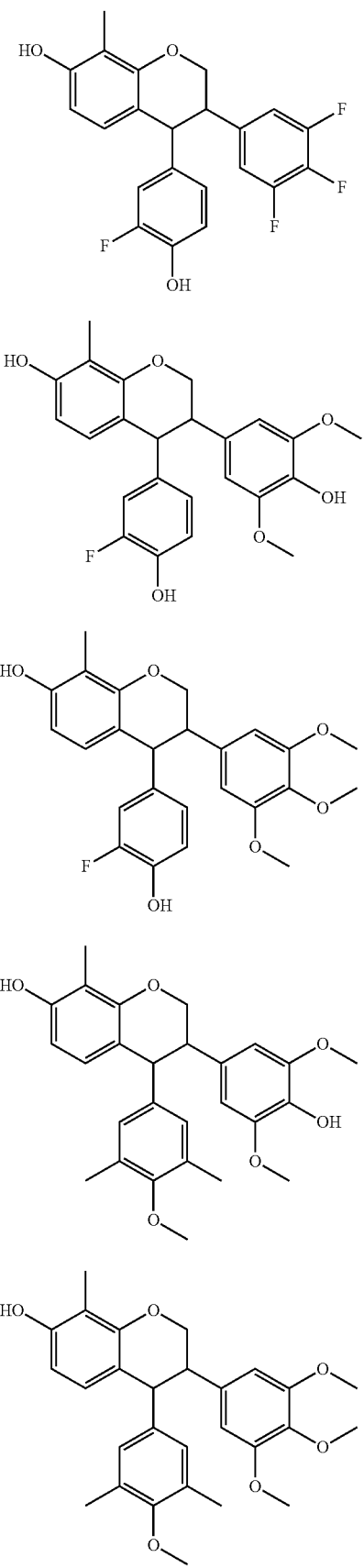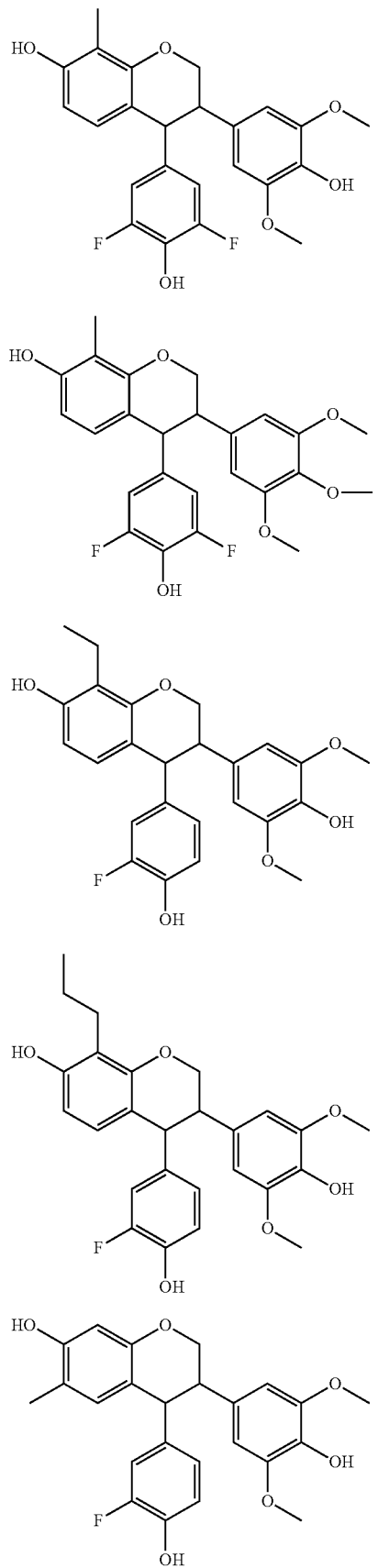

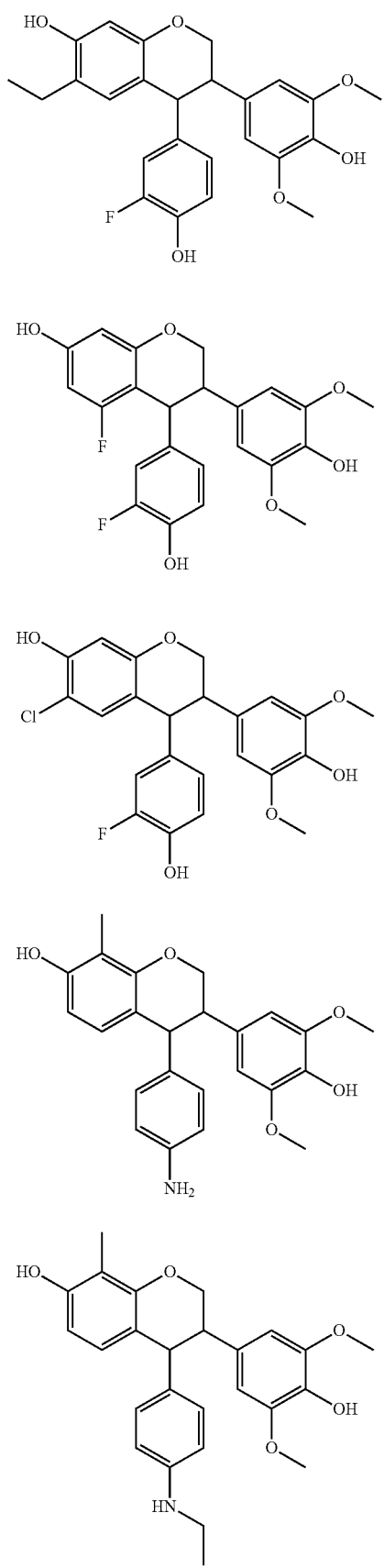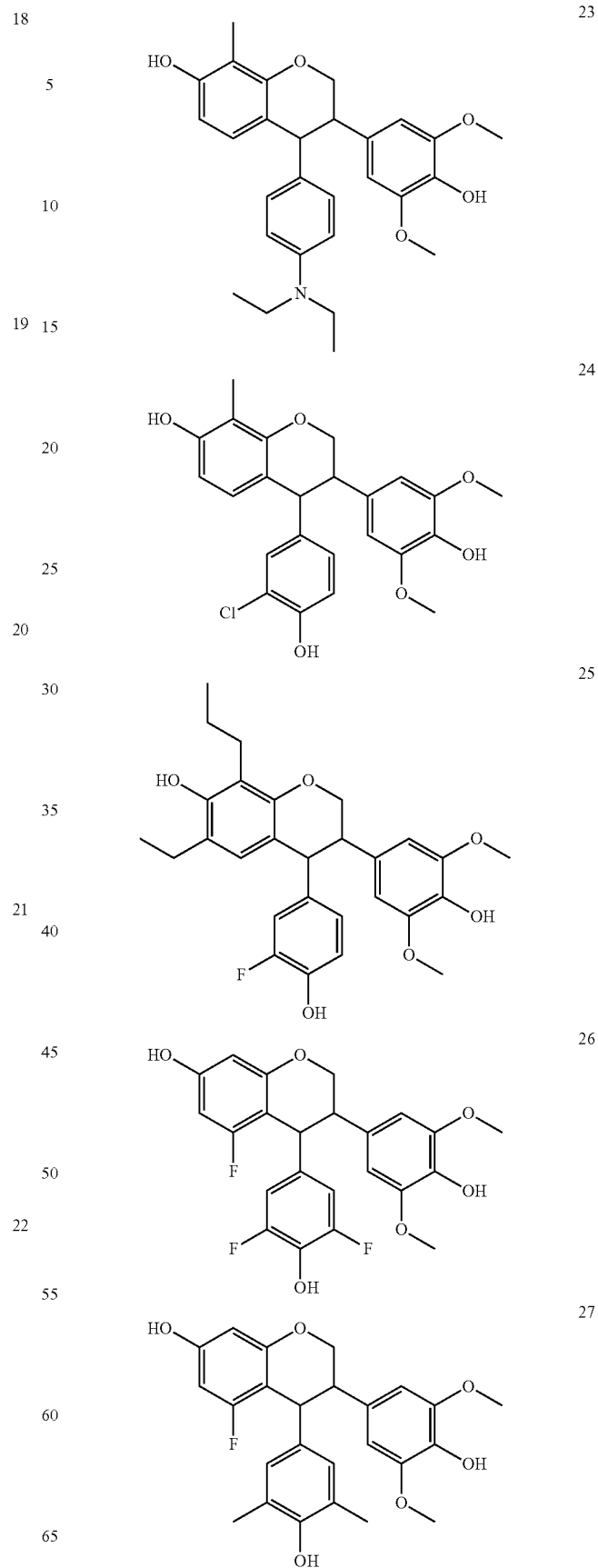

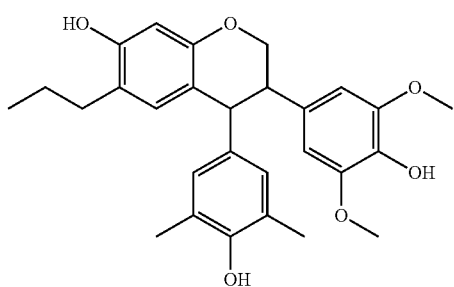
28
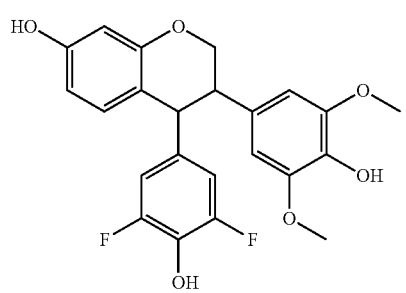
29
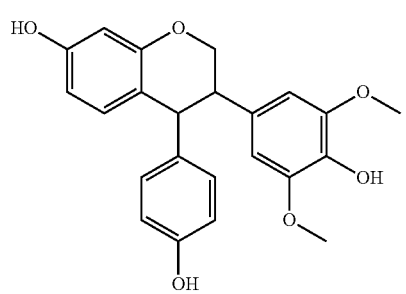
30
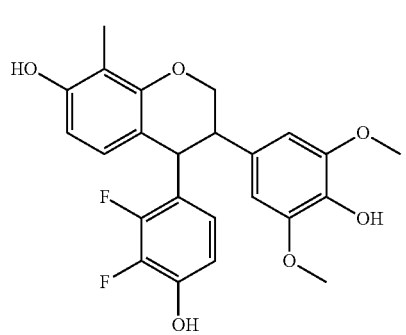
31
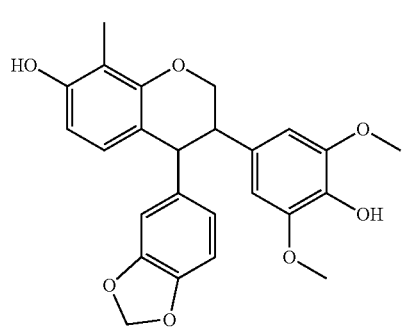
32
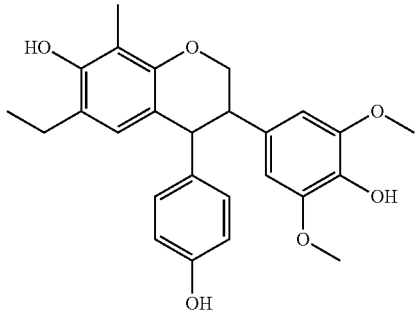
33
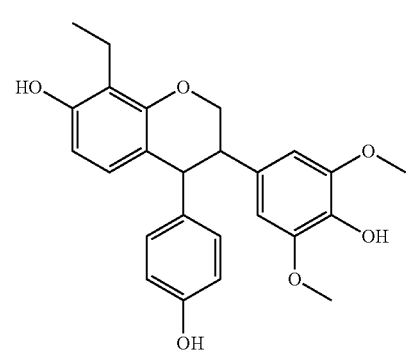
34
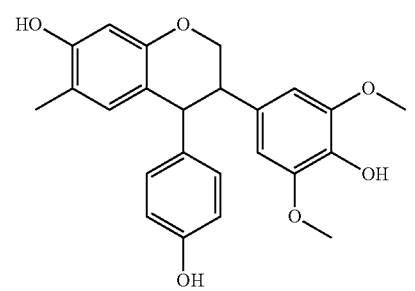
35
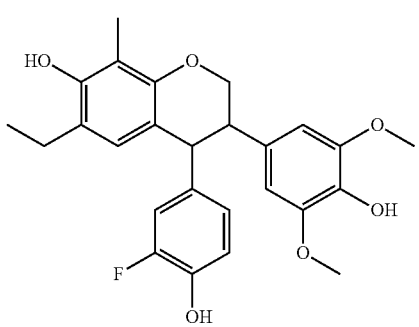
36
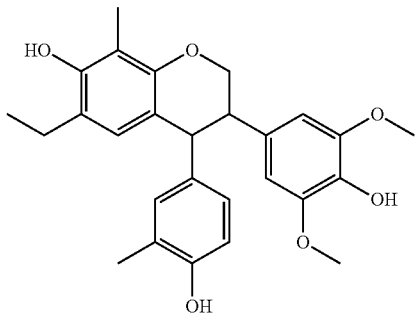
37

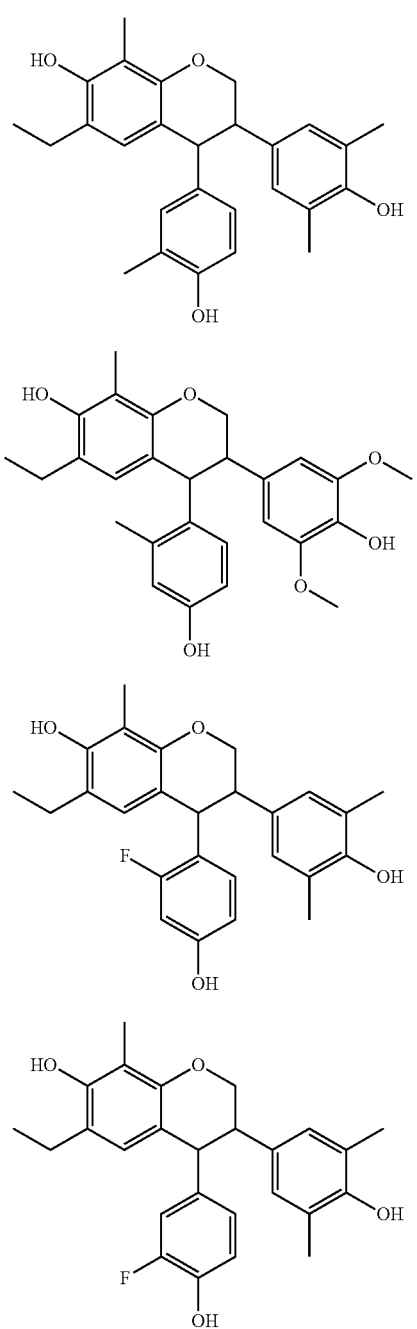

In one embodiment the compound of formula (I) is selected from the group consisting of: compounds 1 to 14, 16, 18-22, 24 and 32-41. In another embodiment the compound of formula (I) is selected from the group consisting of: compounds 1 to 14, 16, 18-22, 24 and 32-40. In another embodiment the compound of formula (I) is selected from the group consisting of: compounds 1 to 14, 16, 18-22, 24 and 32-35. In another embodiment the compound of formula (I) is selected from the group consisting of: compounds 1 to 14, 16, 18-22, 24 and 32-36. In another embodiment the compound of formula (I) is selected from the group consisting of: compounds 2, 6, 9, 13, 16, 18-22, 24 and 32-41. In another embodiment the compound of formula (I) is selected from the group consisting of: compounds 2, 6, 9, 13, 16, 18-22, 24 and 32-40. In a further embodiment the compound of formula (I) is selected from the group consisting of compounds 2, 6, 9, 13, 16, 18-22, 24 and 32-36. In a further embodiment the compound of formula (I) is selected from the group consisting of compounds 2, 6, 9, 13, 16, 18-22, 24 and 32-35. In a further embodiment the compound of formula (I) is selected from compounds 33 and 36 to 41. In a further embodiment the compound of formula (I) is selected from compounds 33, 36, 37 and 39. In another embodiment the compound of formula (I) is selected from the group consisting of compounds 2, 9 and 36. In another embodiment the compound of formula (I) is selected from the group consisting of compounds 2, 9, 20, 33 and 36. In another embodiment the compound of formula (I) is selected from the group consisting of compounds 2, 9, 33 and 36. In another embodiment the compound of formula (I) is selected from the group consisting of compounds 2, 6, 9, 13 and 36 to 41. In another embodiment the compound of formula (I) is selected from the group consisting of compounds 2, 6, 9, 13 and 36 to 40. In another embodiment the compound of formula (I) is selected from the group consisting of compounds 2, 6, 9, 13, 36, 37 and 39. In another embodiment the compound of formula (I) is compound 2. In another embodiment the compound of formula (I) is compound 9. In another embodiment the compound of formula (I) is compound 36. In alternative embodiments the compound of formula (I) may be any combination of one or more of compounds 1 to 41.

The compounds of formula (I) include at least two chiral centres. The present invention includes all enantiomers and diastereoisomers as well as mixtures thereof in any proportions. The invention also extends to isolated enantiomers or pairs of enantiomers. Methods of separating enantiomers and diastereoisomers are well known to persons skilled in the art. In some embodiments compounds of the formula (I) are racemic mixtures. In other embodiments compounds of the formula (I) are present in optically pure form.

It will also be recognised by those skilled in the art that in the compounds of the formula (I) the phenyl substituents attached to the heterocyclic ring can be either cis or trans relative to each other. Preferably, in the compounds of formula (I) these substituents will be cis relative to each other. Alternatively, in the compounds of formula (I) these substituents may be trans relative to each other.

In some embodiments compounds of the formula (I) including compounds 1 to 41 have the following structure:

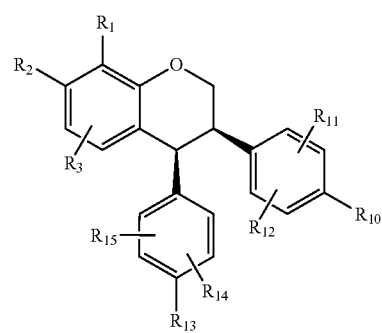

In other embodiments compounds of the formula (I) including compounds 1 to 41 have the following structure:

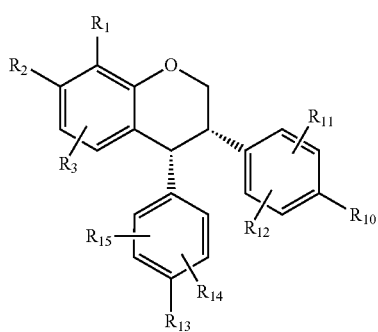

Compounds of the formula (I) are also taken to include hydrates and solvates. Solvates are complexes formed by association of molecules of a solvent with a compound of the formula (I). In the case of compounds of the formula (I) that are solids, it will be understood by those skilled in the art that such compounds may exist in different crystalline or polymorphic forms, all of which are intended to be within the scope of the present invention.

The compounds of formula (I) may be in the form of pharmaceutically acceptable salts. Such salts are well known to those skilled in the art. S. M. Berge et al. describe pharmaceutically acceptable salts in detail in *J. Pharmaceutical Sciences*, 1977, 66:1-19. Pharmaceutically acceptable salts can be prepared in situ during the final isolation and purification of compounds of the formula (I), or separately by reacting the free base compound with a suitable organic acid. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, ascorbic, glucoronic, fumaric, maleic, pyruvic, alkyl sulfonic, arylsulfonic, aspartic, glutamic, benzoic, anthranilic, rnesylic, salicylic, p-hydroxybenzoic, phenylacetic, mandelic, ambonic, pamoic, pantothenic, sulfanilic, cyclohexylaminosulfonic, stearic, algenic, β-hydroxybutyric, galactaric, and galacturonic acids. Suitable pharmaceutically acceptable base addition salts of the compounds of the present invention include metallic salts made from lithium, sodium, potassium, magnesium, calcium, aluminium, and zinc, and organic salts made from organic bases such as choline, diethanolamine, morpholine. Alternatively, organic salts made from N,N'-dibenzylethylenediamine, chloroprocaine, choline, diethanolamine, ethylenediamine, meglumine (N-methylglucamine), procaine, ammonium salts, quaternary salts such as tetramethylammonium salt, amino acid addition salts such as salts with glycine and arginine.

The compounds of formula (I) also extend to include all derivatives with physiologically cleavable leaving groups that can be cleaved in vivo to provide the compounds of the formula (I). Suitable leaving groups include acyl, phosphate, sulfate, sulfonate, and preferably are mono-, di- and per-acyl oxy-substituted compounds, where one or more of the pendant hydroxy groups are protected by an acyl group, preferably an acetyl group. Typically, acyloxy substituted compounds are readily cleavable to the corresponding hydroxy-substituted compounds.

Representative compounds of the formula (I) may be synthesised as described below. In the first step of the synthesis, benzophenone intermediate (IV) is prepared from a suitably functionalized phenol (VI) and a suitably functionalized benzoic acid (VII) according to Scheme 1.

Scheme 1: Preparation of a benzophenone intermediate

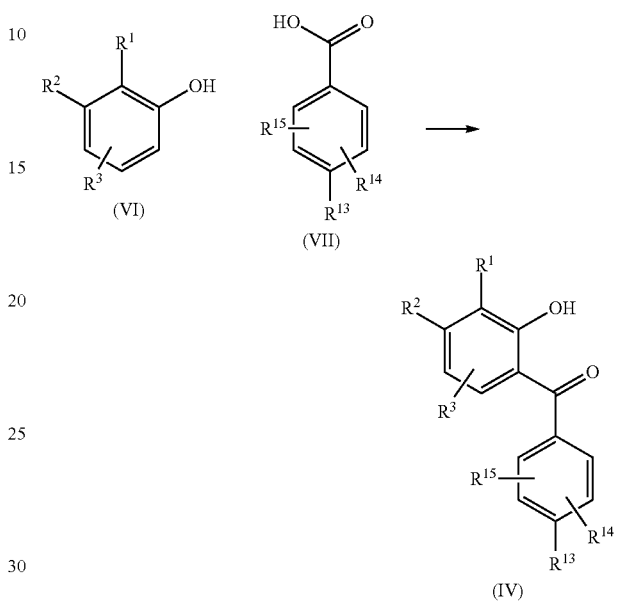

The relative location of substituents $R_{14}$ and $R_{15}$ on the phenyl ring of compound (VII) may be selected based on the substitution pattern required on the 4-phenyl ring of the compound of formula (I) being prepared. Where appropriate or necessary, protecting groups may be employed. Standard protecting groups are known to those skilled in the art and include those described, for example, in '*Protective Groups in Organic Synthesis*' by Theodora Greene and Peter Wuts (Third edition, 1999, John Wiley and Sons).

Typically, in the reaction depicted in Scheme 1, the phenolic compound (VI) and the benzoic acid compound (VII) are reacted under acylating conditions. For example, in one method described in the *Indian Journal of Chemistry*, 1971, 619-62, the phenolic compound (VI) and the benzoic acid compound (VII) may be combined with phosphorous oxychloride and zinc chloride and the mixture heated for a period of time sufficient for the reaction to proceed substantially to completion. The precise period of time will depend on the scale of the reaction, however those skilled in the art will readily be able to determine suitable time and temperature conditions. In a typical reaction, the reagents are heated at a temperature of about 70° C. for about 1 to 3 hours. When the reaction is judged to be sufficiently complete, the reaction mixture is cooled, for example by pouring onto ice, after which the benzophenone intermediate (IV) may be isolated and purified using standard techniques known to those skilled in the art.

In an alternative method, the benzoic acid compound (VII) may be stirred in refluxing thionyl chloride for about 2 to 6 hours, followed by addition of catalytic N,N-dimethylformamide in a suitable organic solvent (for example dichloromethane), for about 20 mins to 1 hour. After removing residual thionyl chloride the mixture is typically cooled (for example in an ice bath) then aluminium chloride and the phenolic compound (VI) are added and the mixture stirred for a suitable period of time, typically about 18 to 36 hours, while slowly warming to room temperature, then heated at reflux for about 2 to 8 hours. The reaction may be conducted under an inert atmosphere.

The benzophenone intermediate (IV) may be purified using standard techniques known to those skilled in the art. For example, the benzophenone intermediate (IV) may be collected by filtration, washed (for example with water), then recrystallised from a suitable solvent system. Examples of recrystallisation solvents include methanol, ethanol, water and mixtures thereof. Alternatively, the benzophenone intermediate (IV) may. be purified by column chromatography.

The next step of the synthesis involves reaction of the benzophenone intermediate (IV) with a suitably functionalized phenylcarboxylic acid (V) to provide functionalized benzopyranone (II) (see Scheme 2). The relative location of substituents $R_{11}$ and $R_{12}$ on the phenyl ring of compound (V) may be selected based on the substitution pattern required on the 3-phenyl ring of the compound of formula (I) being prepared. Where appropriate or necessary, protecting groups may be employed.

time periods will depend on the scale of the reaction and the particular reagents employed. Typically, the reagents may be warmed at a temperature of about 40-60° C. (for example about 50° C.) for about 20 to 30 minutes to ensure that all of the reagents are in solution, then heated at a higher temperature, such as about 130-150° C. (for example about 135° C.), for about 6 to 48 hours (for example about 18 hours). The functionlized benzopyranone (II) may be isolated by conventional means, such as solvent extraction (for example, using an organic solvent such as ethyl acetate, chloroform, or the like), and washing with aqueous alkaline solution (for example sodium carbonate, or sodium hydrogen carbonate solution), followed by standard purification using techniques known to those skilled in the art, such as column chromatography, recrystallisation from a suitable solvent (for example ethanol or an ethanol/water mixture), or trituation with a suitable solvent (for example methanol, ethanol or mixtures thereof).

The next step of the synthesis involves reduction of the lactone of the functionalized benzopyranone (II) to provide functionalized chromene compound (III) (see Scheme 3).

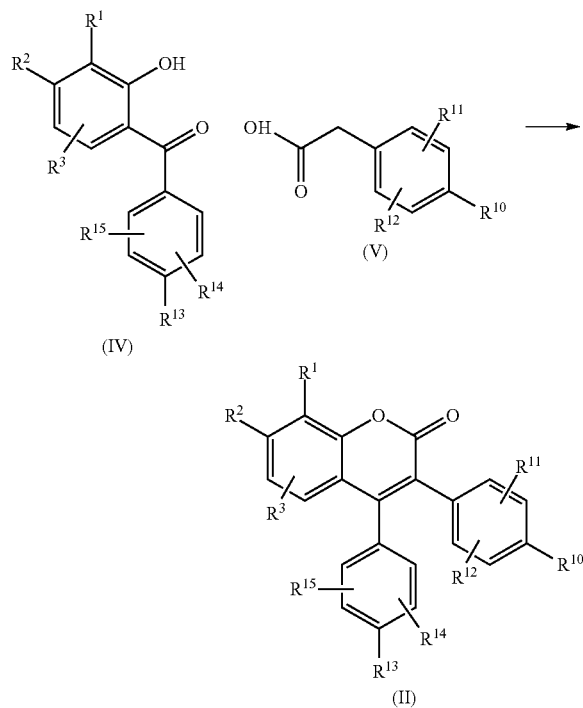

Scheme 2: Preparation of a functionalized benzopyranone

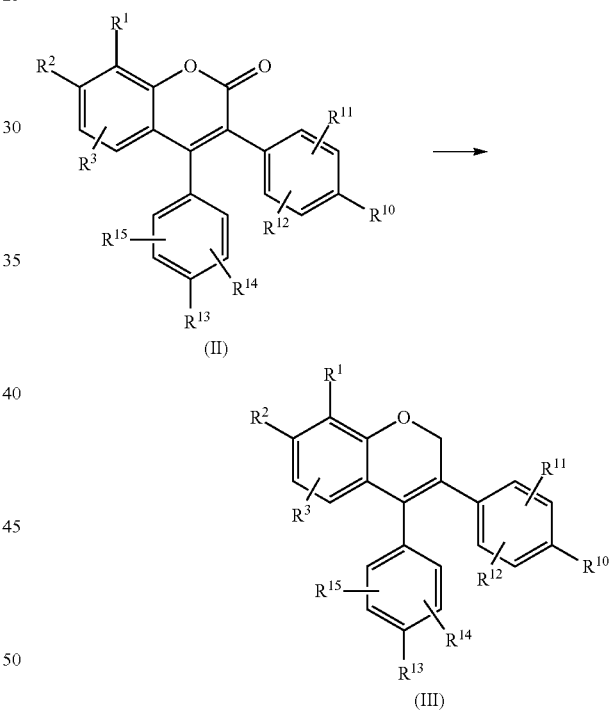

Scheme 3. Preparation of a functionalized chromene

Typically, in the condensation reaction depicted in Scheme 2, the benzophenone intermediate (IV) is reacted with the suitably functionalized phenylacetic acid (V) in the presence of a base and acetic anhydride. Typically, the base is a non-nucleophilic base, such as N,N-diisopropylethylamine (DIEA), N-methylmorpholine or triethylamine. During this reaction any hydroxy substituents present on the phenyl rings may be converted to the corresponding acetate. The reaction is typically carried out with heating at a temperature and for a period of time until the reaction is judged to be substantially complete (for example by TLC or GC analysis). Those skilled in the art will know that suitable Typically, the reduction reaction is carried out by treating the benzopyranone (II) with a suitable reducing agent capable of reducing the ketone moiety of the pyranone ring. Preferably, the reducing reagent selectively reduces the ketone moiety of the pyranone ring but does not reduce the 3,4 double bond. The reduction may also deprotect any acylated hydroxy groups present on the phenyl rings. Suitable reducing agents will be known to those skilled in the art and include borane reagents, such as, for example borane dimethylsulfide complex, decborane, 9-BBN and borane tetrahydrofuran complex. In some embodiments the reducing agent is borane dimethylsulfide. The reduction may be facilitated by the use of a chiral auxiliary. For example, borane dimethylsulfide is amenable to asymmetric ketone reduction using a chiral oxazaborolidine catalyst (Corey, E. J.; Helal, C. J. *Angew. Chem. Int. Ed.* 1998, 1986). The reaction may be carried out in an organic solvent, such as tetrahydrofuran, toluene or chloroform. The reaction may be performed under an inert atmosphere at a temperature below room temperature, typically at a temperature from about −10° C. to about 10° C., or at about −5° C. to about 0° C., or at about 0° C., for about 15 minutes to about 4 hours, typically for about 30 minutes to about 2 hours. When the reduction reaction is judged to be complete (or substantially complete) the product may be isolated by acidic work up using standard methods known to the skilled person, then purified using conventional techniques such as column chromatography.

With globally deprotected chromene compound (III) in hand, the final step of the synthesis involves catalytic cisoid reduction of the olefin of chromene compound (III) to give compounds of the formula (I) (see Scheme 4).

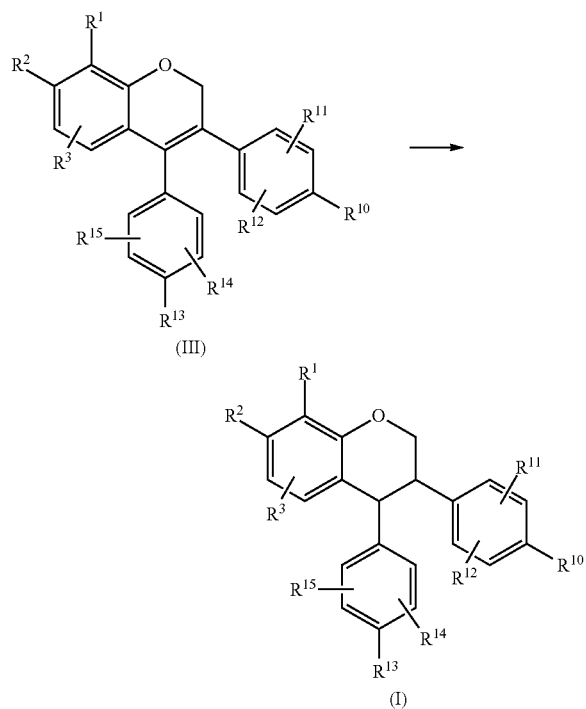

The reduction of the double bond may be performed by hydrogenation using reagents and conditions that are well known to those skilled in the art. Suitable reagents include heterogenous metal catalysts, such as palladium and platinum catalysts in the presence of a hydrogen atmosphere. Presently preferred catalysts include, but are not limited to, Pd/C, Pd(OH)$_2$/C, Pt/C, Raney Nickel, Rh catalysts, including chiral Rh catalysts, such as Rh DIPAMP and Wilkinsons catalysts. Examples of suitable solvents include methanol and ethanol. The reaction may be performed at room temperature or the reaction mixture may be heated (for example to about 50 to 60 °C.). Alternatively, the hydrogenation reaction may be performed under pressure. Those skilled in the art will readily be able to determine when the reaction is complete (or substantially complete) using standard techniques (for example TLC, GC-MS). The product may be purified using standard techniques (for example chromatography).

After purification, compounds of formula (I) may be substantially pure. For example, the compounds of formula (I) may be isolated in a form which is at least about 80%, 85%, 90%, 95%, 98%, 99%, 99.5% or 99.9% pure.

Compounds of the formula (I) may be obtained as racemic mixtures. Enantiomers may be isolated using techniques known to those skilled in the art, including chiral resolution, supercritical fluid chromatography and enantioselective syntheses. Individual enantiomers may be isolated in a substantially pure form or in an enantiomeric excess (ee). For example, in preferred embodiments an enantiomer may be isolated in an enantiomeric excess of about 70%, 75%, 80%, 85%, 90%, 92%, 95%, 96%, 97%, 98%, 99% or greater than 99%.

The present inventors have discovered that compounds of the formula (I) are able to exert surprisingly powerful biological effects on differentiated cancer cells as well as on undifferentiated cancer cells, which are variously referred to as "cancer stem cells" or "cancer progenitor cells". The biological effects may include inhibition of cell proliferation, induction of cell death, induction of cellular differentiation and reversal of aberrant behavior.

The compounds of formula (I) therefore find use in the treatment of cancer. In particular, the compounds of formula (I) may be used in the treatment of cancer where it is desirable to target both undifferentiated and differentiated cancer cells, and where the effect on both cancer cell types might be different or even opposite. For example, compounds of the formula (I) may induce cell death in differentiated cancer cells and induce cellular differentiation in undifferentiated cancer cells. In other embodiments compounds of the formula (I) may inhibit the proliferation of cancer stem cells and differentiated cancer stem cells, such as somatic cancer cells.

The compounds of formula (I) may be used in conjunction with, or alternatively in the absence of, other chemotherapeutic agents.

The compounds of formula (I) may be used in the treatment of cancer that is resistant to one or more chemotherapeutic agents.

By virtue of their biological effects on undifferentiated cancer cells the compounds of formula (I) find particular use in treating cancer that has recurred in a subject and in reducing the incidence of, or the risk of, recurrence of cancer in a subject deemed to be at risk of cancer recurrence, for example a subject who is in cancer remission. The subject may be in remission from a solid tumour as defined herein. The compounds of formula (I) may also find use in inducing apoptosis in, or inhibiting the proliferation of, cancer stem cells. The compounds of formula (I) may also find use in treating diseases caused by cancer stem cells, such as cancer. The cancer may be a metastatic cancer.

Furthermore, compounds of the formula (I) may possess superior pharmaceutical properties, such as improved resistance to conjugation via glucuronyl transferases and other water-solubilising transferases such as sulfases, which may be over-expressed on proliferative cells, such as cancer cells. This may advantageously confer superior pharmaceutical properties, such as an enhanced pharmacokinetic profile through reduced conjugation and elimination.

In all aspects of the invention the cancer may be a solid tumour, such as for example, breast cancer, lung cancer (NSCLC and SOLO), prostate cancer, ovarian cancer, uterine cancer, peritoneal cancer, brain cancer (including, for example, gliomas such as glioblastoma, Diffuse Intrinsic Pontine Glioma (DIPG) and medulloblastoma), skin cancer, colon cancer, bladder cancer, colorectal cancer, gastric cancer, liver cancer, pancreatic cancer, head and neck cancer, melanoma, malignant ascites, mesothelioma or neuroblastoma. The brain cancer may be adult or paediatric. The glioma may be temozolomide (TMZ) resistant or TMZ susceptible.

In particular embodiments the cancer is ovarian cancer, neuroblastoma, prostate cancer or brain cancer (including, for example, gliomas such as glioblastoma. DIPG and medulloblastoma). In other embodiments the cancer is ovarian cancer, prostate cancer or brain cancer (including, for example, gliomas such as glioblastoma. DIPG and medulloblastoma). In further embodiments the cancer is ovarian cancer, glioma, colorectal cancer, prostate cancer, breast cancer, lung cancer, liver cancer, melanoma or malignant ascites. In other embodiments the cancer may be pancreatic cancer, colorectal cancer, melanoma, prostate cancer, brain cancer (including paediatric and adult), ovarian cancer, breast cancer, lung cancer, liver cancer, uterine cancer, neuroblastoma, mesothelioma, malignant ascites or peritoneal cancer.

Compounds of formula (I) may find use in inducing apoptosis in, or inhibiting the proliferation of ovarian cancer stem cells. Accordingly, in one embodiment the invention provides a method for inducing apoptosis in, or inhibiting the proliferation of ovarian cancer stem cells, the method comprising contacting the ovarian cancer stem cells with an effective amount of a compound of formula (I). The compound of formula (I) may be any combination of one or more of compounds 1 to 41, The compound of formula (I) may be selected from compounds 1 to 14 and 32-41, or alternatively the compound of formula (I) may be selected from compounds 1 to 14 and 32-40, or alternatively may be selected from compounds 1 to 14, or alternatively may be selected from compounds 2, 6, 9, 13 and 36, or alternatively may be selected from compounds 2, 6, 9 and 13. The compound of formula (I) may be compound 2. The compounds of formula (I) may be used in the absence of other chemotherapeutic agents. The compounds may be in the form of the (+) enantiomer. The ovarian cancer stem cells may be resistant to cisplatin and/or paclitaxel. The compound of formula (I) may be administered intraperitoneally.

Compounds of formula (I) may find use in treating ovarian cancer in a subject. Accordingly, in one embodiment the invention provides a method for the treatment of ovarian cancer in a subject in need thereof, the method comprising administration to the subject of a therapeutically effective amount of a compound of formula (I). The cancer may be a cancer that has recurred. The compound of formula (I) may be any combination of one or more of compounds 1 to 41. The compound of formula (I) may be selected from compounds 1 to 14 and 32-41, or alternatively the compound of formula (1) may be selected from compounds 1 to 14 and 32-40, or alternatively may be selected from compounds 1 to 14, or alternatively may be selected from compounds 2, 6, 9, 13 and 36, or alternatively may be selected from compounds 2, 6, 9 and 13. The compound of formula (I) may be compound 2. The compounds of formula (I) may be used in the absence of other chemotherapeutic agents. The compounds may be in the form of the (+) enantiomer. The ovarian cancer may be resistant to cisplatin and/or paclitaxel. The compound of formula (I) may be administered intraperitoneally.

Compounds of formula (I) may find use in reducing the incidence of, or the risk of, cancer recurrence in a subject deemed to be at risk of cancer recurrence. Accordingly, in one embodiment the invention provides a method for reducing incidences of, or risk Of. cancer recurrence in a subject deemed to be at risk of cancer recurrence, the method comprising administration to the subject of an effective amount of a compound of formula (I). The subject deemed to be at risk of cancer recurrence may be a subject in remission from ovarian cancer or a subject in remission from brain cancer, such as glioma. The method may involve reducing incidences of, or risk of, ovarian cancer recurrence or brain cancer recurrence in the subject. The compound of formula (I) may be any combination of one or more of compounds 1 to 41. The compound of formula (I) may be selected from compounds 1 to 14, or alternatively may be selected from compounds 2, 6, 9 and 13. The compound of formula (I) may be compound 2 or compound 9. The compounds of formula (I) may be used in the absence of other chemotherapeutic agents. The compounds may be in the form of the (+) enantiomer.

Compounds of formula (I) may find use in treating a disease in a subject caused by ovarian cancer stem cells. Accordingly, in one embodiment the invention provides a method for treating a disease in a subject caused by ovarian cancer stem cells, the method comprising administration to the subject of a therapeutically effective amount of a compound of the formula (I). The disease may be cancer. The cancer may be ovarian cancer or some other cancer, for example a metastatic cancer. The cancer may be resistant to cisplatin and/or paclitaxel. The compound of formula (I) may be administered intraperitoneally. The compound of formula (I) may be any combination of one or more of compounds 1 to 41. The compound of formula (I) may be selected from compounds 1 to 14, or alternatively may be selected from compounds 2, 6, 9 and 13. The compound of formula (I) may be compound 2. The compounds of formula (I) may be used in the absence of other chemotherapeutic agents. The compounds may be in the form of the (+) enantiomer.

Compounds of formula (I) may find use in inducing apoptosis in, or inhibiting the proliferation of brain cancer stem cells, such as glioma stem cells. Accordingly, in one embodiment the invention provides a method for inhibiting the proliferation of brain cancer stem cells, such as glioma stem cells, the method comprising contacting the brain cancer stem cells with an effective amount of a compound of formula (I). The compound of formula (I) may be any combination of one or more of compounds 1 to 41. The compound of formula (I) may be selected from compounds 1 to 14 and 32-41, or alternatively the compound of formula (I) may be selected from compounds 1 to 14 and 32-40, or alternatively may be selected from compounds 1 to 14, or alternatively may be selected from compounds 2, 6, 9 and 36, or alternatively may be selected from compounds 2, 6 and 9, or alternatively may be selected from compounds 2, 6, 9 and 13, or alternatively may be selected from compounds 2 and 9. The compound of formula (I) may be compound 9. The compounds of formula (I) may be used in the absence of other chemotherapeutic agents. The compounds may be in the form of the (+) enantiomer.

Compounds of formula (I) may find use in treating a disease in a subject caused by brain cancer stem cells, such as glioma stem cells. Accordingly, in one embodiment the invention provides a method for treating a disease in a subject caused by brain cancer stem cells, such as glioma stem cells, the method comprising administration to the subject of a therapeutically effective amount of a compound of the formula (I). The disease may be cancer. The cancer may be brain cancer or some other cancer, for example a metastatic cancer. The compound of formula (I) may be any combination of one or more of compounds 1 to 41. The compound of formula (I) may be selected from compounds 1 to 14 and 32-41, or alternatively the compound of formula (I) may be selected from compounds 1 to 14 and 32-40, or alternatively may be selected from compounds 1 to 14, or alternatively may be selected from compounds 2, 6, 9 and 36, or alternatively may be selected from compounds 2, 6 and 9, or alternatively may be selected from compounds 2, 6, 9 and 13, or alternatively may be selected from compounds 2 and 9. The compound of formula (I) may be compound 9. The compounds of formula (I) may be used in the absence of other chemotherapeutic agents. The compounds may be in the form of the (+) enantiomer.

In another embodiment the invention provides a method for treating cancer in a subject in need thereof, the method comprising administration to the subject of a therapeutically effective amount of a compound of the formula (I). The cancer may be colorectal cancer, brain cancer (such as for example, glioma. DIPG or medulloblastoma), ovarian cancer, pancreatic cancer, prostate cancer, breast cancer, lung cancer, liver cancer, melanoma, neuroblastoma or malignant ascites. The brain cancer may be adult or paediatric. The cancer may be ovarian cancer, prostate cancer, brain cancer or neuroblastoma. The cancer may be ovarian cancer, prostate cancer or brain cancer. The compound of formula (I) may be any combination of one or more of compounds 1 to 41. The compound of formula (I) may be selected from compounds 1 to 14, 16, 18-22, 24 or 32-41, or alternatively may be selected from compounds 1 to 14, 16, 18-22, 24 or 32-40, or alternatively may be selected from compounds 1 to 14, 16, 18-22, 24 or 32-36, or alternatively may be selected from compounds 1 to 14, 16, 18-22, 24 or 32-35, or alternatively may be selected from compounds 2, 6, 9, 13 and 36, or alternatively may be selected from compounds 2, 6, 9 and 13. The compounds of formula (I) may be used in the absence of other chemotherapeutic agents. The compounds may be in the form of the (+) enantiomer.

In another embodiment the invention provides a method for treating brain cancer in a subject in need thereof, the method comprising administration to the subject of a therapeutically effective amount of a compound of the formula (I). The brain cancer may be glioma, for example glioblastoma, DIPG or medulloblastoma. The brain cancer may be adult or paediatric. The cancer may be a cancer that has recurred. The compound of formula (I) may be any combination of one or more of compounds 1 to 41. The compound of formula (I) may be selected from compounds 1 to 14 and 32-41, or alternatively the compound of formula (I) may be selected from compounds 1 to 14 and 32-40, or alternatively may be selected from compounds 1 to 14, or alternatively may be selected from compounds 2, 6, 9 and 36, or alternatively may be selected from compounds 2, 6, 9 and 13, or alternatively may be selected from compounds 2, 6 and 9, or alternatively may be selected from compounds 2, 6, 9 and 13, or alternatively may be selected from compounds 2 and 9. The compound of formula (I) may be compound 9. The compounds of formula (I) may be used in the absence of other chemotherapeutic agents. The glioma may be TMZ-resistant or susceptible to TMZ. The compounds may be in the form of the (+) enantiomer.

In still a further embodiment the invention provides a method for treating prostate cancer in a subject in need thereof, the method comprising administration to the subject of a therapeutically effective amount of a compound of the formula (I). The compound of formula (I) may be any combination of one or more of compounds 1 to 41. The compound of formula (I) may be selected from compounds 2, 6, 9, 19-22, 24 and 32 to 41, or alternatively may be selected from compounds 2, 6, 9, 19-22, 24 and 32 to 40. The compound of formula (I) may be selected from compounds 33 to 41 or from compounds 33 to 40. The compound of formula (I) may be compound 33 or 36. The compound of formula (I) may be compound 36. The compounds of formula (I) may be used in the absence of other chemotherapeutic agents. The compounds may be in the form of the (+) enantiomer. The compound of formula (I) may be administered rectally.

In still a further embodiment the invention provides a method for treating neuroblastoma in a subject in need thereof, the method comprising administration to the subject of a therapeutically effective amount of a compound of the formula (I). The compound of formula (I) may be any combination of one or more of compounds 1 to 41. The compound of formula (I) may be selected from compounds 2, 6, 9, 19-22, 24 and 32 to 41, or alternatively may be selected from compounds 2, 6, 9, 19-22, 24 and 32 to 40. The compound of formula (I) may be compound 9 or compound 36. The neuroblastoma may be paediatric neuroblastoma. The compounds of formula (I) may be used in the absence of other chemotherapeutic agents. The compounds may be in the form of the (+) enantiomer.

In still a further embodiment the invention provides a method for treating melanoma in a subject in need thereof, the method comprising administration to the subject of a therapeutically effective amount of a compound of the formula (I). The compound of formula (I) may be any combination of one or more of compounds 1 to 41. The compound of formula (I) may be selected from compounds 2, 6, 9, 19-22, 24 and 32 to 41, or alternatively may be selected from compounds 2, 6, 9, 19-22, 24 and 32 to 40. The compound of formula (I) may be compound 9. The compounds of formula (I) may be used in the absence of other chemotherapeutic agents. The compounds may be in the form of the (+) enantiomer.

In yet another embodiment the invention provides a method for treating malignant ascites in a subject in need thereof, the method comprising administration to the subject of a therapeutically effective amount of a compound of the formula (I). The compound of formula (I) may be any combination of one or more of compounds 1 to 41. The compound of formula (I) may be selected from compounds 2, 6, 9, 19-22, 24 and 32 to 41, or alternatively may be selected from compounds 2, 6, 9, 19-22, 24 and 32 to 40. The compound of formula (I) may be compound 2 or compound 9. The compound of formula (I) may be compound 2. The compounds of formula (I) may be used in the absence of other chemotherapeutic agents. The compounds may be in the form of the (+) enantiomer.

In another embodiment the invention provides a method for treating ovarian cancer peritoneal cancer, malignant ascites, uterine cancer, pancreatic cancer, gastric cancer, colorectal cancer, liver cancer, breast cancer, lung cancer or prostate cancer, in a subject in need thereof, the method comprising administration to the subject of a therapeutically effective amount of compound 2. The compound may be used in the absence of other chemotherapeutic agents. The compound may be in the form of the (+) enantiomer.

In another embodiment the invention provides a method for treating brain cancer, neuroblastoma, melanoma, ovarian cancer, pancreatic cancer, lung cancer, liver cancer, colorectal cancer or prostate cancer, in a subject in need thereof, the method comprising administration to the subject of a therapeutically effective amount of compound 9. The brain cancer may be glioma, for example, DIPG. The compound may be used in the absence of other chemotherapeutic agents. The compound may be in the form of the (+) enantiomer.

In another embodiment the invention provides a method for treating prostate cancer, brain cancer, lung cancer, liver cancer, breast cancer, melanoma, pancreatic cancer, ovarian cancer or colorectal cancer, in a subject in need thereof, the method comprising administration to the subject of a therapeutically effective amount of compound 36. The brain cancer may be glioma, for example, DIPG. The compound may be used in the absence of other chemotherapeutic agents. The compound may be in the form of the (+) enantiomer.

In another embodiment the invention provides a method for treating liver cancer in a subject in need thereof, the method comprising administration to the subject of a therapeutically effective amount of compound 20 or compound 33. The compounds may be used in the absence of other chemotherapeutic agents. The compounds may be in the form of the (+) enantiomer.

Those skilled in the art will recognise that compounds and pharmaceutical compositions of the present invention may be administered via any route which delivers an effective amount of the compounds to the tissue or site to be treated. In general, the compounds and compositions may be administered by the parenteral (for example intravenous, intraspinal, subcutaneous or intramuscular), oral or topical route. Administration may be systemic, regional or local. In one embodiment administration may be rectal.

The particular route of administration to be used in any given circumstance will depend on a number of factors, including the nature of the cancer to be treated, the severity and extent of the cancer, the required dosage of the particular compound to be delivered and the potential side-effects of the compound.

In general, suitable compositions may be prepared according to methods that are known to those of ordinary skill in the art and may include pharmaceutically acceptable carriers, diluents and/or excipients. The carriers, diluents and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil or coconut oil; silicone oils, including polysiloxanes, such as methyl polysiloxane, phenyl polysiloxane and methylphenyl polysiloxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; Cremaphor; cyclodextrins; lower alkanols, for example ethanol or il-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia and petroleum jelly. Typically, the carrier or carriers will form from 10% to 99.9% by weight of the compositions.

Pharmaceutical compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include cyclodextrins (for example Captisol®) Cremaphor, Ringer's solution, isotonic saline, phosphate buffered saline, ethanol and 1,2 propylene glycol. To aid injection and delivery, the compounds may also be added to PEG and non-PEGylated liposomes or micelles with specific targeting tags attached to PEG moieties, such as the RGD peptide or glutathione, for aiding passage across the blood brain barrier.

Some examples of suitable carriers, diluents, excipients and adjuvants for oral use include cyclodextrins. Cremaphor, peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate that delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharin. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E. alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethylcellulose, polyvinylpyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

Topical formulations may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C. to 100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisteriser such as glycerol, or oil such as olive oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol, such as propylene glycol or macrogols.

The composition may incorporate any suitable surfactant such as an anionic, cationic or non-ionic surfactant, such as sorbitan esters or polyoxyethylene derivatives thereof. Suspending agents such as natural gums, cellulose derivatives or inorganic materials such as silicaceous silicas, and other ingredients such a lanolin, may also be included.

In some embodiments the compositions are administered in the form of suppositories suitable for rectal administration of the compounds of formula (I). These compositions are prepared by mixing the compound of formula (I) with a suitable non-irritating excipient which is solid at ordinary temperatures but liquid at the rectal temperature and will therefore melt in the rectum to release the compound of formula (I). Such materials include cocoa butter, glycerinated gelatin, hydrogenated vegetable oils, mixtures of polyethylene glycols of various molecular weights and fatty acid esters of polyethylene glycol.

The compositions may also be administered or delivered to target cells in the form of liposomes. Liposomes are generally derived from phospholipids or other lipid substances and are formed by mono- or multi-lamellar hydrated liquid crystals that are dispersed in an aqueous medium. Specific examples of liposomes used in administering or delivering a composition to target cells are synthetic cholesterol (Sigma), the phospholipid 1,2-distearoyl-sn-glycero-3-phosphocholine (DSPC); Avanti Polar Lipids), the PEG lipid 3-N-[(-methoxy poly(ethylene glycol)2000)carbamoyl]-1,2-dimyrestyloxy-propylamine (PEG-cDMA), and the cationic lipid 1,2-di-o-octadecenyl-3-(N,N-dimethyl)aminopropane (DODMA) or 1,2-dilinoleyloxy-3-(N,N-dimethyl)aminopropane (DLinDMA) in the molar ratios 55:20:10:15 or 48:20:2:30, respectively, PEG-cDMA, DODMA and DLinDMA. The liposome may be contructed from 1,2-distearoyl-sn-glycero-3-phosphoethanolamine-N-[methoxy(polyethylene glycol)-2000] (DSPE PEG2000) and phosphatidylcholine derived from soy and hydrogenated between 50-100%, for example Soy PC-75 or Soy PC-100. Differing MW PEG's may be used and covalently bound with various specific targeting agents such as glutathione, RGD peptides or other recognized liposome targeting agents. Any non-toxic, physiologically acceptable and metabolisable lipid capable of forming liposomes can be used. The compositions in liposome form may contain stablisers, preservatives, excipients and the like. The preferred lipids are the phospholipids and the phosphatidyl cholines (lecithins), both natural and synthetic. Methods to form liposomes are known in the art, and in relation to this, specific reference is made to: Prescott, Ed., *Methods in Cell Biology*, Volume XIV, Academic Press, New York, N.Y. (1976), p. 33 et seq., the contents of which is incorporated herein by reference.

The compositions may also be administered in the form of microparticles or nanoparticles. Biodegradable microparticles formed from polyactide (PLA), polylactide-co-glycolide (PLGA), and epsilon-caprolactone (ε-caprlactone) have been extensively used as drug carriers to increase plasma half life and thereby prolong efficacy (R. Kumar, M., 2000, *J. Pharm. Pharmaceut. Sci.* 3(2) 234-258). Microparticles have been formulated for the delivery of a range of drug candidates including vaccines, antibiotics, and DNA. Moreover, these formulations have been developed for various delivery routes including parenteral subcutaneous injection, intravenous injection and inhalation.

The compositions may incorporate a controlled release matrix that is composed of sucrose acetate isobutyrate (SAIB) and an organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester. SAIB does not crystallise but exists as a clear viscous liquid. Mixing SAIB with a pharmaceutically acceptable organic solvent, such as ethanol or benzyl alcohol decreases the viscosity of the mixture sufficiently to allow for injection. An active pharmaceutical ingredient may be added to the SAIB delivery vehicle to form SAIB solution or suspension formulations. When the formulation is injected subcutaneously, the solvent differs from the matrix allowing the SAIB-drug or SAIB-drug-polymer mixtures to set up as an in situ forming depot.

For the purposes of the present invention compounds and compositions may be administered to subjects either therapeutically or preventively. In a therapeutic application compositions are administered to a patient already suffering from cancer in an amount sufficient to cure or at least partially arrest the cancer and its complications. The composition should provide a quantity of the compound or agent sufficient to effectively treat the subject.

The therapeutically effective amount for any particular subject will depend upon a variety of factors including: the cancer being treated and the severity thereof; the activity of the compound administered; the composition in which the compound is present; the age, body weight, general health, sex and diet of the subject; the time of administration; the route of administration; the rate of sequestration of the compound; the duration of the treatment; drugs used in combination or coincidental with the compound, together with other related factors well known in medicine.

One skilled in the art would be able, by routine experimentation, to determine an effective, non-toxic amount of a compound that would be required to treat or prevent a particular cancer.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours: about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would be for the duration of the disease state.

Further, it will be apparent to one of ordinary skill in the art that the optimal quantity and spacing of individual dosages will be determined by the nature and extent of the cancer being treated, the form, route and site of administration, and the nature of the particular individual being treated. Also, such optimum conditions can be determined by conventional techniques.

The compounds of formula (I) may be used alone in the treatment of cancer, or alternatively in combination with radiotherapy and/or surgery and/or other therapeutic agents, for example chemotherapeutic agents and immunostimulatory agents, as part of a combination therapy. The compounds of formula (I) may sensitise undifferentiated cancer cells to other chemotherapeutic agents and/or radiotherapy.

The terms "combination therapy" and "adjunct therapy" are intended to embrace administration of multiple therapeutic agents in a sequential manner in a regimen that will provide beneficial effects and is intended to embrace administration of these agents in either a single formulation or in separate formulations.

Combination therapy may involve the active agents being administered together, sequentially, or spaced apart as appropriate in each case. Combinations of active agents including compounds of the invention may be synergistic.

The co-administration of compounds of the formula (I) with other therapeutic agent(s) may be effected by a compound of the formula (I) being in the same unit dose form as the other therapeutic agent(s), or the compound of the formula (I) and the other therapeutic agent(s) may be present in individual and discrete unit dosage forms that are administered sequentially, at the same, or at a similar time. Sequential administration may be in any order as required, and may require an ongoing physiological effect of the first or initial agent to be current when the second or later agent is administered, especially where a cumulative or synergistic effect is desired. When administered separately, it may be preferred for the compound of formula (I) and the other agent to be administered by the same route of administration, although it is not necessary for this to be so.

In accordance with various embodiments of the present invention one or more compounds of formula (I) may be included in combination therapy with surgery and/or radiotherapy and/or one or more chemotherapeutic agents.

There are large numbers of chemotherapeutic agents that are currently in use, in clinical evaluation and in pre-clinical development, which could be selected for treatment of cancers in combination with compounds of the formula (I). Such agents fall into several major categories, namely, antibiotic-type agents, alkylating agents, anti-metabolite agents, hormonal agents, immunological agents, interferon-type agents and a category of miscellaneous agents. Alternatively, other chemotherapeutic agents, such as metallomatrix proteases (MMP) inhibitors may be used. Suitable agents which may be used in combination therapies include those listed, for example, in the Merck Index, *An Encyclopaedia of Chemicals, Drugs and Biologicals,* 12th Ed., 1996, the entire contents of which are incorporated herein by reference.

When used in the treatment of solid tumours compounds of the formula (I) may be administered with one or more of the following chemotherapeutic agents: adriamycin, taxol, docetaxel, fluorouracil, melphalan, cisplatin, alpha interferon, COMP (cyclophosphamide, vincristine, methotrexate and prednisone), etoposide, mBACOD (methotrexate, bleomycin, doxorubicin, cyclophosphamide, vincristine and dexamethasone), PROMACE/MOPP (prednisone, methotrexate (w/leucovin rescue), doxorubicin, cyclophosphamide, taxo(, etoposide/mechlorethamine, vincristine, prednisone and procarbazine), vincristine, vinblastine, angioinhibins. TNP 470, pentosan polysulfate, platelet factor 4, angiostatin, LM 609, SU 101, CM 101, Techgalan, thalidomide, SP-PG and the like.

The present invention is further described below by reference to the following non-limiting examples.

EXAMPLES

Example 1

Synthesis of Compounds of Formula (I)

Representative compounds of the formula (I) were prepared as follows.

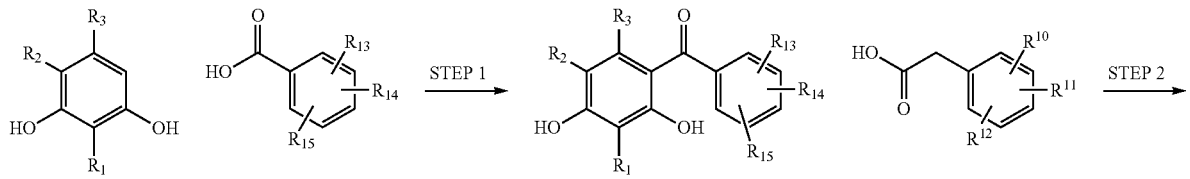

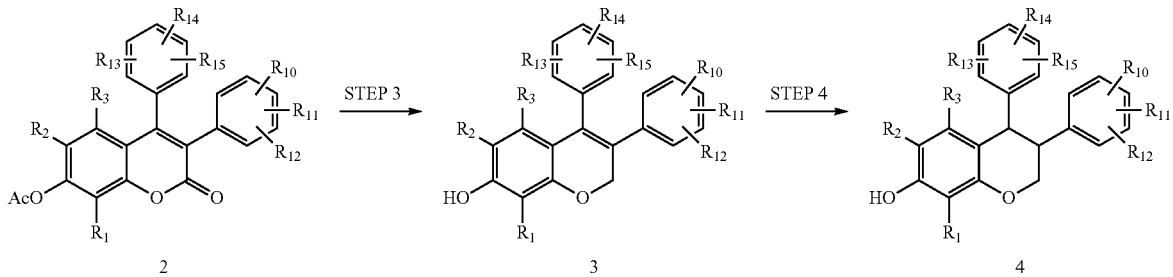

1a $R_1$ = Me, $R_2$, $R_3$ = H, $R_{13}$, $R_{15}$ = H, $R_{14}$ = OH
1b $R_1$ $R_2$, $R_3$, $R_{15}$ = H, $R_{13}$ = F, $R_{14}$ = OH
1c $R_1$ = Me, $R_2$, $R_3$ $R_{15}$ = H, $R_{13}$ = F, $R_{14}$ = OH
1d $R_1$, $R_2$, $R_3$, $R_{13}$, $R_{15}$ = Me, $R_{14}$ = OMe
1e $R_1$ = Me, $R_2$, $R_3$ = H, $R_{13}$, $R_{15}$ = F, $R_{14}$ = OH
1f $R_1$ = iPr, $R_2$, $R_3$, $R_{15}$ = H, $R_{13}$ = F, $R_{14}$ = OH
1g $R_1$, $R_3$, $R_{15}$ = H, $R_2$ = Et, $R_{13}$ = F, $R_{14}$ = OH
1h $R_1$ = Me, $R_2$, $R_3$, $R_{15}$ = H, $R_{13}$, $R_{14}$ = -OCH$_2$O-
1i $R_1$ = Me, $R_2$, $R_3$ = H, $R_{13}$, $R_{15}$ = H, $R_{14}$ = NH$_2$

1j $R_1$ = Me, $R_2$, $R_3$ = H, $R_{13}$, $R_{15}$ = H. $R_{14}$ = NHAc
1k $R_1$ = Me, $R_2$ = Et, $R_3$, $R_{13}$, $R_{15}$ = H, $R_{14}$ = OH
1l $R_1$ = Et, $R_2$, $R_3$, $R_{13}$, $R_{15}$ = H $R_{14}$ = OH
1m $R_2$ = Me, $R_1$, $R_3$, $R_{13}$, $R_{15}$ = H, $R_{14}$ = OH
1n $R_3$, $R_{15}$ = F, $R_1$, $R_2$, $R_{15}$ = H, $R_{14}$, = OH
1o $R_2$ = Cl, $R_1$, $R_3$, $R_{15}$ = H, $R_{13}$ = F, $R_{14}$ = OH
1p $R_1$ = Me, $R_2$, $R_3$, $R_{15}$ = H, $R_{13}$ = Cl, $R_{14}$ = OH
1q $R_1$ = Me, $R_2$ = Et, $R_3$, $R_{15}$ = H, $R_{13}$ = F, $R_{14}$ = OH
1r $R_1$ = Me, $R_2$ = Et, $R_3$, $R_{15}$ = H, $R_{13}$ = Me, $R_{14}$ = OH
1s $R_1$ = Me, $R_2$ = Et, $R_3$, $R_{15}$ = H $R_{13}$ = Me, $R_{14}$ = OH
1t $R_1$ = Me, $R_2$ = Et, $R_3$, $R_{15}$ = H $R_{13}$ = F, $R_{14}$ = OH a $R_1$ = Me, $R_{10}$, $R_{11}$, $R_{12}$ = OMe, $R_2$, $R_3$, $R_{13}$, $R_{15}$ = H, $R_{14}$ = OH
b $R_1$ = Me, $R_{10}$, $R_{12}$ = OMe, $R_{11}$, $R_{14}$ = OH, $R_2$, $R_3$, $R_{15}$ = H
c $R_1$ = Me, $R_{10}$, $R_{12}$ = t-Bu, $R_{11}$, $R_{14}$ = OH, $R_2$, $R_3$, $R_{13}$, $R_{15}$ = H
d $R_1$ = Me. $R_{10}$, $R_{11}$, $R_{12}$ = F, $R_2$, $R_3$, $R_{13}$, $R_{15}$ = H, $R_{14}$ = OH
e $R_1$, $R_2$, $R_3$, $R_{15}$ = H, $R_{10}$, $R_{11}$, $R_{12}$, $R_{13}$ = F, $R_{14}$ = OH
f $R_1$, $R_2$, $R_3$, $R_{15}$ = H, $R_{10}$, $R_{12}$ = OMe, $R_{11}$, $R_{14}$ = OH, $R_{13}$ = F
g $R_1$, $R_2$, $R_3$, $R_{15}$ = H, $R_{10}$, $R_{11}$, $R_{12}$ = OMe, $R_{13}$ = F, $R_{14}$ = OH
h $R_1$ = Me, $R_{10}$, $R_{11}$, $R_{12}$, $R_{13}$ = F, $R_{14}$ = OH, $R_2$, $R_3$, $R_{15}$ = H
i $R_1$ = Me, $R_{10}$, $R_{12}$ = OMe, $R_{11}$, $R_{14}$ = OH, $R_{13}$ = F, $R_2$, $R_3$, $R_{15}$ = H
j $R_1$ = Me, $R_{10}$, $R_{11}$, $R_{12}$ = OMe, $R_{13}$ = F, $R_{14}$ = OH, $R_2$, $R_3$, $R_{15}$ = H
k $R_1$, $R_{13}$, $R_{15}$ = Me, $R_{10}$, $R_{12}$, $R_{14}$ = OMe, $R_2$, $R_3$, $R_{11}$ = OH
l $R_1$, $R_{13}$, $R_{15}$ = Me, $R_{10}$, $R_{11}$, $R_{12}$, $R_{14}$ = OMe, $R_2$, $R_3$ = H
m $R_1$ = Me, $R_{10}$, $R_{12}$ = OMe, $R_{11}$, $R_{14}$ = OH, $R_{13}$, $R_{15}$ = F, $R_2$, $R_3$ = H
n $R_1$ = Me, $R_{10}$, $R_{11}$, $R_{12}$ = OMe, $R_{13}$, $R_{15}$ = F, $R_{14}$ = OH, $R_2$, $R_3$ = H o $R_1$ = iPr, $R_2$, $R_3$, $R_{15}$ = H, $R_{13}$ = F, $R_{10}$, $R_{12}$ = OMe, $R_{11}$, $R_{14}$ = OH
p $R_1$, $R_3$, $R_{15}$ = H, $R_2$ = Et, $R_{13}$ = F, $R_{10}$, $R_{12}$ = OMe, $R_{11}$, $R_{14}$ = OH
q $R_1$ = Me, $R_2$, $R_3$, $R_{15}$ = H, $R_{10}$, $R_{12}$ = OMe, $R_{11}$ = OH, $R_{13}$, $R_{14}$ = -OCH$_2$O-
r $R_1$ = Me, $R_2$, $R_3$ = H, $R_{13}$, $R_{15}$ = H, $R_{10}$, $R_{12}$ = OMe, $R_{11}$ = OH, $R_{14}$ = NH$_2$
s $R_1$ = Me, $R_2$, $R_3$ = H, $R_{13}$, $R_{15}$ = H, $R_{10}$, $R_{12}$ = OMe, $R_{11}$ = OH, $R_{14}$ = NHEt
t $R_1$ = Me, $R_2$ =Et, $R_3$, $R_{13}$, $R_{15}$ = H, $R_{10}$, $R_{12}$ = OMe, $R_{11}$ = OH, $R_{14}$ = OH
u $R_1$ = Et, $R_2$, $R_3$, $R_{13}$, $R_{15}$ = H, $R_{10}$, $R_{12}$ = OMe, $R_{11}$ = OH, $R_{14}$ = OH
v $R_2$ = Me, $R_1$, $R_3$, $R_{13}$, $R_{15}$ = H, $R_{10}$, $R_{12}$ = OMe, $R_{11}$ = OH, $R_{14}$ = OH
w $R_3$, $R_{13}$ = F, $R_1$, $R_2$, $R_{15}$ = H, $R_{10}$, $R_{12}$ = OMe, $R_{11}$ = OH, $R_{14}$ = OH
x $R_2$ = Cl, $R_1$, $R_3$, $R_{15}$ = H, $R_{13}$ = F, $R_{10}$, $R_{12}$ = OMe, $R_{11}$ = OH, $R_{14}$ = OH
y $R_1$ = Me, $R_2$, $R_3$, $R_{15}$ = H, $R_{13}$ = Cl, $R_{10}$, $R_{12}$ = OMe, $R_{11}$ = OH, $R_{14}$ = OH
z $R_1$ = Me, $R_2$ = Et, $R_3$, $R_{15}$ = H, $R_{10}$, $R_{13}$ = OMe, $R_{13}$ = F, $R_{11}$ = OH, $R_{14}$ = OH
aa $R_1$ = Me, $R_2$ = Et, $R_3$, $R_{15}$ = H, $R_{10}$, $R_{13}$ = OMe, $R_{13}$ = Me, $R_{11}$ = OH, $R_{14}$ = OH
bb $R_1$ = Me, $R_2$ = Et, $R_3$, $R_{15}$ = H, $R_{10}$, $R_{13}$ = Me, $R_{13}$ = F, $R_{11}$ = OH, $R_{14}$ = OH
cc $R_1$ = Me, $R_2$ = Et, $R_3$, $R_{15}$ = H, $R_{10}$, $R_{13}$ = OMe, $R_{13}$ = Me, $R_{11}$ = OH, $R_{14}$ = OH
dd $R_1$ = Me, $R_2$ = Et, $R_3$, $R_{15}$ = H, $R_{10}$, $R_{13}$ = Me, $R_{13}$ = F, $R_{11}$ = OH, $R_{14}$ = OH

Step 1. ZnCl$_2$, POCl$_3$, 70° C., 2 h; Step 2. DiPEA, Ac$_2$O, 135° C., 18 h. Step 3. THF, BH$_3$,Me$_2$S in THF, 35° C., 18 h; Step 4. H$_2$, Pd/C, EtOH, 3 bar, 40° C., 18 h.

Step 1. (2,4-Dihydroxy-3-methylphenyl)(4-hydroxyphenyl)methanone (1-1a)

2-Methylresorcinol (50 g, 1 eq.), 4-hydroxybenzoic acid (55.5 g, 1 eq.), zinc chloride (120 g, 2.2 eq) and POCl$_3$ (550 mL) was added to a flask under N$_2$ and set stirring. The mixture was heated to 70° C. for 2 hrs, cooled to r.t and poured onto ice/water (4 L) keeping the temperature at <30° C. The solid was filtered, washing with water (3×500 mL). The damp solid was then recrystallised from IMS (250 mL) and dried to afford the product as an orange solid 85 g (87%). $^1$H NMR (300 MHz, DMSO-d$_6$) δ 12.91 (s, 1H), 10.59 (s, 1H), 10.30 (s, 1H), 7.28 (d, J=8.9 Hz, 2H), 7.18 (d, J=7.8 Hz, 1H), 6.46 (d, J=8.9 Hz, 2H), 6.24 (d, J=7.8 Hz, 1H), 2.02 (s, 3H).

Other analogues prepared by this method:

(2,4-Dihydroxyphenyl)(3-fluoro-4-hydroxyphenyl)methanone (1-1b) (47%). $^1$H NMR (300 MHz, DMSO-d$_6$) δ 11.90 (bs, 1H), 7.51-7.32 (m, 3H), 7.09 (t, J=8.5 Hz, 1H), 6.45-6.33 (m, 2H).

(2,4-Dihydroxy-3-methylphenyl)(3-fluoro-4-hydroxyphenyl)methanone (1-1c) (41%). $^1$H NMR (400 MHz, DMSO-d$_6$) δ 12.72 (s, 1H), 10.76 (s, 1H), 10.65 (s, 1H), 7.43 (dd, J=1.96, 11.74 Hz, 1H), 7.33 (d, J=9.00 Hz, 2H), 7.06 (t, J=8.41 Hz, 1H), 6.45 (d, J=9.00 Hz, 1H), 1.99 (s, 3H).

(2,4-Dihydroxy-3-methylphenyl)(4-methoxy-3,5-dimethylphenyl)methanone (1-1d) (63%). $^1$H NMR (300 MHz, DMSO-d$_6$) δ 12.89 (s, 1H), 10.67 (s, 1H), 10.15 (s, 1H), 7.38-7.15 (m, 3H), 6.52-6.43 (m, 1H), 3.72 (s, 3H), 2.28 (s, 6H).

(3,5-Difluoro-4-hydroxyphenyl)(2,4-dihydroxy-3-methylphenyl)methanone (1-1e) (43%). $^1$H NMR (300 MHz, DMSO-d$_6$) δ 12.61 (s, 1H), 10.84 (bs, 1H), 9.70 (bs, 1H), 7.23-7.10 (m, 2H), 6.98-6.85 (m, 1H), 2.20 (s, 3H).

(2,4-Dihydroxy-3-i-propyiphenyl)(3-fluoro-4-hydroxyphenyl)methanone (1 -1f) (18%). $^1$H NMR (300 MHz, DMSO-d$_6$) δ 12.88 (bs, 1H), 7.62 (d, J=8.9 Hz, 2H), 7.31 (d, J=8.4 Hz, 1H), 7.12 (d, J=8.9 Hz, 2H), 6.47 (d, J=8.4 Hz, 1H), 1.95 (m, 2H), 1.65 (m, 2H), 1.2 (t, J=9.1 Hz, 3H).

(2,4-Dihydroxy-5-ethylphenyl)(3-fluoro-4-hydroxyphenyl)methanone (1-1 g) (77%) $^1$H NMR (300 MHz, DMSO-d$_6$) δ 7.41 (d, J=1.2 Hz, 1H), 7.32 (d, J=1.4 Hz, 1H), 7.22 (dd, J=1.2, 8.2 Hz), 7.08 (d, J=1.2 Hz, 1H), 7.00 (d, J=8.1 Hz, 1H), 2.51 (q, J=9.1 Hz, 2H), 1.22 (t, J=9.2 Hz, 3H).

(2,4-Dihydroxy-3-methylphenyl)(3-4-methylenedioxyphenyl)methanone (1-1h) (22%) $^1$H NMR (300 MHz, DMSO-d$_6$) δ 12.65 (br s, 1H), 9.87 (br s, 1H), 7.38 (d, J=8.2 Hz, 1H), 7.25 (m, 2H), 7.05 (d, J=8.3 Hz, 1H), 6.43 (d, J=8.2 Hz, 1H), 6.06 (s, 2H), 2.02 (s, 3H).

(2,4-Dihydroxy-3-methylphenyl)(4-nitrophenyl)methanone (1-1i) (38%) $^1$H NMR (300 MHz, DMSO-d$_6$) δ 12.96 (br s, 1H), 8.33 (d, J=8.7 Hz, 2H), 7.97 (d, J=8.8 Hz, 2H), 7.09 (d, J=8.12 Hz, 1H), 6.90 (d, J=8.2 Hz, 1H), 2.05 (s, 3H).

(2,4-Dihydroxy-3-methylphenyl)(4-acetamidephenyl)methanone (1-1j) (38%) $^1$H NMR (300 MHz, DMSO-d$_6$) δ 13.21 (br s, 1H), 9.66 (br s, 1H), 7.88 (d, J=8.1 Hz, 2H), 7.44 (d, J=8.4 Hz, 1H), 6.56 (d, J=8.2 Hz, 1H), 6.50 (d, J=8.3 Hz, 2H), 6.10 (s, 1H), 2.09 (s, 3H), 2.02 (s, 3H).

(2,4-Dihydroxy-5-ethyl-3-methylphenyl)(4-hydroxypheny)methanone (1-1k) (42%) $^1$H NMR (300 MHz, DMSO-d$_6$) δ 13.55 (s, 1H), 11.20 (br, 1H), 10.90 (br, 1H), 7.44 (q, J=8.2 Hz, 2H), 7.11 (s, 1H 6.99 (d, J=8.2 Hz, 1H), 3.45 (q, J=7.9 Hz, 2H), 2.2 (s, 3H), 1.34(t, J=8.0 Hz, 3H).

(2,4-Dihydroxy-3-ethylphenyl)(4-hydroxyphenyl)methanone (1-1l) $^1$H NMR (300 MHz, DMSO-d$_6$) δ 12.2 (s, 1H), 7.43 (d, J=8.3 Hz, 1H), 7.35 (d, J=8.4 Hz, 1H), 7.11 (d, J=8.2 Hz, 1H), 6.55 (d, J=8.4 Hz, 2H), 2.65 (m, 2H), 1.04 (t, J=7.8 Hz, 3H).

(2,4-Dihydroxy-5-methylphenyl)(4-hydroxyphenyl)methanone (1-1m) $^1$H NMR (300 MHz, DMSO-d$_6$) δ 11.90 (s, 1H), 10.90-95 (br, 2H), 7.40 (d, J=8.3 Hz, 2H), 7.33 (s, 1H), 7.11 (d, J=8.3 Hz, 2H), 6.33 (s, 1H), 2.05 (s, 3H).

(2,4-Dihydroxy-5-flourophenyl)(3-fluoro-4-hydroxyphenyl)methanone (1-1n) $^1$H NMR (300 MHz, DMSO-d$_6$) δ 7.99 (m, 1H), 7.55-7.35 (m, 3H), 7.05 (m, 1H), 6.55 (s, 1H).

(5-chloro-2,4-Dihydroxyphenyl)(3-fluoro-4-hydroxyphenyl)methanone (1-1o) $^1$H NMR (300 MHz, DMSO-d$_6$) δ 11.11 (s, 1H), 7.89 (m, 1H), 7.55-45 (m, 2H), 7.11 (s, 1H), 6.5 (s, 1H).

(2,4-Dihydroxy-3-methylphenyl)(3-chloro-4-hydroxyphenyl)methanone (1-1p) $^1$H NMR (300 MHz, DMSO-d$_6$) δ 12.91 (s, 1H), 11.11 (br, 1H), 10.65 (br, 1H), 7.90 (s, 1H), 7.55 (d, J=8.2 Hz, 1H), 7.36 (d, J=8.3 Hz, 1H), 7.11 (d, J=8.3 Hz, 1H), 6.23 (d, J=8.2 Hz, 1H) 2.05 (s, 3H).

(2,4-Dihydroxy-5-ethyl-3-methylphenyl)(3-fluoro-4-hydroxyphenyl)methanone (1-1 q) (42%) $^1$H NMR (300 MHz, DMSO-d$_6$) δ 13.55 (s, 1H), 11.20 (br, 1H), 10.90 (br, 1H), 7.55-7.45 (m, 2H), 7.11 (brs, 1H), 7.01 (s, 1H), 3.45 (q, J=7.9 Hz, 2H), 2.2 (s, 3H), 1.34 (t, J=8.0 Hz, 3H).

(2,4-Dihydroxy-5-ethyl-3-methylphenyl)(3-methyl-4-hydroxyphenyl)methanone (1-1r) (41%) $^1$H NMR (300 MHz, DMSO-d$_6$) δ 9.55 (s, 1H), 8.20 (br, 1H), 7.90 (br, 1H), 6.65 (d, J=7.1 Hz, 1H), 6.60 (dd, J=7.1, 2.1 Hz, 1H), 6.45 (s, 1H), 6.35 (d, J=2.1 Hz, 1H), 3.15 (q, J=7.9 Hz, 2H), 2.2 (s, 3H), 1.14 (t, J=8.0 Hz, 3H).

(2,4-Dihydroxy-5-ethyl-3-methylphenyl)(2-methyl-4-hydroxyphenyl)methanone (1-1s) (32%) $^1$H NMR (300 MHz, DMSO-d$_6$) δ 9.59 (s, 1H), 8.60 (br, 1H), 7.95 (br, 1H), 6.68 (d, J=7.1 Hz, 1H), 6.60 (s, 1H), 6.56 (d, J=7.Hz, 1H), 6.35 (dd, J=6.9, 2.1 Hz, 1H), 3.25 (q, J=7.8 Hz, 2H), 2.2 (s, 3H), 1.24 (t, J=8.0 Hz, 3H).

(2,4-Dihydroxy-5-ethyl-3-methylphenyl)(2-fluoro-4-hydroxyphenyl)methanone (1-1t) (38%) $^1$H NMR (300 MHz, DMSO-d$_6$) δ 10.9 (s, 1H), 9.16 (br, 1H), 7.95 (br, 1H), 6.78 (dd J=6.9, 6.2 Hz, 1H), 6.62 (brd, J=7.1 Hz, 1H), 6.56 (s, 1H), 6.45 (brd, J=6.9 Hz, 1H), 3.28 (q, J=7.8 Hz, 2H), 2.2 (s, 3H), 1.14 (t, J=8.0 Hz, 3H).

Step 2. 3-(4-Acetoxy-3,5-dimethoxyphenyl)-4-(4-acetoxyphenyl)-8-methyl-2-oxo-2H-chromen-7-yl acetate (1-2a)

(2,4-Dihydroxy-3-methylphenyl)(4-hydroxyphenyl)methanone (36.8 g, 1 eq.) and 3,5-dimethoxy-4-hydroxyphenylacetic acid (32 g, 1 eq.), was added to acetic anhydride (110 mL), with stirring the diisopropylethylamine (64.4 g, 4.5 eq.) was then added over 5 minutes. The reaction was heated to 130-140° C. for 18 hrs then cooled to room temperature and poured onto water (750 mL). The aqeous was extracted with DCM (2×750 mL), washed with water (500 mL), brine (300 mL), dried over MgSO$_4$, then stripped to afford a dark brown sticky solid. The crude material was treated with EtOAc (200 mL), stirred, heated to reflux and cooled, solid filtered off washed with ice cold EtOAc (50 mL) to give a pale yellow solid (66 g). The solid was treated 2×EtOAc (100 mL) stirring at r.t. for 30 min, filtered to give a white solid (62 g, 76%). $^1$H NMR (300 MHz, CDCl$_3$) δ 7.18-7.07 (m, 5H), 6.93 (d, J=8.3 Hz, 1H), 6.37 (s, 2H), 3.62 (s, 6H), 2.38 (s, 3H), 2.36 (s, 3H), 2.30 (s, 3H), 2.28 (s, 3H).

Other analogues prepared via this method:

4-(7-Acetoxy-8-methyl-2-oxo-3-(3,4,5-trimethoxyphenyl)-2H-chromen-4-yl)phenyl acetate (1-2b) (61%). $^1$H NMR (300 MHz, CDCl$_3$) δ 7.17-7.06 (m, 5H), 6.91 (d, J=8.3 Hz, 1H), 6.34 (s, 2H), 3.80 (s, 3H), 3.65 (s, 6H), 2.38 (s, 3H), 2.36 (s, 3H), 2.30 (s, 3H).

3-(4-Acetoxy-3,5-di-tert-butylphenyl)-4-(4-acetoxyphenyl)-8-methyl-2-oxo-2H-chromen-7-yl acetate (1-2c) (21%). $^1$H NMR (300 MHz, CDCl$_3$) δ 7.20-7.00 (m, 7H), 6.94-6.86 (m, 2H), 2.36 (s, 3H), 2.34 (s, 3H), 2.29 (s, 3H), 1.44 (s, 9H), 1.09 (s, 9H).

4-(7-Acetoxy-8-methyl-2-oxo-3-(3,4,5-trifluorophenyl)-2H-chromen-4-yl)phenyl acetate (1-2d) (20%). $^1$H NMR (300 MHz, CDCl$_3$) δ 7.18-7.08 (m, 5H), 7.01 (d, J=8.8 Hz, 1H), 6.80-6.71 (m, 2H), 2.38 (s, 3H), 2.36 (s, 3H), 2.33 (s, 3H).

4-(7-Acetoxy-2-oxo-3-(3,4,5-trifluorophenyl)-2H-chromen-4-yl)-2-fluorophenyl acetate (1-2e) (76%). $^1$H NMR (300 MHz, DMSO-d$_6$) δ 7.57-7.29 (m, 4H), 7.21-7.10 (m, 4H), 2.31 (s, 6H).

3-(4-Acetoxy-3,5-dimethoxyphenyl)-4-(4-acetoxy-3-fluorophenyl)-2-oxo-2H-chromen-7-yl acetate (1-2f) (68%). $^1$H NMR (300 MHz, CDCl$_3$) δ 7.31-7.20 (m, 2H), 7.17-7.10 (m, 1H), 7.07-6.98 (m, 2H), 6.94-6.88 (m, 1H), 6.38 (s, 2H), 3.64 (s, 6H), 2.36 (s, 3H), 2.34 (s, 3H), 2.29 (s, 3H).

4-(7-Acetoxy-2-oxo-3-(3,4,5-trimethoxyphenyl)-2H-chromen-4-yl)-2-fluorophenyl acetate (1-2 g) (50%). $^1$H NMR (300 MHz, CDCl$_3$) δ 7.32-7.22 (m, 2H), 7.18-7.05 (m, 1H), 7.08-6.90 (m, 3H), 6.33 (s, 2H), 3.72 (s, 3H), 3.69 (s, 6H), 2.38 (s, 6H).

4-(4-Acetoxy-3-fluorophenyl)-8-methyl-2-oxo-3-(3,4,5-trifluorophenyl)-2H-chromen-7-yl acetate (1-2h) (49%). $^1$H NMR (300 MHz, CDCl$_3$) δ 7.37-7.05 (m, 4H), 7.03-6.88 (m, 2H), 6.81-6.70 (m, 1H), 6.38 (s, 1H), 2.36 (bs, 9H).

3-(4-Acetoxy-3,5-dimethoxyphenyl)-4-(4-acetoxy-3-fluorophenyl)-8-methyl-2-oxo-2H-chromen-7-yl acetate (1-2i) (46%). $^1$H NMR (300 MHz, CDCl$_3$) δ 7.18-6.87 (m, 5H), 6.39 (s, 2H), 3.66 (s, 6H), 2.38 (s, 3H), 2.36 (s, 3H), 2.33 (s, 3H), 2.29 (s, 3H).

4-(4-Acetoxy-3-fluorophenyl)-8-methyl-2-oxo-3-(3,4,5-trimethoxyphenyl)-2H-chromen-7-yl acetate (1-2j) (49%). $^1$H NMR (300 MHz, CDCl$_3$) δ 7.16-6.89 (m, 5H), 6.34 (s, 2H), 3.82 (s, 3H), 3.68 (s, 6H), 2.38 (s, 3H), 2.34 (s, 3H), 2.31 (s, 3H).

3-(4-Acetoxy-3,5-dimethoxyphenyl)-4-(4-methoxy-3,5-dimethylphenyl)-8-methyl-2-oxo-2H-chromen-7-yl acetate (1-2k) (30%). $^1$H NMR (300 MHz, CDCl$_3$) δ 7.20 (d, J=8.4 Hz, 1H), 6.92 (d, J=8.4 Hz, 1H), 6.77 (s, 2H), 6.42 (s, 2H), 3.72 (s, 3H), 3.61 (s, 6H), 2.38 (s, 3H), 2.36 (s, 3H), 2.30 (s, 3H), 2.20 (s, 6H).

4-(4-Methoxy-3,5-dimethylphenyl)-8-methyl-2-oxo-3-(3,4,5-trimethoxyphenyl)-2H-chromen-7-yl acetate (1-2l) (34%). $^1$H NMR (300 MHz, CDCl$_3$) δ 7.15 (d, J=8.7 Hz, 1H), 6.90 (d, J=8.7 Hz, 1H), 6.76 (s, 2H), 6.38 (s, 2H), 3.80 (s, 3H), 3.71 (s, 3H), 3.66 (s, 6H), 2.39 (s, 3H), 2.37 (s, 3H), 2.30 (s, 3H), 2.20 (s, 6H).

4-(4-Acetoxy-3,5-difluorophenyl)-3-(4-acetoxy-3,5-dimethoxyphenyl)-8-methyl-2-oxo-2H-chromen-7-yl acetate (1-2m) (30%). $^1$H NMR (300 MHz, CDCl$_3$) δ 7.03-6.90 (m, 3H), 6.84-6.76 (m, 1H), 6.47 (s, 2H), 3.73 (s, 6H), 2.39 (s, 3H), 2.37 (s, 3H), 2.34 (s, 3H), 2.28 (s, 3H).

4-(4-Acetoxy-3,5-difluorophenyl)-8-methyl-2-oxo-3-(3,4,5-trimethoxyphenyl)-2H-chromen-7-yl acetate (1-2n) (22%). $^1$H NMR (300 MHz, CDCl$_3$) δ 7.03-6.77 (m, 4H), 6.40 (s, 2H), 3.77 (s, 3H), 3.71 (s, 6H), 2.38 (s, 3H), 2.36 (s, 3H), 2.34 (s, 3H).

3-(4-Acetoxy-3,5-dimethoxyphenyl)-4-(3-fluoro-4-acetoxyphenyl)-8-propyl-2-oxo-2H-chromen-7-yl acetate (1-2o) (34%). $^1$H NMR (300 MHz, CDCl$_3$) δ 7.18 (d, J=8.2 Hz, 2H), 7.15-09 (m, 2H), 6.87 (d, J=8.2 Hz, 2H), 6.82 (d, J=8.5 Hz, 1H), 6.36 (s, 2H), 3.73 (s, 6H), 2.75 (t, J=7.6 Hz, 2H), 2.13 (s, 3H), 2.10 (s, 3H), 2.05 (s, 3H), 1.65 (m, 1H), 1.06 (t, J=7.6 Hz, 3H).

3-(4-Acetoxy-3,5-dimethoxyphenyl)-4-(3-fluoro-4-acetoxyphenyl)-6-ethyl-2-oxo-2H-chromen-7-yl acetate (1-2p) (34%). $^1$H NMR (300 MHz, CDCl$_3$) δ 7.18 (s, 1H), 7.16 (m, 1H), 7.08 (s, 1H), 7.04 (dd, J=8.2, 1.5 Hz, 1H), 6.95 (dd, J=8.3, 2.5 Hz, 1H), 6.35 (s, 2H), 3.56 (s, 6H), 2.56 (q, J=7.6 Hz, 2H), 2.12 (s, 3H), 2.10 (s, 3H), 2.09 (s, 3H), 1.04 (t, J=7.7 Hz, 3H).

3-(4-Acetoxy-3,5-dimethoxyphenyl)-4-(3,4-methylenedioxyphenyl)-8-methyl-2-oxo-2H-chromen-7-yl acetate (1-2q) (75%). $^1$H NMR (300 MHz, CDCl$_3$) δ 7.20 (d, J=8.3 Hz, 1H), 6.96 (d, J=8.2 Hz, 1H), 6.75 (d, J=8.2 Hz, 1H), 6.56 (d, J=8.3 Hz, 1H), 6.51 (s, 1H), 6.34 (s, 2H), 5.96 (s, 1H), 5.91 (s, 1H), 3.58 (s, 6H), 2.25 (s, 3H), 2.20 (s, 3H), 1.65 (s, 3H).

3-(4-Acetoxy-3,5-dimethoxyphenyl)-4-(4-nitrophenyl)-8-methyl-2-oxo-2H-chromen-7-yl acetate (1-2r) (25%). $^1$H NMR (300 MHz, CDCl$_3$) δ 8.25 (d, J=8.6 Hz, 2H), 7.35 (d, J=8.4 Hz, 2H), 6.96 (m, 2H), 6.34 (s, 2H), 3.67 (s, 6H), 2.25 (s, 3H), 2.21 (s, 3H), 1.89 (s, 3H).

3-(4-Acetoxy-3,5-dimethoxyphenyl)-4-(4-ethylaminophenyl)-8-methyl-2-oxo-2H-chromen-7-yl acetate (1-2s) (45%). $^1$H NMR (300 MHz, CDCl$_3$) δ 7.51 (d, J=8.2 Hz, 2H), 7.17 (d, J=8.2 Hz, 1H), 7.09 (d, J=8.2 Hz, 2H), 6.87 (d, J=8.3 Hz, 1H), 6.43 (s, 2H), 3.61 (s, 6H), 2.42 (s, 3H), 2.25 (s, 3H), 2.12 (s, 3H), 1.96 (s, 3H).

3-(4-Acetoxy-3,5-dimethoxyphenyl)-4-(4-acetoxyphenyl)-6-ethyl-8-methyl4-2-oxo-2H-chromen-7-yl acetate (1-2t) (25%). $^1$H NMR (300 MHz, CDCl$_3$) δ 7.18 (d, J=82 Hz, 2H), 6.96 (s, 1H), 6.87 (d, J=8.3 Hz, 2H), 6.35 (s, 2H), 3.61 (s, 6H), 2.32 (q, J=7.2 Hz, 2H), 2.25 (s, 3H), 2.21 (s, 3H), 2.16 (s, 3H), 1.95 (s, 3H), 1.05 (t, J=7.2 Hz, 3H).

3-(4-Acetoxy-3,5-dimethoxyphenyl)-4-(4-acetoxyphenyl)-8-ethyl-2-oxo-2H-chromen-7-yl acetate (1-2u) (45%). $^1$H NMR (300 MHz, CDCl$_3$) δ 7.21 (d, J=8.2 Hz, 2H), 7.10 (d, J=8.4 Hz, 1H), 6.97 (d, J=8.3 Hz, 2H), 6.91 (d, J=8.4 Hz, 1H), 6.41 (s, 2H), 3.61 (s, 6H), 2.81 (q, J=7.2 Hz, 2H), 2.25 (s, 3H), 2.21 (s, 3H), 2.18 (s, 3H), 1.25 (t, J=7.1 Hz, 3H).

3-(4-Acetoxy-3,5-dimethoxyphenyl)-4-(4-acetoxyphenyl)-6-methyl-2-oxo-2H-chromen-7-yl acetate (1-2v) (55%). $^1$H NMR (300 MHz, CDCl$_3$) δ 7.21 (d, J=8.2 Hz, 2H), 7.18 (d, J=8.2 Hz, 2H), 7.07 (m, 1H), 6.88 (m,1H), 6.34 (s, 2H), 3.61 (s, 6H), 2.28 (s, 3H), 2.21 (s, 3H), 2.18 (s, 3H), 1.96 (s, 3H).

3-(4-Acetoxy-3,5-dimethoxyphenyl)-4-(4-acetoxy-3-fluorophenyl)-5-fluoro-2-oxo-2H-chromen-7-yl acetate (1-2w) (15%). $^1$H NMR (300 MHz, CDCl$_3$) δ 7.07-7.02 (m, 2H), 6.96-86 (m, 1H), 6.58 (s, 1H), 6.50 (s, 1H), 6.36 (s, 2H), 3.61 (s, 6H), 2.23 (s, 3H), 2.21 (s, 3H), 2.18 (s, 3H).

3-(4-Acetoxy-3,5-dimethoxyphenyl)-4-(4-acetoxyphenyl)-6-chloro-2-oxo-2H-chromen-7-yl acetate (1-2x) (45%). $^1$H NMR (300 MHz, CDCl$_3$) δ 7.21 (m, 2H), 7.18 (dd, J=1.4, 1.2 Hz, 1H), 7.02 (dd, J=1.2, 8.1 Hz, 1H), 6.96 (dd, J=1.3, 8.6 Hz, 1H), 6.41 (s, 2H), 3.61 (s, 6H), 2.45 (s, 3H), 2.35 (s, 3H), 2.21 (s, 3H).

3-(4-Acetoxy-3,5-dimethoxyphenyl)-4-(4-acetoxy-3-chlorophenyl)-8-methyl-2-oxo-2H-chromen-7-yl acetate (1-2y) (55%). $^1$H NMR (300 MHz, CDCl$_3$) δ 7.31 (s, 1H), 7.10 (m, 2H), 7.05-7.01 (m, 2H), 6.45 (s, 2H), 3.66 (s, 6H), 2.35 (s, 3H), 2.21 (s, 3H), 2.18 (s, 3H).

3-(4-Acetoxy-3, 5-dimethoxyphenyl)-4-(4-acetoxy-3-fluorophenyl)-6-ethyl-8-methyl-2-oxo-2H-chromen-7-yl acetate (1-2z) (35%). $^1$H NMR (300 MHz, CDCl$_3$) δ 7.07-7.02 (m, 2H), 6.96-88 (m, 1H), 6.86 (s, 1H), 6.35 (s, 2H), 3.61 (s, 6H), 2.32 (q, J=7.2 Hz, 2H), 2.25 (s, 3H), 2.21 (s, 3H), 2.16 (s, 3H), 1.95 (s, 3H), 1.05 (t, J=7.2 Hz, 3H).

3-(4-Acetoxy-3,5-dimethoxyphenyl)-4-(4-acetoxy-3-methylphenyl)-6-ethyl-8-methyl-2-oxo-2H-chromen-7-yl acetate (1-2aa) (38%). $^1$H NMR (300 MHz, CDCl$_3$) δ 6.68 (d, J=7.5 Hz, 1H), 6.65 (dd, J=7.1, 2.1 Hz, 1H), 6.45 (s, 1H), 6.35 (d, J=2.1 Hz, 1H), 5.98 (s, 2H), 3.61 (s, 6H), 2.38 (q, J=7.2 Hz, 2H), 2.26 (s, 3H), 2.18 (s, 3H), 2.16 (s, 3H), 1.95 (s, 3H), 1.05 (t, J=7.2 Hz, 3H).

3-(4-Acetoxy-3,5-dimethylphenyl)-4-(4-acetoxy-3-methylphenyl)-6-ethyl-8-methyl-2-oxo-2H-chromen-7-yl acetate (1-2bb) (38%). $^1$H NMR (300 MHz, CDCl$_3$) δ 6.68 (d, J=7.5 Hz, 1H), 6.65 (dd, J=7.1, 2.1 Hz, 1H), 6.45 (s, 1H), 6.35 (d, J=2.1 Hz, 1H), 6.23 (s, 1H), 2.31 (q, J=7.2 Hz, 2H), 2.23 (s, 3H), 2.15 (s, 3H), 2.14 (s, 3H), 2.11 (s, 6H), 1.98 (s, 3H), 1.15 (t, J=7.2 Hz, 3H).

3-(4-Acetoxy-3,5-dimethoxyphenyl)-4-(4-acetoxy-2-methylphenyl)-6-ethyl-8-methyl-2-oxo-2H-chromen-7-yl acetate (1-2cc) (36%). $^1$H NMR (300 MHz, CDCl$_3$) δ 6.68 (d, J=7.1 Hz, 1H), 6.60 (s, 1H), 6.46 (d, J=7. Hz, 1H), 6.30 (dd, J=6.9, 2.1 Hz, 1H), 5.92 (s, 2H), 3.65 (s, 6H), 2.33 (q, J=7.2 Hz, 2H), 2.2 (s, 3H), 2.18 (s, 3H), 2.16 (s, 3H), 1.95 (s, 3H), 1.15 (t, J=7.2 Hz, 3H).

3-(4-Acetoxy-3,5-dimethylphenyl)-4-(4-acetoxy-2-fluorophenyl)-6-ethyl-8-methyl-2-oxo-2H-chromen-7-yl acetate (1-2dd) (38%). $^1$H NMR (300 MHz, CDCl$_3$) δ 6.88 (dd J=6.9, 6.5 Hz, 1H), 6.66 (brd, J=7.0 Hz, 1H), 6.56(s, 1H), 6.45 (brd, J=6.5 Hz, 1H), 2.31 (q, J=7.2 Hz, 2H), 2.29 (s, 3H), 2.18 (s, 3H), 2.14 (s, 3H), 2.12 (s, 6H), 1.95 (s, 3H), 1.17 (t, J=7.2 Hz, 3H).

Step 3. 3-(4-Hydroxy-3,5-dimethoxyphenyl)-4-(4-hydroxyphenyl)-8-8-methyl-2H-chromen-7-ol (1-3a)

3-(4-Acetoxy-3,5-dimethoxyphenyl)-4-(4-acetoxyphenyl)-8-methyl-2-oxo-2H-chromen-7-yl acetate (24 g, 1 eq), and THF (1500 mL) was added to a flask under N$_2$ and cooled to 5° C. Borane dimethyl sulfide complex 2 M in THF (400 ml, 18 eq) was added over 10 mins. The solution was stirred for 2 hours at this temp then heated to 40 C o/n. The mixture was poured onto 2 M HCl (2000 mL) at <15° C., then extracted with EtOAc (2×1000 mL). The combined organics were washed with water (2×1000 mL), brine, dried (MgSO$_4$) then stripped to dryness affording crude (1-3a) as a sticky yellow solid. The material was purified by column chromatography eluting with heptane to heptane/EtOAc 3:2. The product fractions were stripped down to afford the title compound (9.5 g, 53%) as an orange solid. $^1$H NMR (300 MHz, Acetone-d$_6$) δ 8.39 (bs, 2H), 7.14 (s, 1H), 6.98 (d, J=8.6 Hz, 2H), 6.82 (d, J=8.6 Hz, 2H), 6.54 (d, J=7.9 Hz, 1H), 6.40 (d, J=7.9 Hz, 1H), 6.35 (s, 2H), 5.07 (s, 2H), 3.61 (s, 6H), 2.12 (s, 3H).

Other analogues prepared by this method:

4-(4-Hydroxyphenyl)-8-methyl-3-(3,4,5-trimethoxyphenyl)-2H-chromen-7-ol (1-3b) (47%). $^1$H NMR (300 MHz, Acetone-d$_6$) δ 8.38 (bs, 2H), 6.98 (d, J=8.8 Hz, 2H), 6.81 (d, J=8.8 Hz, 2H), 6.53 (d, J=7.9 Hz, 1H), 6.43-6.35 (m, 3H), 5.08 (s, 2H), 3.66 (s, 3H), 3.61 (s, 6H), 2.22 (s, 3H).

3-(3,5-Di-tert-butyl-4-hydroxyphenyl)-4-(4-hydroxyphenyl)-8-methyl-2H-chromen-7-ol (1-3c) (36%). $^1$H NMR (300 MHz, Acetone-d$_6$) δ 8.36-8.29 (m, 2H), 7.50-7.42 (m, 1H), 6.94-6.77 (m, 5H), 6.52 (d, J=7.9 Hz, 1H), 6.39 (d, J=7.9 Hz, 1H), 5.97 (s, 1H), 5.09 (s, 2H), 2.13 (s, 3H), 1.51 (s, 9H), 1.30 (s, 9H).

4-(4-Hydroxyphenyl)-8-methyl-3-(3,4,5-trifluorophenyl)-2H-chromen-7-ol (1-3d) (41%). $^1$H NMR (300 MHz, Acetone-d$_6$) δ 8.52 (bs, 1H), 8.50 (bs, 1H), 6.98 (d, J=8.3 Hz, 2H), 6.90-6.80 (m, 4H), 6.54 (d, J=7.9 Hz, 1H), 6.47 (d, J=7.9 Hz, 1H), 5.05 (s, 2H), 2.12 (s, 3H).

4-(3-Fluoro-4-hydroxyphenyl)-3-(3,4,5-trifluorophenyl)-2H-chromen-7-ol (1-3e) (34%). $^1$H NMR (300 MHz, Acetone-d$_6$) δ 8.80 (bs, 1H), 8.66 (bs, 1H), 7.05-6.77 (m, 5H), 6.74-6.66 (m, 1H), 6.45-6.34 (m, 2H), 5.03 (s, 2H).

4-(3-Fluoro-4-hydroxyphenyl)-3-(4-hydroxy-3,5-dimethoxyphenyl)-2H-chromen-7-ol (1-3f) (44%). $^1$H NMR (300 MHz, Acetone-d$_6$) δ 8.72 (bs, 1H), 8.57 (bs, 1H), 7.20 (bs, 1H), 7.06-6.96 (m, 1H), 6.91-6.80 (m, 2H), 6.81-6.75 (m, 1H), 6.45-6.37 (m, 4H), 5.08 (s, 2H), 3.63 (s, 6H).

4-(3-Fluoro-4-hydroxyphenyl)-3-(3,4,5-trimethoxyphenyl)-2H-chromen-7-ol (1-3 g) (48%). $^1$H NMR (300 MHz, Acetone-d$_6$) δ 8.74 (bs, 1H), 8.59 (bs, 1H), 7.04-6.80 (m, 3H), 6.84-6.82 (m, 1H), 6.48-6.37 (m, 4H), 5.08 (s, 2H), 3.70 (s, 3H), 3.62 (s, 6H).

4-(3-Fluoro-4-hydroxyphenyl)-8-methyl-3-(3,4,5-trifluorophenyl)-2H-chromen-7-ol (1-3h) (48%). $^1$H NMR (300 MHz, Acetone-d$_6$) δ 8.80 (bs, 1H), 8.57 (bs, 1H), 7.04-6.75 (m, 5H), 6.54 (d, J=8.2 Hz, 1H), 6.43 (d, J=8.2 Hz, 1H), 5.06 (s, 2H), 2.12 (s, 3H).

4-(3-Fluoro-4-hydroxyphenyl)-3-(4-hydroxy-3,5-dimethoxyphenyl)-8-methyl-2H-chromen-7-ol (1-3i) (53%). $^1$H NMR (300 MHz, Acetone-d$_6$) δ 8.66 (bs, 1H), 8.37 (bs, 1H), 7.19 (bs, 1H), 7.06-6.76 (m, 3H), 6.53 (d, J=8.5 Hz, 1H), 6.45-6.35 (m, 3H), 5.07 (s, 2H), 3.63 (s, 6H), 2.17 (s, 3H).

4-(3-Fluoro-4-hydroxyphenyl)-8-methyl-3-(3,4,5-trimethoxyphenyl)-2H-chromen-7-ol (1-3j) (49%). $^1$H NMR (300 MHz, Acetone-d$_6$) δ 8.68 (bs, 1H), 8.49 (bs, 1H), 7.04-6.77 (m, 3H), 6.53 (d, J=8.5 Hz, 1H), 6.48-6.36 (m, 3H), 5.07 (s, 2H), 3.68 (s, 3H), 3.65 (s, 6H), 2.13 (s, 3H).

3-(4-Hydroxy-3,5-dimethoxyphenyl)-4-(4-methoxy-3,5-dimethylphenyl)-8-methyl-2H-chromen-7-ol (1-3k) (22%). $^1$H NMR (300 MHz, Acetone-d$_6$) δ 8.37 (bs, 1H), 7.21 (bs, 1H), 6.32 (s, 2H), 6.49-6.34 (m, 4H), 5.08 (s, 2H), 3.71 (s, 3H), 3.60 (s, 6H), 2.22 (s, 6H), 2.13 (s, 3H).

4-(4-Methoxy-3,5-dimethylphenyl)-8-methyl-3-(3,4,5-trimethoxyphenyl)-2H-chromen-7-ol (1-3l) (15%). $^1$H NMR (300 MHz, Acetone-d$_6$) δ 8.41 (bs, 1H), 6.81 (s, 2H), 6.49-6.36 (m, 4H), 5.08 (s, 2H), 3.73 (s, 3H), 3.66 (s, 3H), 3.61 (s, 6H), 2.22 (s, 6H), 2.12 (s, 3H).

4-(3,5-Difluoro-4-hydroxyphenyl)-3-(4-hydroxy-3,5-dimethoxyphenyl)-8-methyl-2H-chromen-7-ol (1-3m) (47%). $^1$H NMR (300 MHz, Acetone-d$_6$) δ 6.86-6.74 (m, 2H), 6.47-6.36 (m, 4H), 5.10 (s, 2H), 3.66 (s, 6H), 2.13 (s, 3H).

4-(3,5-Difluoro-4-hydroxyphenyl)-8-methyl-3-(3,4,5-trimethoxyphenyl)-2H-chromen-7-ol (1-3n) (55%). $^1$H NMR (300 MHz, Acetone-d$_6$) δ 6.86-6.75 (m, 2H), 6.49-6.37 (m, 4H), 5.12 (s, 2H), 3.66 (s, 9H), 2.14 (s, 3H).

4-(3-fluoro-4-hydroxyphenyl)-8-propyl-3-(4-hydroxy-3,5-dimethoxyphenyl)-2H-chromen-7-ol (1-3o) (36%). $^1$H NMR (300 MHz, Acetone-d$_6$) δ 8.72 (s, 1H), 8.12 (s, 1H), 7.05 (s, 1H), 7.01 (m, 1H), 6.95-78 (m, 2H), 6.48 (d, J=8.1 Hz, 2H), 6.45 (d, J=8.1 Hz, 2H), 6.41 (s, 2H), 5.02 (s, 2H), 3.71 (s, 6H), 2.65 (m, 1H), 1.65 (m, 1H), 1.06 (t, J=7.1 Hz, 3H).

4-(3-fluoro-4-hydroxyphenyl)-6-ethyl-3-(4-hydroxy-3,5-dimethoxyphenyl)-2H-chromen-7-ol (1-3p) (54%). $^1$H NMR (300 MHz, Acetone-d$_6$) δ 8.54 (s, 1H), 8.05 (s, 1H), 7.29 (s, 1H), 7.05 (m, 1H), 6.78 (m, 1H), 6.66 (s, 1H), 6.45 (s, 1H), 6.34 (s, 2H), 5.04 (s, 2H), 3.65 (s, 6H), 2.45 (m, 2H), 1.06 (t, J=7.1 Hz, 3H).

3-(4-hydroxy-3,5-dimethoxyphenyl)-4-(3,4-methylenedioxyphenyl)-8-methyl-2H-chromen-7-ol (1-3q) (54%). $^1$H NMR (300 MHz, Acetone-d$_6$) δ 8.23 (s, 1H), 7.31 (s, 1H), 6.82 (d, J=8.01 Hz, 1H), 6.66 (d, J=8.1 Hz, 1H), 6.61 (s, 1H), 6.50 (d, J=8.2 Hz, 1H), 6.42 (s, 2H), 6.40 (d, J=8.2 Hz, 1H), 6.04 (s, 2H), 5.11 (s, 2H), 3.57 (s, 6H), 1.78 (s, 3H).

3-(4-hydroxy-3,5-dimethoxyphenyl)-4-(4-nitrophenyl)-8-methyl-2H-chromen-7-ol (1-3r) (24%). $^1$H NMR (300 MHz, Acetone-d$_6$) δ 8.23 (s, 1H), 8.23 (d, J=8.6 Hz, 2H), 7.45 (d, J=8.4 Hz, 2H), 7.25 (s, 1H), 6.38 (s, 2H), 6.32 (s, 2H), 5.04 (s, 2H), 3.56 (s, 6H), 2.01 (s, 3H).

3-(4-hydroxy-3,5-dimethoxyphenyl)-4-(4-ethylaminophenyl)-8-methyl-2H-chromen-7-ol (1-3s) (21%). $^1$H NMR (300 MHz, Acetone-d$_6$) δ 8.23 (s, 1H), 7.22 (d, J=8.2 Hz, 1H), 6.97 (d, J=8.2 Hz, 2H), 6.66 (d, J=8.3 Hz, 2H), 6.34 (d, J=8.2 Hz, 1H), 6.34 (s, 2H), 5.04 (s, 2H), 3.45 (s, 6H), 3.05 (m, 2H), 1.06 (t, J=7.6 Hz, 3H).

4-(4-hydroxyphenyl)-6-ethyl-8-methyl-3-(4-hydroxy-3,5-dimethoxyphenyl)-2H-chromen-7-ol (1-3t) (31%). $^1$H NMR (300 MHz, Acetone-d$_6$) δ 8.67 (s, 1H), 7.45 (s, 1H), 7.05 (d, J=8.3 Hz, 2H), 6.98 (d, J=8.3 Hz, 2H), 6.65 (s, 1H), 6.45 (s, 2H), 5.08 (s, 2H), 3.56 (s, 6H), 2.55 (m, 2H), 2.05 (s, 3H), 1.07 (t, J=7.2 Hz, 3H).

4-(4-hydroxyphenyl)-8-ethyl-3-(4-hydroxy-3,5-dimethoxyphenyl)-2H-chromen-7-ol (1-3u) (61%). $^1$H NMR (300 MHz, Acetone-d$_6$) δ 8.34 (s, 1H), 8.11 (s, 1H), 7.26 (s, 1H), 7.01 (m, 2H), 6.76 (m, 2H), 6.56 (d, J=8.1 Hz, 1H), 6.50 (d, J=8.2 Hz, 1H), 6.45 (s, 2H), 5.10 (s, 2H), 3.47 (s, 6H), 2.65 (m, 2H), 1.06 (t, J=7.5 Hz, 3H).

4-(4-hydroxyphenyl)-6-methyl-3-(4-hydroxy-3,5-dimethoxyphenyl)-2H-chromen-7-ol (1-3v) (68%). $^1$H NMR (300 MHz, Acetone-d$_6$) δ 8.88 (s, 1H), 8.23 (s, 1H), 7.33 (d, J=3 Hz, 1H), 7.05 (m, 2H), 6.78 (m, 2H), 6.65 (s, 1H), 6.34 (s, 2H), 5.11 (s, 2H), 3.56 (s, 6H), 2.07 (s, 3H).

4-(3-fluoro-4-hydroxyphenyl)-5-fluoro-3-(4-hydroxy-3,5-dimethoxyphenyl)-2H-chromen-7-ol (1-3w) (21%). $^1$H NMR (300 MHz, Acetone-d$_6$) δ 8.12 (s, 1H), 7.23 (s, 1H), 6.88-76 (m, 3H), 6.50 (s, 1H), 6.45 (s, 2H), 6.05 (d, J=8.2 Hz, 1H), 4.89 (s, 2H), 3.56 (s, 6H).

6-chloro-4-(3-fluoro-4-hydroxyphenyl)-3-(4-hydroxy-3,5-trimethoxyphenyl)-2H-chromen-7-ol (1-3x) (21%). $^1$H NMR (300 MHz, Acetone-d$_6$) δ 7.32 (m, 1H), 7.16-09 (m, 2H), 6.94 (s, 1H), 6.59 (s, 1H), 6.39 (s, 2H), 5.10 (s, 2H), 3.65 (s, 6H).

4-(3-chloro-4-hydroxyphenyl)-3-(4-hydroxy-3,5-dimethoxyphenyl)-8-methyl-2H-chromen-7-ol (1-3y) (41%). $^1$H NMR (300 MHz, Acetone-d$_6$) δ 7.11 (d, J=1.6 Hz, 1H), 6.96 (d, J=8.1 Hz, 1H), 6.88 (dd, J=1.2, 8.2 Hz, 1H), 6.55 (d, J=8.2 Hz, 1H), 6.45 (d, J=8.1 Hz, 1H), 6.42 (s, 2H), 5.11 (s, 2H), 3.65 (s, 6H), 2.05 (s, 3H).

4-(3-fluoro-4-hydroxyphenyl)-6-ethyl-8-methyl-3-(4-hydroxy-3,5-dimethoxyphenyl)-2H-chromen-7-ol (1-3z) (41%). $^1$H NMR (300 MHz, Acetone-d$_6$) δ 8.77 (s, 1H), 7.49 (s, 1H), 7.15 (m, 2H), 6.98 (brs, 1H), 6.65 (s, 1H), 6.45 (s, 2H), 5.08 (s, 2H), 3.56 (s, 6H), 2.55 (m, 2H), 2.05 (s, 3H), 1.07 (t, J=7.2 Hz, 3H).

4-(3-methyl-4-hydroxyphenyl)-6-ethyl-8-methyl-3-(4-hydroxy-3,5-dimethoxyphenyl)-2H-chromen-7-ol (1-3aa) (38%). $^1$H NMR (300 MHz, CDCl$_3$) δ 8.22 (br, 2H), 7.66 (s, 1H), 6.62 (d, J=7.1 Hz, 1H), 6.55 (dd, J=7.1, 2.3 Hz, 1H), 6.41 (s, 1H), 6.38 (d, J=2.5 Hz, 1H), 5.95 (s, 2H), 3.51 (s, 6H), 2.32 (q, J=7.2 Hz, 2H), 2.21 (s, 3H), 2.18 (s, 3H), 2.14 (s, 3H), 1.92 (s, 3H), 1.05 (t, J=7.2 Hz, 3H).

4-(3-fluoro-4-hydroxyphenyl)-6-ethyl-8-methyl-3-(4-hydroxy-3,5-dimethoxyphenyl)-2H-chromen-7-ol (1-3bb) (38%). $^1$H NMR (300 MHz, CDCl$_3$) δ 6.68 (d, J=7.5 Hz, 1H), 6.65 (dd, J=7.1, 2.1 Hz, 1H), 6.45 (s, 1H), 6.35 (d, J=2.1 Hz, 1H), 6.23 (s, 2H), 2.31 (q, J=7.2 Hz, 2H), 2.23 (s, 3H), 2.15 (s, 3H), 2.14 (s, 3H), 2.11 (s, 6H), 1.98 (s, 3H), 1.15 (t, J=7.2 Hz, 3H).

3-(4-Acetoxy-3,5-dimethylphenyl)4-(4-acetoxy-3-methylphenyl)-6-ethyl-8-methyl-2-oxo-2H-chromen-7-yl acetate (1-3cc) (36%). $^1$H NMR (300 MHz, CDCl$_3$) δ 6.68 (d, J=7.1 Hz, 1H), 6.60 (s, 1H), 6.46 (d, J=7 Hz, 1H), 6.30 (dd, J=6.9, 2.1 Hz, 1H), 5.92 (s, 2H), 3.65 (s, 6H), 2.33 (q, J=7.2 Hz, 2H), 2.2 (s, 3H), 2.18 (s, 3H), 2.16 (s, 3H), 1.95 (s, 3H), 1.15 (t, J=7.2 Hz, 3H).

3-(4-Acetoxy-3,5-dimethylphenyl)-4-(4-acetoxy-2-fluorophenyl)-6-ethyl-8-methyl-2-oxo-2H-chromen-7-yl acetate (1-3dd) (38%). $^1$H NMR (300 MHz, CDCl$_3$) δ 9.08 (br 1H), 8.65 (s, 1H), 8.22 (br 1H), 6.81 (dd J=6.6, 6.3 Hz, 1H), 6.62 (brd, J=7.0 Hz, 1H), 6.46 (s, 1H), 6.35 (brd, J=6.5 Hz, 1H), 2.31 (q, J=7.2 Hz, 2H), 2.29 (s, 3H), 2.18 (s, 3H), 2.14 (s, 3H), 2.12 (s, 6H), 1.95 (s, 3H), 1.17 (t, J=7.2 Hz, 3H).

Step 4. 3-(4-Hydroxy-3,5-dimethoxyphenyl)-4-(4-hydroxyphenyl)-8-methylchroman-7-ol (Compound 2) (1-4a)

3-(4-Hydroxy-3,5-dimethoxyphenyl)-4-(4-hydroxyphenyl)-8-methyl-2H-chromen-7-ol (4.8 g, 1 eq), IMS (500 mL) and Pd/C 10% type 338 paste (3.0 g) was added to a hydrogenator and filled with H$_2$ 2.5bar. The reaction was left at 40° C. overnight and showed complete conversion. The catalyst was filtered off and the filtrates stripped to dryness. Three equal batches were blended and dried to afford 12.6 g (88%) of Compound 2 as an off-white solid. $^1$H NMR (300 MHz, Acetone-d$_6$) δ 6.65-6.51 (m, 5H), 6.40 (d, J=7.9 Hz, 1H), 6.04 (s, 2H), 4.44-4.35 (m, 1H), 4.25-4.15 (m, 2H), 3,64 (s, 6H), 3.46-3.37 (m, 1H), 2.15 (s, 3H).

Other compounds of formula (I) prepared by this method:

4-(4-Hydroxyphenyl)-8-methyl-3-(3,4,5-trimethoxyphenyl)chroman-7-ol (Compound 1) (1 -4b) (99%). $^1$H NMR (300 MHz, Acetone-d$_6$) δ 6.63-6.49 (m, 5H), 6.36 (d, J=7.9 Hz, 1H), 6.04 (s, 2H), 4.46-4.36 (m, 1H), 4.25-4.17 (m, 2H), 3.68 (s, 3H), 3.63 (s, 6H), 3.49-3.40 (m, 1H), 2.15 (s, 3H).

3-(3,5-Di-tert-butyl-4-hydroxyphenyl)-4-(4-hydroxyphenyl)-8-methylchroman-7-ol (Compound 3) (1-4c) (33%). $^1$H NMR (300 MHz, Acetone-d$_6$) δ 8.10 (bs 1H), 8.05 (bs, 1H) 7.28-7.20 (m, 1H), 6.63-6.52 (m, 3H), 6.43-6.36 (m, 2H), 6.04 (s, 2H), 4.47-4.35 (m, 1H), 4.24-4.09 (m, 2H), 3.64 (s, 6H), 3.78-3.66 (m, 1H), 2.15 (s, 3H), 1.45 (s, 9H), 1.32 (s, 9H).

4-(4-Hydroxyphenyl)-8-methyl-3-(3,4,5-trifluorophenyl)chroman-7-ol (Compound 4) (1-4d) (95%). $^1$H NMR (300 MHz, Acetone-d$_6$) δ 6.67-6.52 (m, 7H), 6.42 (d, J=7.8 Hz, 1H), 4.48-4.40 (m, 1H), 4.35-4.26 (m, 2H), 3.64-3.55 (m, 1H), 2.15 (s, 3H).

4-(3-Fluoro-4-hydroxyphenyl)-3-(3,4,5-trifluorophenyl)chroman-7-ol (Compound 5) (1-4e) (50%). $^1$H NMR (300 MHz, Acetone-d$_6$) δ 6.84-6.65 (m, 4H), 6.49-6.30 (m, 4H), 4.48-4.18 (m, 3H), 3.67-3.56 (m, 1H).

4-(3-Fluoro-4-hydroxyphenyl)-3-(4-hydroxy-3,5-dimethoxyphenyl)chroman-7-ol (Compound 6) (1-4f) (39%). $^1$H NMR (300 MHz, Acetone-d$_6$) δ 6.80-6.74 (m, 2H), 6.44-6.32 (m, 4H), 6.08 (s, 2H), 4.41-4.33 (m, 1H), 4.24-4.12 (m, 2H), 3.66 (s, 6H), 3.52-3.38 (m, 1H).

4-(3-Fluoro-4-hydroxyphenyl)-3-(3,4,5-trimethoxyphenyl)chroman-7-ol (Compound 7) (1-4 g) (22%). $^1$H NMR (300 MHz, Acetone-d$_6$) δ 6.80-6.72 (m, 2H), 6.48-6.33 (m, 4H), 6.11 (s, 2H), 4.44-4.35 (m, 1H), 4.25-4.14 (m, 2H), 3.70 (s, 3H), 3.64 (s, 6H), 3.52-3.45 (m, 1H).

4-(3-Fluoro-4-hydroxyphenyl)-8-methyl-3-(3,4,5-trifluorophenyl)chroman-7-ol (Compound 8) (1-4h) (50%). $^1$H NMR (300 MHz, Acetone-d$_6$) δ 6.81-6.65 (m, 3H), 6.60 (d, J=8.6 Hz, 1H), 6.49-6.40 (m, 2H), 6.39-6.30 (m, 1H), 4.50-4.42 (m, 1H), 4.38-4.30 (m, 2H), 3.66-3.55 (m, 1H), 2.16 (s, 3H).

4-(3-Fluoro-4-hydroxyphenyl)-3-(4-hydroxy-3,5-dimethoxyphenyl)-8-methylchroman-7-ol (Compound 9) (1-4i) (60%). $^1$H NMR (300 MHz, Acetone-d$_6$) δ 6.78-6.70 (m, 1H), 6.60 (d, J=8.2 Hz, 1H), 6.46-6.32 (m, 3H), 6.07 (s, 2H), 4.45-4.35 (m, 1H), 4.28-4.17 (m, 2H), 3.65 (s, 6H), 3.49-3.41 (m, 1H), 2.20 (s, 3H).

4-(3-Fluoro-4-hydroxyphenyl)-8-methyl-3-(3,4,5-trimethoxyphenyl)chroman-7-ol (Compound 10) (1-4j) (44%). $^1$H NMR (300 MHz, Acetone-d$_6$) δ 6.80-6.71 (m, 1H), 6.60 (d, J=8.2 Hz, 1H), 6.46-6.32 (m, 4H), 6.10 (s, 2H), 4.48-4.38 (m, 1H), 4.31-4.22 (m, 2H), 3.69 (s, 3H), 3.65 (s, 6H), 3.53-3.41 (m, 1H), 2.17 (s, 3H).

3-(4-Hydroxy-3,5-dimethoxyphenyl)-4-(4-methoxy-3,5-dimethylphenyl)-8-methylchroman-7-ol (Compound 11) (1-4k) (83%). $^1$H NMR (300 MHz, DMSO-d$_6$) δ 6.52 (d, J=8.5 Hz, 1H), 6.33 (d, J=8.5 Hz, 1H), 6.25 (s, 2H), 5.91 (s, 2H), 4.34-4.24 (m, 1H), 4.18-4.05 (m, 2H), 3.57 (s, 3H), 3.50 (s, 6H), 3.48-3.33 (m, 1H), 2.05 (s, 3H), 2.03 (s, 6H).

4-(4-Methoxy-3,5-dimethylphenyl)-8-methyl-3-(3,4,5-trimethoxyphenyl)chroman-7-ol (Compound 12) (1-4l)

(99%). ¹H NMR (300 MHz, Acetone-d₆) δ 6.58 (d, J=8.8 Hz, 1H), 6.42 (d, J=8.8 Hz, 1H), 6.33 (s, 2H), 6.05 (s, 2H), 4.52-4.37 (m, 1H), 4.25-4.12 (m, 2H), 3.68 (s, 3H), 3.65 (s, 3H), 3.11 (s, 6H), 3.50-3.39 (m, 1H), 2.15 (s, 3H), 2.07 (s, 6H).

4-(2,3-Difluoro-4-hydroxyphenyl)-3-(4-hydroxy-3,5-dimethoxyphenyl)-8-methylchroman-7-ol (Compound 13) (1-4m) (60%). ¹H NMR (300 MHz, Acetone-d₆) δ 6.73-6.68 (m, 1H), 6.64-6.57 (m, 1H), 6.55-6.49 (m, 1H), 6.42 (d, J=9.6 Hz, 1H), 6.08 (s, 2H), 4.59-4.55 (m, 1H), 4.46-4.36 (m, 1H), 4.25-4.21 (m, 1H), 3.63 (s, 6H), 3.53-3.47 (m, 1H), 2.14 (s, 3H).

4-(2,3-Difluoro-4-hydroxyphenyl)-8-methyl-3-(3,4,5-trimethoxyphenyl)chroman-7-ol (Compound 14) (1-4n) (66%). ¹H NMR (300 MHz, Acetone-d₆) δ 6.74-6.68 (m, 1H), 6.60 (d, J=9.5 Hz, 1H), 6.55-6.47 (m, 1H), 6.44 (d, J=9.5 Hz, 1H), 6.13 (s, 2H), 4.61-4.57 (m, 1H), 4.48-4.36 (m, 1H), 4.29-4.22 (m, 1H), 3.67 (s, 3H), 3.64 (s, 6H), 3.58-3.48 (m, 1H), 2.14 (s, 3H).

4-(3-fluoro-4-hydroxyphenyl)-3-(4-hydroxy-3,5-dimethoxyphenyl)-8-propylchroman-7-ol (Compound 16) (1-4o) (80%). ¹H NMR (300 MHz, Acetone-d₆) δ 6.76 (m, 1H), 6.65 (d, J=8.1 Hz, 1H), 6.45-33 (m, 3H), 6.05 (s, 2H), 4.44 (m, 1H), 4.27 (m, 1H), 3.56 (s, 6H), 3.45 (m, 1H), 2.65 (m, 2H), 1.67 (m, 2H), 1.07 (t, J=7.1 Hz, 3H).

4-(3-fluoro-4-hydroxyphenyl)-3-(4-hydroxy-3,5-dimethoxyphenyl)-6-ethylchroman-7-ol (Compound 18) (1-4p) (80%). ¹H NMR (300 MHz, Acetone-d₆) δ 6.76 (m, 1H), 6.66 (s, 1H), 6.56-38 (m, 3H), 6.05 (s, 2H), 4.45 (m, 1H), 4.12 (m, 1H), 3.55 (s, 6H), 3.45 (m, 1H), 2.51 (m, 2H), 1.05 (t, J=7.1 Hz, 3H).

4-(3,4-methylenedioxyphenyl)-3-(4-hydroxy-3,5-dimethoxyphenyl)-8-methylchroman-7-ol (Compound 32) (1-4q) (80%). ¹H NMR (300 MHz, Acetone-d₆) δ 8.08 (s, 1H), 7.01 (s, 1H), 6.71 (m, 2H), 6.55 (d, J=8.2 Hz, 1H), 6.23 (d, J=8.1 Hz, 2H), 6.06 (s, 2H), 4.47 (m, 1H), 4.18 (m, 1H), 3.65 (s, 6H), 3.46 (m, 1H), 2.05 (s, 3H).

4-(4-aminophenyl)-3-(4-hydroxy-3,5-dimethoxyphenyl)-8-methylchroman-7-ol (Compound 21) (1-4r) (70%). ¹H NMR (300 MHz, Acetone-d₆) δ 6.67(m, 1H), 6.45-33 (m, 5H), 6.09 (s, 2H), 4.47 (m, 1H), 4.13 (m, 1H), 3.64 (s, 6H), 3.35 (m, 1H), 2.06 (s, 3H).

4-(4-ethylaminophenyl)-3-(4-hydroxy-3,5-dimethoxyphenyl)-8-methylchroman-7-ol (Compound 22) (1-4s) (78%). ¹H NMR (300 MHz, Acetone-d₆) δ6.65 (m, 1H), 6.51-39 (m, 5H), 6.01 (s, 2H), 4.65 (m, 1H), 4.45 (m, 1H), 4.40 (m, 1H), 3.65 (s, 6H), 3.45 (m, 1H), 3.11 (m, 2H), 2.06 (s, 3H), 1.32 (t, J=7.1 Hz, 3H).

4-(4-hydroxyphenyl)-3-(4-hydroxy-3,5-dimethoxyphenyl)-6-ethyl-8-methylchroman-7-ol (Compound 33) (1-4t) (80%). ¹H NMR (300 MHz, Acetone-d₆) δ 6.75 (m, 1H), 6.61 (s, 1H), 6.45 (m, 3H), 6.01 (s, 2H), 4.45 (m, 1H), 4.23 (m, 2H), 3.65 (s, 6H), 3.45 (m, 1H), 2.55 (m, 2H), 2.01 (s, 3H), 1.07 (t, J=7.1 Hz, 3H).

4-(4-hydroxyphenyl)-3-(4-hydroxy-3,5-dimethoxyphenyl)-8-ethylchroman-7-ol (Compound 34) (1-4u) (86%). ¹H NMR (300 MHz, Acetone-d₆) δ6.72 (m, 1H), 6.56 (d, J=8.2 Hz, 1H), 6.50-33 (m, 4H), 6.01 (s, 2H), 4.51 (m, 1H), 4.32 (m, 2H), 3.65 (s, 6H), 3.45 (m, 1H), 2.65 (m, 2H), 1.06 (t, J=7.1 Hz, 3H).

4-(4-hydroxyphenyl)-3-(4-hydroxy-3,5-dimethoxyphenyl)-6-methylchroman-7-ol (Compound 35) (1-4v) (96%). ¹H NMR (300 MHz, Acetone-d₆) δ 6.67 (m, 1H), 6.56 (s, 1H), 6.45-32 (m, 4H), 6.01 (s, 2H), 4.45 (m, 1H), 4.32 (m, 2H), 3.67 (s, 6H), 3.45 (m, 1H), 2.06 (s, 3H).

4-(3-fluoro-4-hydroxyphenyl)-3-(4-hydroxy-3,5-dimethoxyphenyl)-5-fluorochroman-7-ol (Compound 19) (1-4w) (66%). ¹H NMR (300 MHz, Acetone-d₆) δ 6.67 (m, 1H), 6.45 (m, 2H), 6.25 (m, 1H), 6.18 (m, 1H), 6.01 (s, 2H), 4.50 (m, 1H), 4.35 (m, 1H), 4.27 (m, 1H), 3.67 (s, 6H), 3.45 (m, 1H).

4-(3-fluoro-4-hydroxyphenyl)-3-(4-hydroxy-3,5-dimethoxyphenyl)-6-chlorochroman-7-ol (Compound 20) (1-4x) (56%). ¹H NMR (300 MHz, Acetone-d₆) δ 8.16 (s, 1H), 7.89 (s, 1H), 7.21 (s, 1H), 6.96 (s, 1H), 6.75 (m, 1H), 6.60 (s, 1H), 6.45 (m, 1H), 6.01 (s, 2H), 4.45 (m, 1H), 4.30 (m, 2H), 3.67 (s, 6H), 3.45 (m, 1H).

4-(3-chloro-4-hydroxyphenyl)-3-(4-hydroxy-3,5-dimethoxyphenyl)-8-methylchroman-7-ol (Compound 24) (1-4y) (66%). ¹H NMR (300 MHz, Acetone-d₆) δ8.1 (s, 1H), 7.6 (s, 1H), 7.0 (s, 1H), 6.65-50 (m, 4H), 6.42 (d, J=8.2 Hz, 1H), 6.01 (s, 2H), 4.41 (m, 1H), 4.35 (m, 2H), 3.64 (s, 6H), 3.46 (m, 1H).

4-(3-fluoro-4-hydroxyphenyl)-3-(4-hydroxy-3,5-dimethoxyphenyl)-6-ethyl-8-methylchroman-7-ol (Compound 36) (1-4z) (80%). ¹H NMR (300 MHz, Acetone-d₆) δ 6.75 (m, 1H), 6.61 (s, 1H), 6.45 (m, 3H), 6.01 (s, 2H), 4.45 (m, 1H), 4.23 (m, 2H), 3.65 (s, 61-1), 3.45 (m, 1H), 2.55 (m, 2H), 2.01 (s, 3H), 1.07 (t, J=7.1 Hz, 3H).

4-(3-methyl-4-hydroxyphenyl)-3-(4-hydroxy-3,5-dimethoxyphenyl)-6-ethyl-8-methylchroman-7-ol (Compound 37) (1-4aa) (88%). ¹H NMR (300 MHz, CDCl₃) δ 8.22 (br, 2H), 7.66 (s, 1H), 6.62 (d, J=7.1 Hz, 1H), 6.55 (dd, J=7.1, 2.3 Hz, 1H), 6.41 (s, 1H), 6.38 (d, J=2.5 Hz, 1H), 5.95 (s, 2H), 4.48 (m, 1H), 4.21 (m, 2H), 3.61 (s, 6H), 3.45 (m, 1H), 2.55 (m, 2H), 2.01 (s, 3H), 1.07 (t, J=7.1 Hz, 3H).

4-(3-methyl-4-hydroxyphenyl)-6-ethyl-8-methyl-3-(4-hydroxy-3,5-dimethylphenyl)-2H-chromen-7-ol (compound 38) (1-4bb) (80%). ¹H NMR (300 MHz, CDCl₃) δ 6.68 (d, J=7.5 Hz, 1H), 6.65 (dd, J=7.1, 2.1 Hz, 1H), 6.45 (s, 1H), 6.35 (d, J=2.1 Hz, 1H), 6.23 (s, 2H), 4.45 (m, 1H), 4.23 (m, 2H), 3.45 (m, 1H), 2.55 (m, 2H), 2.15 (s, 6H), 2.01 (s, 3H), 1.02 (t, J=7.1 Hz, 3H).

4-(2-methyl-4-hydroxyphenyl)-6-ethyl-8-methyl-3-(4-hydroxy-3,5-dimethoxyphenyl)-2H-chromen-7-ol (compound 39) (1-4cc) (76%). ¹H NMR (300 MHz, CDCl₃) δ 6.68 (d, J=7.1 Hz, 1H), 6.60 (s, 1H), 6.46 (d, J=7 Hz, 1H), 6.30 (dd, J=6.9, 2.1 Hz, 1H), 5.92 (s, 2H), 4.42 (m, 1H), 4.31 (m, 2H), 3.65 (s, 6H), 3.41 (m, 1H), 2.51 (m, 2H), 2.11 (s, 3H), 1.01(t, J=7.1 Hz, 3H).

4-(2-fluoro-4-hydroxyphenyl)-6-ethyl-8-methyl-3-(4-hydroxy-3,5-dimethylphenyl)-2H-chromen-7-ol (compound 40) (1-4dd) (70%). ¹H NMR (300 MHz, CDCl₃) δ 9.1 (br 1H), 8.75 (s, 1H), 7.22 (br 1H), 6.85 (dd J=6.6, 6.1 Hz, 1H), 6.58 (brd, J=7.3 Hz, 1H), 6.42 (s, 1H), 6.25 (brd, J=6.1 Hz, 1H), 4.35 (m, 1H), 4.13 (m, 2H), 3.35 (m, 1H), 2.45 (m, 2H), 2.18 (s, 6H), 2.11(s, 3H), 1.05 (t, J=7.1 Hz, 3H).

Enantiomers of compound 2 were prepared by chiral resolution on a normal phase Chiralcel OD-H, 30×250 mm, 5 micron column. Anaysis of the compound with lowest retention time on this column indicated the following Optical Rotation properties:

| | |
|---|---|
| Specific Optical Rotation[α]²⁵₅₈₉ | +282.250° |
| Solvent: METHANOL | |
| Concentration: 1.0% | |

The enantiomer with the longest retention time on this column had the following Optical Rotation properties.

| | |
|---|---|
| Specific Optical Rotation[α]²⁵₅₈₉ | −277.00° |
| Solvent: METHANOL | |
| Concentration: 1.0% | |

Enantiomers of compound 6 were prepared by chiral resolution on a normal phase Chiralcel OD-H, 30×250 mm, 5 micron column. Anaysis of the compound with lowest retention time (enantiomer 1) on this column indicated the following Optical Rotation properties:

| | |
|---|---|
| Specific Optical Rotation$[\alpha]^{25}_{589}$ | +238.835° |
| Solvent: METHANOL | |
| Concentration: 0.1% | |

The enantiomer with the longest retention time (enantiomer 2) on this column had the following Optical Rotation properties:

| | |
|---|---|
| Specific Optical Rotation$[\alpha]^{25}_{589}$ | −259.410° |
| Solvent: METHANOL | |
| Concentration: 0.1% | |

Enantiomers of compound 9 were prepared by chiral resolution on a normal phase Chiralcel OD-H, 30×250 mm, 5 micron column. Anaysis of the compound with lowest retention time (enantiomer 1) on this column indicated the following Optical Rotation properties:

| | |
|---|---|
| Specific Optical Rotation$[\alpha]^{25}_{589}$ | +252.727° |
| Solvent: METHANOL | |
| Concentration: 0.1% | |

The enantiomer with the longest retention time (enantiomer 2) on this column had the following Optical Rotation properties:

| | |
|---|---|
| Specific Optical Rotation$[\alpha]^{25}_{589}$ | −281.900° |
| Solvent: METHANOL | |
| Concentration: 0.1% | |

Example 2

In Vitro Testing

The anti-cancer activity of compound 2 (the racemic form and a purified eutomer and distomer) was assessed by XenTech in two glioblastome multiforme patient-derived explants established from tumour biopsies following the methodology detailed. Primary cell cultures were obtained from explanted and dissociated ODA14-RAV and GBM14-CHA xenografts. Cells were thawed quickly in a 37° C. water bath. One vial of cells (~10 million cells) was diluted into 10 mL of complete growth medium (F12/DMEM supplemented with 8% foetal bovine serum, 100 µg/ml penicillin G sodium, 100 µg/ml streptomycin sulfate). After centrifugation at 150×g for 5 minutes the cell pellet was resuspended in complete growth medium and plated at a density of at least 140,000 cells/cm$^2$ in 75 cm$^2$ cell culture flasks. Cells were maintained at 37° C. in a humidified atmosphere with 5% $CO_2$ for at least one week. The cells were then harvested and seeded in 96-well plates at a density of 2.5×10$^3$ cells/well for cytotoxicity assays. Cells were incubated for 48 hrs at 37 ° C. prior to addition of the test compounds. Test compounds were added at desired final concentrations and further incubated for 72 hrs.

Cell viability was assessed prior to adding the test compounds (T0) and 72 hrs after by measuring cellular ATP cell content using CeliTiter-Glo® Luminescent Cell Viability Assay (Promega) according to the manufacturer's instructions.

Figure 2:
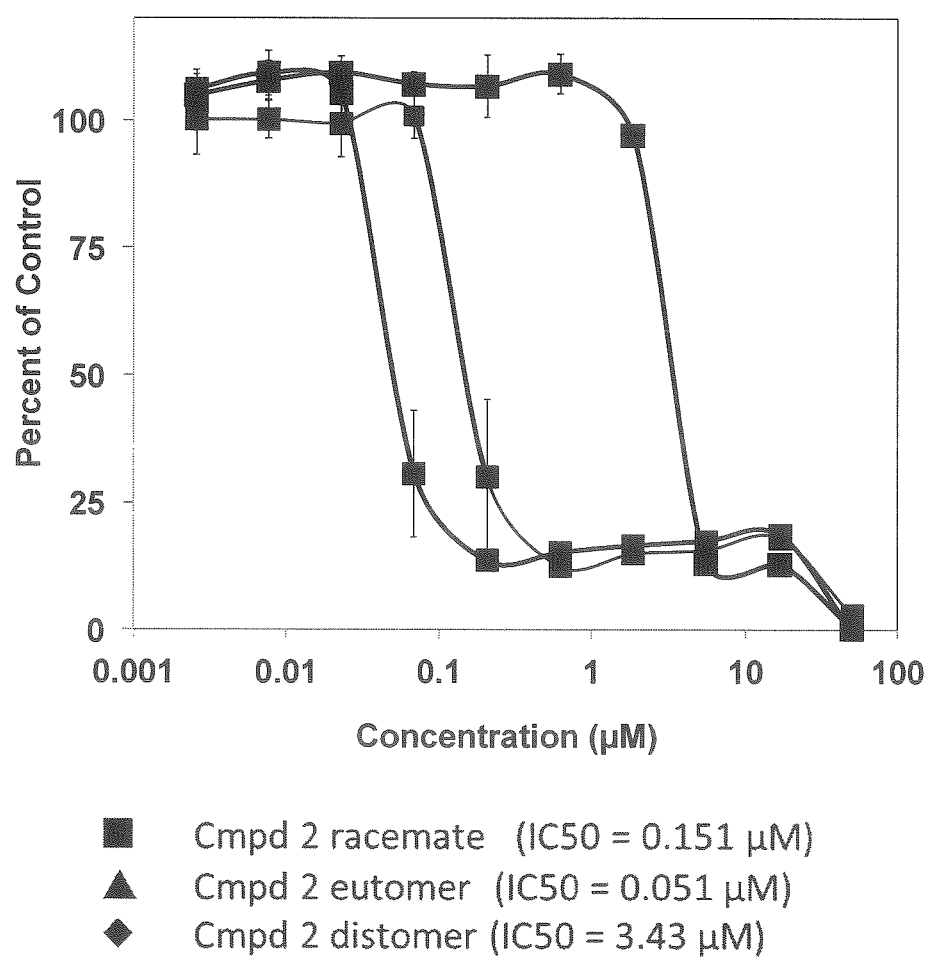
FIG. 2: Differential activity of compound 2 and its purified enantiomers against the GBM14 GBM patient-derived explant.

ODA14 was designated as grade III (determined by histopathology) susceptible to TMZ when assessed in xenograft studies, p53 mutant, pTEN wildtype and had amplified EGFR expression. GBM14 was designated as TMZ resistant, p53 pTEN mutant. EGFR wt. The GBM grade was not known. After 72 hrs exposure to compound 2, an $IC_{50}$ of 0.14 µM against GBM14 and 48 µM against ODA14 was observed. The results are shown in FIG. 1. After 72 hrs exposure of the eutomer of compound 2 an $IC_{50}$ of 0.051 µM was observed, whereas in contrast the distomer of compound 2 had an $IC_{50}$ of 3.43 µM (see FIG. 2) against the GBM14-CHA cell line. These data demonstrate that the eutomer of compound 2 (the+enantiomer) is some 2-3 fold more active against GBM14-CHA compared with the racemate of compound 2 and >60 fold more active than the distomer of compound 2 (the−enantiomer).

The enantiomers of compounds 6 and 9 were also assessed against GBM14-CHA glioblastoma cell line using the methodology described above. The results are presented below in Table 1.

TABLE 1

$IC_{50}$ data for the racemate and chiral forms of compounds 6 and 9 against glioblastoma cell line GBM14-CHA

| Compound | Chiral Form | $IC_{50}$ (µM) |
|---|---|---|
| 6 | Racemate | 0.19 |
| | Ent 1 | 0.069 |
| | Ent 2 | 28.3 |
| 9 | Racemate | 0.19 |
| | Ent 1 | 0.017 |
| | Ent 2 | 11.29 |

As was observed for compound 2, the eutomers of compound 6 and 9 were dramatically more active than the corresponding distomers.

The anti-proliferative activity of compound 2 was also assessed in matched TMZ susceptible (D54-S and U87-S) or resistant (D54-R and L187-R) cell lines (Hong Kong University, Dr Gilberto Leung). The data confirm that TMZ had reduced efficacy against TMZ-resistant subclones of both U87 and D54 compared to their respective TMZ-sensitive subclones. In contrast to TMZ, compound 2 and its eutomer demonstrated equipotent anti-proliferative activity against both the D54 and U87 GBM cell lines regardless of their TMZ resistance status. Two methodologies (SRB and MTT) were used to assess viability and both showed that compound 2 was equally effective at suppressing GBM cell viability regardless of TMZ resistance status. SRB tended to overestimate cytotoxicity compared to MTT. However, $IC_{50}$ values were below 0.36 µM regardless of methodology, cell line, and TMZ status when treated with compound 2. The $IC_{50}$ values of compound 2 therefore, are markedly lower than TMZ, even against TMZ sensitive subclones. Compound 2 eutomer was also equipotent against TMZ-resistant and sensitive subclones, but the anti-cancer efficacy was more potent for the active enantiomer than the racemate. $IC_{50}$ values were below 0.065 µM regardless of cell line and TMZ status (see Table 2).

TABLE 2

Cell viability of U87 and D54 TMZ resistant and sensitive subclones after treatment with TMZ, compound 2, or compound 2 eutomer*

| Compound | TMZ (SRB) | Compound 2 (SRB) | Compound 2 (MTT) | Compound 2 (+enantiomer) (MTT) |
|---|---|---|---|---|
| U87-sensitive | 609.12 | 0.106 | 0.329 | 0.037 |
| U87-resistant | 1828.51 | 0.128 | 0.358 | 0.041 |
| D54-sensitive | 630.99 | 0.090 | 0.271 | 0.065 |
| D54-resistant | 2755.76 | 0.092 | 0.215 | 0.065 |

*Cell viability ($IC_{50}$) at 72 hours post treatment was measured by SRB or MTT (as indicated). $IC_{50}$ in µM.

The anti-proliferative activity of the eutomer of compound 9 (the +enantiomer) was also assessed and found to be equipotent against TMZ-resistant and sensitive subclones of both U87 and D54 and similar to the eutomer of compound 2, $IC_{50}$ values were below 0.065 µM regardless of cell line and TMZ status.

The efficacy of the eutomers of compounds 9 and 36 was also tested against paediatric neuroblastoma cell lines. $IC_{50}$ values ranged from 0.020 µM to 0.088 µM for the compound 9 eutomer and from 0.243 µM to 0.698 µM for the compound 36 eutomer. (see Table 3). Two more paediatric neural cancers were assessed for sensitivity to the eutomer of compound 9. In vitro studies also showed low micromolar to sub-micromolar efficacy against a DIPG cell line, and nanomolar efficacy against medulloblastoma cell lines (D283L=0.097 µM; 547L=0.063 µM; and D425L=0.101 µM). Together with the previous studies using GBM cell lines and PDX cultures, these results suggest that compound 9 has considerable potency against a range of neural cancers including major childhood cancers.

TABLE 3

Cytotoxicity of compound 9 and 36 eutomers against neuroblastoma*

| Cell line | P53 status | nMYC status | Cpd 9 (+enantiomer) $IC_{50}$ (µm) | Cpd 36 (+enantiomer) $IC_{50}$ (µm) |
|---|---|---|---|---|
| CHLA-20 | wildtype | not amplified | 0.061 | 0.243 |
| CHP-134 | wildtype | amplified | 0.020 | 0.698 |
| CHLA-90 | mutant | not amplified | 0.088 | 0.336 |
| SK-N-Be(2) | mutant | amplified | 0.064 | 0.308 |

*Cell viability was assessed after 72 hours

The ability of compounds 1 to 14 to inhibit the proliferation of ovarian cancer stem cells was established from patient-derived explants. The laboratory of Dr Gil Mor (Yale University) have identified two types of epithelial ovarian cancer cells: Type I are chemoresistant, CD44+ve epithelial ovarian cancer (EOC) cells and Type II are chemosensitive CD44−ve EOC cells. Ovarian cancer stem cells were prepared as described previously (Alvero et al., 2009). Cell proliferation was assessed using the Incucyte Kinetic Imaging System. The cytotoxic effect of the compounds was assessed concurrently using the CellPlayer cytotoxicity assay using CellTox™ (Promega, Cat#: G8731). Monolayer cells were trypsinised and plated in 96-well plates. After 24 hrs, once the cells have attached, treatment was dispensed in RPMI with 10% FBS. Drug concentrations used were: 0.001, 0.01, 0.1, 1, and 10 µg/ml. An appropriate dilution of CellTox™ reagent (1:1000) was added to each well after adding the test compound. Culture plates were immediately placed in the Incucyte system and imaged every 2 hrs using the "Fluorescence and Phase contrast" option on the Incucyte equipment. Growth curves were calculated as a measure of cell confluence using an integrated confluence algorithm as a surrogate for cell number to determine proliferation rate. The area under the curve calculated from the plot of CsttTox Count/$mm^2$ over time was then used to calculate the $IC_{50}$. In duplicate experiments it was found that compound 2 was most potent at retarding the proliferation of ovarian cancer stem cells at concentrations between 0.01-0.1 µg/ml for OCSC-1 and OCSC-2. Compounds 6, 9 and 13 were also potent at inhibiting the proliferation of OCSC-2 cells at concentrations between 0.1 and 1 µg/ml (Table 4). Compound 2 also elicited a similar effect against F2 cells at log-fold higher concentrations (0.1-1 µg/ml). Where assessed, all other analogues exhibited anti-proliferative activity of 1-10 µg/ml (see Table 4).

TABLE 4

Anti-cancer effect of a series of compounds against ovarian cancer stem cells

| | $IC_{50}$ Range (µM) | | |
|---|---|---|---|
| Compound | OCSC1 | OCSC2 | F2 |
| 1 | 1-10 | 1-10 | NT |
| 2 | 0.1-0.01 | 0.1-0.01 | 0.1-1 |
| 3 | >10 | 1-10 | NT |
| 4 | 1-10 | 1-10 | NT |
| 5 | NT | 1-10 | NT |
| 6 | NT | 0.1-1 | NT |
| 7 | NT | >10 | NT |
| 8 | NT | 1-10 | NT |
| 9 | NT | 0.1-1 | NT |
| 10 | NT | 1-10 | NT |
| 11 | NT | 1-10 | NT |
| 12 | NT | >10 | NT |
| 13 | NT | 0.1-1 | NT |
| 14 | NT | >10 | NT |

NT = not tested

Figure 3:
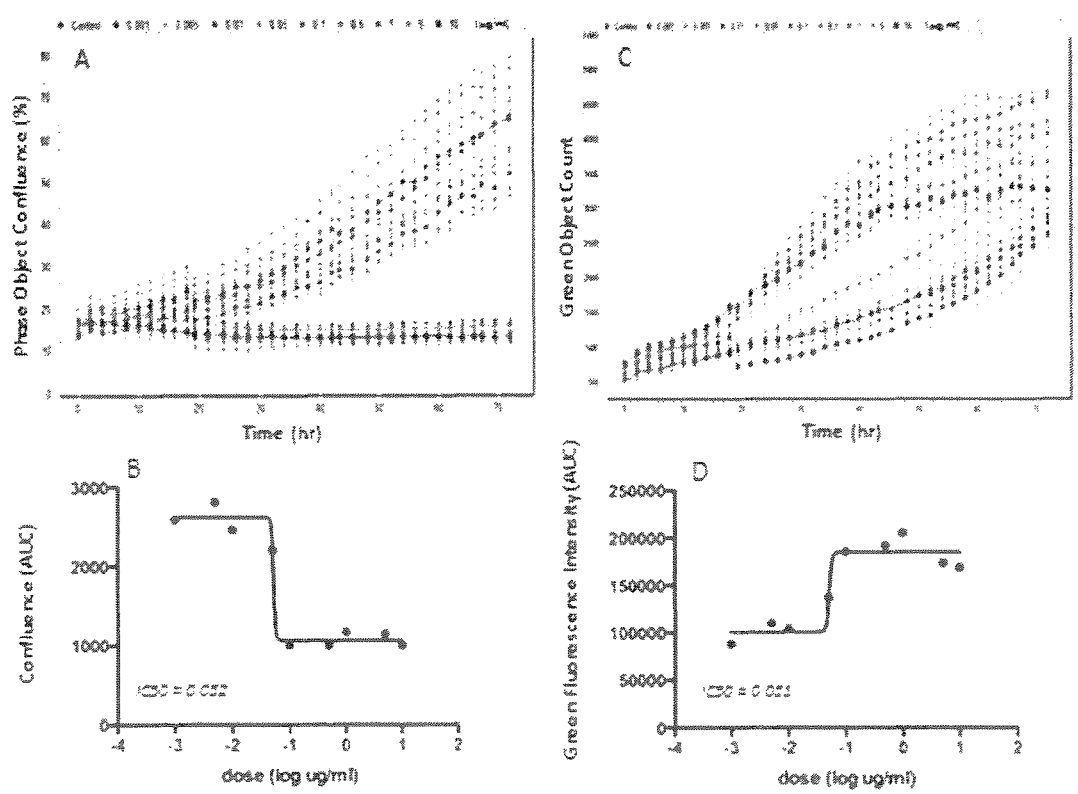
FIG. 3: Analysis of the efficacy of compound 2 against OCSC-2 cells using confluence (A, B), and cell damage (C, D) imaging. The $IC_{50}$ was calculated from plots of AUC for confluence and fluorescence intensity against time. $IC_{50}$ calculations were conducted after 72 hrs culture.
Figure 4:
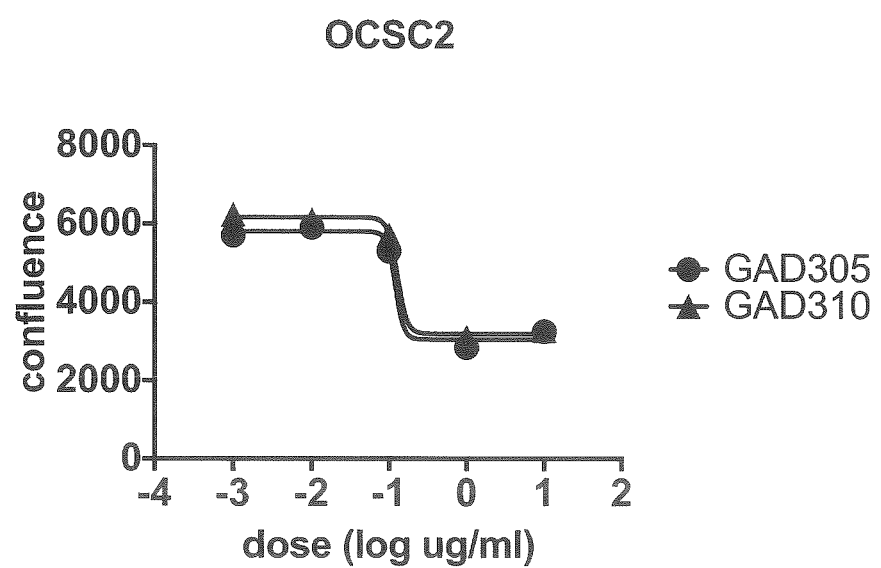
FIG. 4: Analysis of the efficacy of compound 2 against OCSC-2 cells using confluence. $IC_{50}$ calculations were conducted after 72 hrs culture. GAD 305 is compound 9 herein and GAD 310 is compound 13 herein.

Confirmatory studies using Incucyte confluence studies that employed a greater number of concentrations demonstrated that compound 2 had an $10_{50}$ of 0.052 µg/ml against OCSC2. This observation was further confirmed using Cytotox green, a dye reagent which exploits the compromised membrane integrity of a dead cell, with the reagent able to cross the membrane and bind to DNA thereby releasing a fluorescence signal that can be quantified. The $IC_{50}$ for compound 2 using CellTox green was 0.051 pg/ml. These data demonstrate that compound 2 is a highly active anti-cancer compound as assessed by two different methodologies. $IC_{50}$ values of 0.12 g/ml were also generated for compounds 9 and 13 (see FIGS. 3 and 4).

The ability of selected compounds to inhibit the proliferation of cancer cells representative of melanoma, non-small cell lung cancer, colorectal cancer, breast cancer (Estogen Receptor negative (ER−ve, TNBC-R−ve, Progesterone Receptor negative and negative for EGFR amplification), prostate cancer, liver cancer, ovarian cancer, pancreatic cancer and brain cancer was studied. A predetermined number of cells as calculated from cell growth assays for each of the cell lines employed were seeded into their respective culture mediums (using ATCC culture parameters—http://wwvv.atcc.org) and cultured for 24 hrs at 37° C. and 5% $CO_2$ in 96-well culture plates. Once attached, each cell line was then exposed to various concentrations of each respective analogue (30, 3, 0.3 and 0.03 μM), cultured for a further 72 hrs and exposed to cell-titre luminescent reagent (100μ/well) for a further 30 mins). Luminescence was captured using an EnVision multilabel reader and the data for each analogue concentration compared against control. Semi-log plots of Percent of Control versus concentration were prepared and IC$_{50}$ determined using linear regression analysis. The data are presented in Tables 5 and 6. In Table 6, compounds Comp 1, Comp 2 and Comp 3 are comparative compounds having the following structures:

Comp1

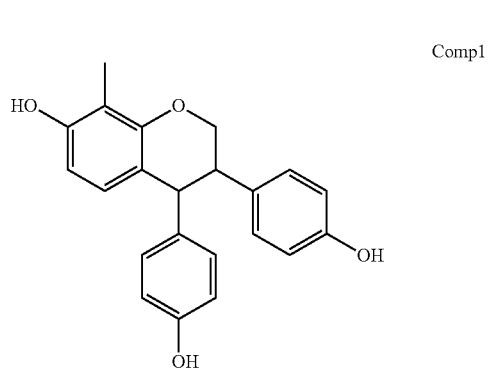

-continued

Comp2

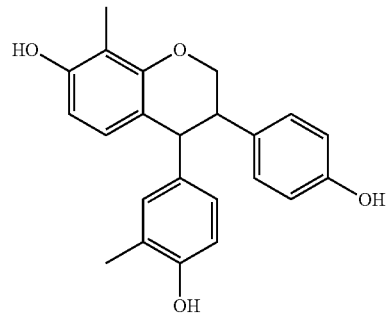

Comp3

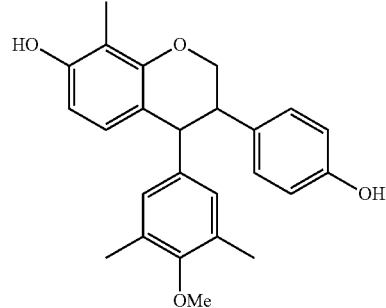

TABLE 5

Assessment of a series of compounds for their ability to retard the proliferation of a range of somatic cancer cells

| | | | | | | Breast | Lung | |
| | | | Prostate | | | MDA-MB- | (NSCLC) | Liver |
| | Colorectal | Melanoma | | | | | | |
| Compound | HT-29 | SK-Mel-28 | PC3 | DU145 | MCF-7 | 231 | A549 | HepG2 |
|---|---|---|---|---|---|---|---|---|
| 1 | 11 | >30 | >30 | >30 | >30 | 13.7 | >30 | >30 |
| 2 | 8.2 | 1.4 | 1.49 | 0.08 | 13.6 | 0.8 | 0.04 | 1.9 |
| 3 | 7.5 | >30 | >30 | 15.1 | 26.7 | 7.5 | 11.8 | >30 |
| 4 | 4.1 | >30 | >30 | 4.5 | >30 | 9.9 | 6.9 | >30 |
| 5 | 6.6 | >30 | >30 | >30 | >30 | 21.8 | 8.4 | >30 |
| 6 | 8.4 | >30 | 0.5 | 0.8 | >30 | 1.7 | 0.7 | 2 |
| 7 | >30 | >30 | >30 | >30 | >30 | >30 | >30 | >30 |
| 8 | 4.3 | >30 | 27 | 9.4 | >30 | >30 | 25.3 | >30 |
| 9 | 6.5 | 2.7 | 0.12 | 0.13 | >30 | 0.13 | 0.13 | 3.7 |
| 10 | 8.4 | >30 | 6.2 | 25.2 | >30 | 29.9 | 8.3 | 26.9 |
| 11 | 5 | >30 | 1.4 | 3.1 | >30 | 3.4 | 9.6 | 5.6 |
| 12 | >30 | >30 | >30 | >30 | >30 | >30 | >30 | >30 |
| 13 | 11.1 | >30 | 0.8 | 1.5 | >30 | 3 | 2.3 | 9.6 |
| 14 | >30 | >30 | >30 | >30 | >30 | >30 | >30 | >30 |
| 16 | 2.65 | 16.14 | 2.22 | 2.78 | 5.6 | 9.80 | 5.45 | 5.29 |
| 18 | 12.70 | 6.43 | 2.12 | 1.59 | 6.2 | 7.28 | 5.54 | 1.14 |
| 19 | 2.34 | 2.30 | 0.34 | 0.21 | 0.3 | 8.62 | 4.84 | 0.32 |
| 20 | 3.25 | 0.96 | 0.85 | 0.26 | 1.0 | 8.5 | 4.21 | 0.19 |
| 21 | 3.02 | 0.7 | 0.42 | 0.64 | 0.6 | 5.67 | 2.66 | 0.35 |
| 22 | 2.42 | 1.22 | 0.62 | 0.45 | 1.6 | 12.6 | 8.87 | 0.67 |
| 24 | >30 | >30 | 0.2 | 0.3 | >30 | 4.4 | 2.06 | >30 |
| 32 | 3.56 | 2.06 | 1.42 | 0.95 | 2.2 | 25.29 | 11.77 | 1.21 |
| 33 | 2.38 | 0.43 | 0.34 | 0.39 | 0.5 | 5.29 | 3.71 | 0.1 |
| 34 | 2.07 | 1.38 | 1.07 | 0.63 | 1.5 | 3.77 | 1.7 | 0.47 |
| 35 | 5.79 | 2.37 | 1.03 | 0.77 | 4.2 | 9.89 | 4.25 | 1.06 |
| 36 | NT | 0.16 | 0.18 | NT | NT | 0.2 | 0.24 | NT |
| 37 | NT | 0.21 | 0.53 | 0.44 | NT | 0.92 | 0.4 | NT |
| 38 | NT | >30 | 1.40 | 5.51 | NT | 23.12 | 2.60 | NT |
| 39 | NT | 0.52 | 0.73 | 0.49 | NT | 1.43 | 0.8 | NT |
| 40 | NT | >30 | 1.31 | 3.02 | NT | 14.11 | 1.91 | NT |

NT = Not tested

TABLE 6

Assessment of a series of compounds for their ability to retard the proliferation of a range of somatic cancer cells

| | IC$_{50}$ (µM) | | | | | |
|---|---|---|---|---|---|---|
| | | Brain | | Ovarian | | |
| Compound | Pancreatic MiaPaCa-2 | U87-MG | A172 | OVCAR-3 | A2780 | SK-OV-3 |
| 2 | 0.05 | 0.05 | 0.127 | 0.063 | 0.06 | 0.106 |
| 6 | NT | 0.478 | 0.193 | 0.063 | NT | 0.193 |
| 9 | 0.06 | 0.05 | 0.16 | 0.058 | 0.09 | 0.142 |
| 13 | NT | 0.513 | 0.388 | 0.171 | NT | 0.621 |
| 36 | 0.17 | 0.22 | NT | NT | 0.14 | NT |
| 37 | 0.52 | 0.38 | NT | NT | 0.32 | NT |
| 39 | 0.58 | 0.49 | NT | NT | 0.61 | NT |
| Comp1 | 0.89 | 0.25 | NT | NT | 0.21 | NT |
| Comp2 | 0.59 | 0.23 | NT | NT | 0.37 | NT |
| Comp3 | >3 | >3 | NT | NT | >3 | NT |

NT = Not tested

The data demonstrate that compound 2 exhibited potent anti-proliferative activity (IC$_{50}$=<1 µM) against cell lines representative of NSCLC (A549), TNBC (MDA-MB-231) and prostate cancer (DU-145). Compound 2 was moderately active against liver cancer cells (HepG2) (IC50=1.9 µM).

Compounds 6 and 9 also exhibit potent activity (IC$_{50}$=<1 µM) against NSCLC (A549) and both prostate cancer cell lines (PC3 and DU-145), unlike compound 2 which was only active against DU-145. Compounds 6 and 9 were also moderately active against MDA-MB-231 (IC$_{50}$<2 µM) and HepG2 (IC$_{50}$<4 µM).

Figure 5:
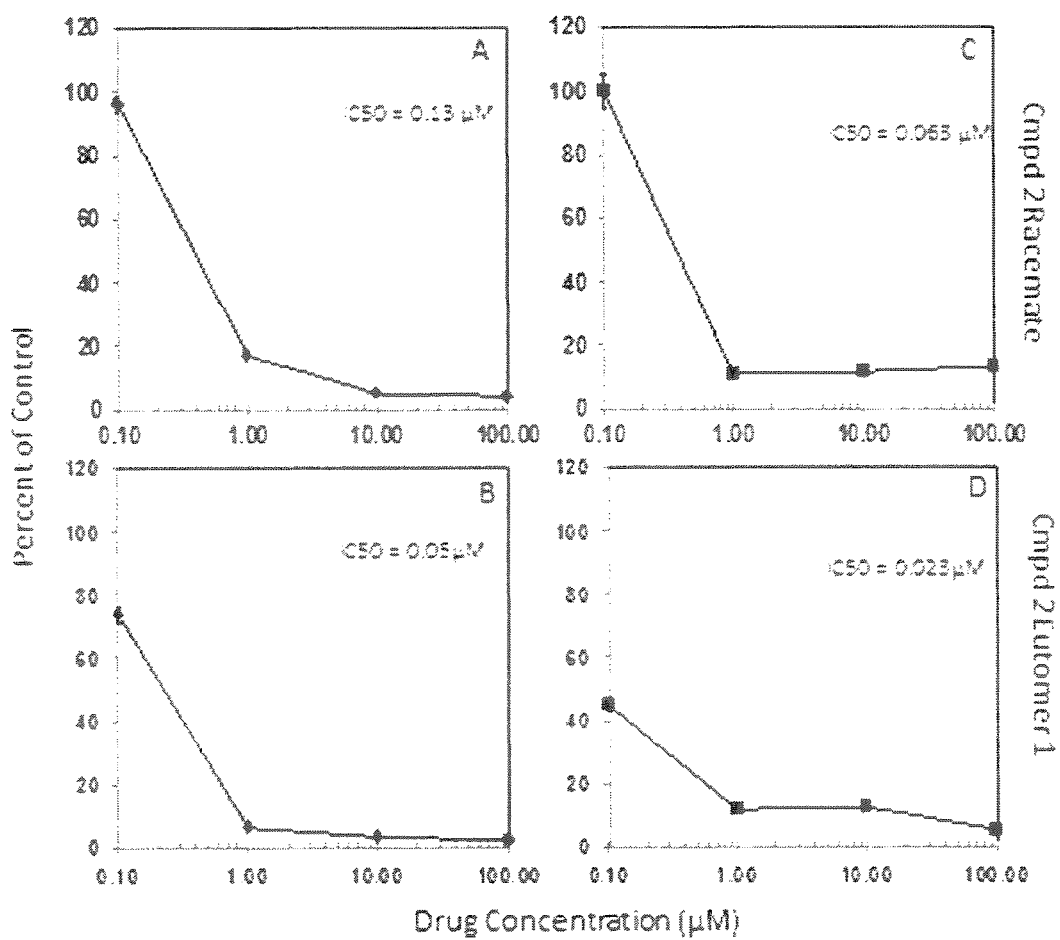
FIG. 5: Assessment of the racemate of compound 2 (A, C) and its eutomer (B, D) against the A172 (Glioma) (A and B) and OVCAR-3 (ovarian cancer) (C and D) cell lines.

Using the same methodology the racemate of compound 2 and its enantiomers were assessed against the A172 glioblastoma and OVCAR-3 ovarian cancer cell lines. As was observed in the GBM explant study above, the eutomer of compound 2 was at least 2-fold more active against both cell lines when compared with the racemate (see FIG. 5). The distomer was >5 fold less active compared with the racemate (not shown).

Given the concept that residual cancer progenitor cells within the tumour post-treatment are responsible for tumour relapse, a critical therapeutic strategy to prolong survival is to eradicate those tumour progenitor cells driving relapse. In vitro studies were conducted to determine whether compound 2 was able to inhibit OCSC proliferation once drug pressure was removed. OCSC-2 cells were treated with 0.1, 1 and 10 µg/ml of compound 2 for 24 hrs, washed with culture medium and allowed to recover for a further 50 hrs under standard incubation conditions. Culture plates were immediately placed in the Incucyte system and imaged every 2 hrs. Growth curves were calculated as a measure of cell confluence using an integrated confluence algorithm as a surrogate for cell number to determine proliferation rate.

Figure 6:
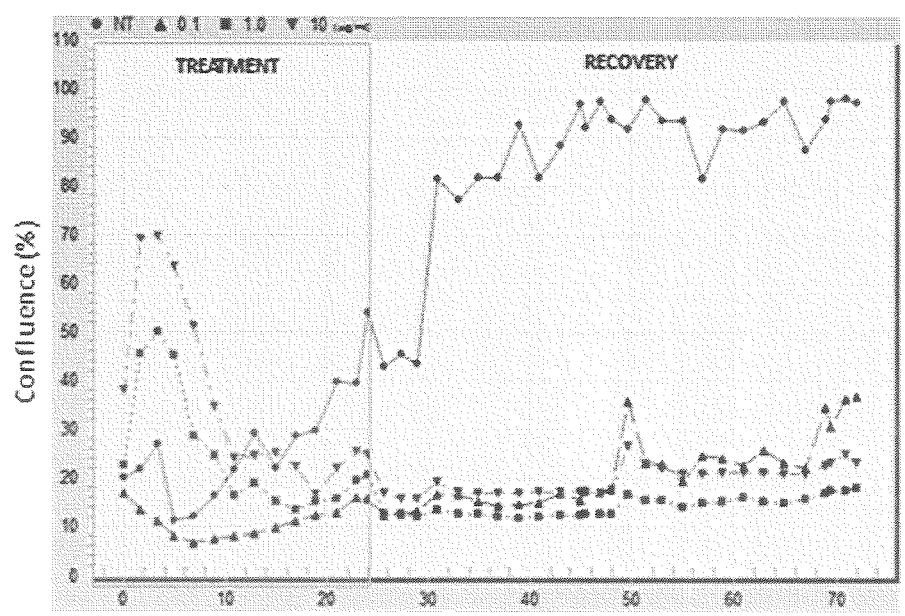
FIG. 6: Ability of compound 2 to retard the proliferation of ovarian cancer stem cells.
Figure 7:
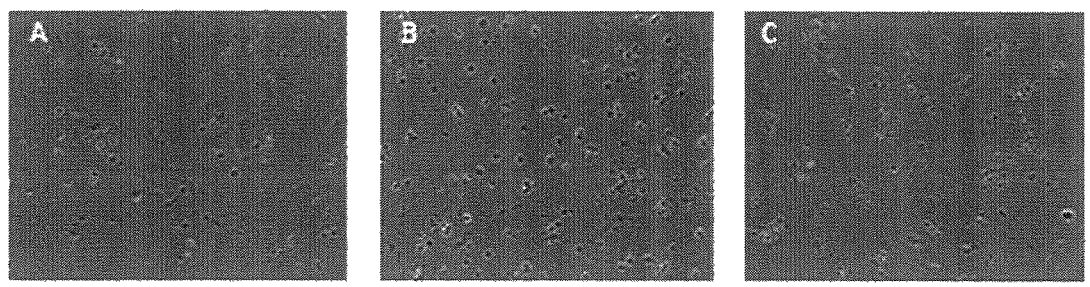
FIG. 7: Microscopic evaluation of OCSC2 cells treated with compound 2 at 1 µg/ml over 24 (B) and 48 hrs (C) compared with control, 72 hrs (A).

In contrast to OCSC-2 cells treated with vehicle, those cells that were pre-treated with compound 2 for 24 hrs failed to enter logarithmic growth after an additional 48 hrs of culture in medium without drug (see FIG. 6). Morphologically these cells appeared rounded and had apoptotic bodies suggesting that the cells were no longer viable from 24 hrs exposure (see FIG. 7).

Example 3

Cell Studies

Figure 8:
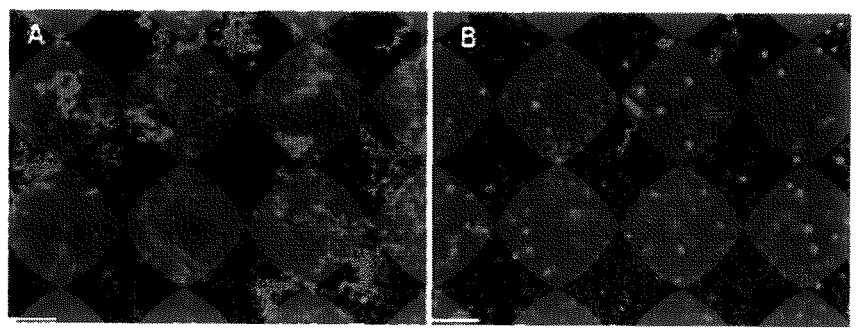
FIG. 8: Fluorescent microscopy of GFP-labeled OCSC-2 stem cells and mCherry-labeled OCC2 co-cultures treated with compound 2 at 1 µg/ml over 48 hrs (B) compared with control (A).

GFP-labeled OCSC2 and mCherry-labeled OCC2 cells were established by infecting cells with lentivirus expressing the fluorescent proteins (Craveiro et al. 2013). Co-cultures of GFP+ OCSC2 and mCherry+ OCC2 were treated with 1 µg/ml of compound 2 for 48 hrs and allowed to recover for another 72 hrs. Fluorescence was determined by fluorescence microscopy. Compound 2 markedly reduced GFP-labeled OCSC2 stem cell numbers and caused mCherry-labeled OCC2 cells to round up and lift off the culture surface (see FIG. 8). These data indicate that compound 2 disrupts the proliferation of both ovarian cancer stem cells and ovarian cancer somatic cells.

Figure 9:
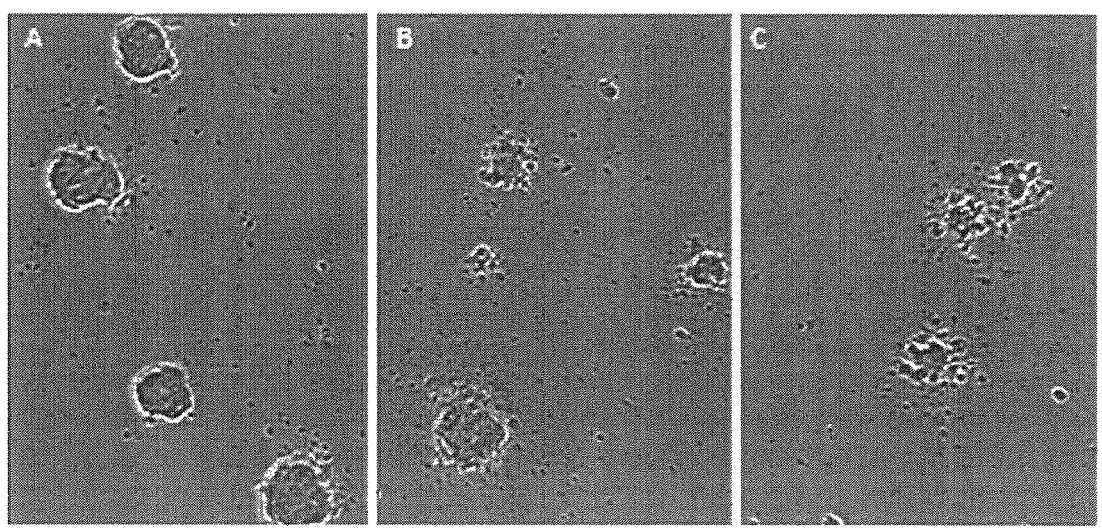
FIG. 9: Compound 2 destroys ovarian cancer stem cell spheroids. OCSC-2 spheroids were established using standard methodology and exposed to increasing concentration of compound 2 over 24 hrs. A, Control; B. 0.1 µg/ml-24 hr; C, 1 µg/ml-24 hr Spheroid structure was assessed by microscopy.

Ovarian cancer stem cell spheroids were obtained from cultures grown under special conditions that selected for cells with self-renewing potential (Alvero et al., 2009). Briefly, CD44+ cells were incubated in a suspension system consisting of a glass tube in continuous rotation to prevent adherence These cells formed clusters in 48 hrs and compact spheroids in 4 days. Spheroids were then exposed to 0.1 and 1 µg/ml of compound 2 and examined microscopically after 24 hrs. After 24 hrs exposure to compound 2 at 0.1 µg/ml the ovarian cancer spheroids infrastructure had started to disintegrate. At 1 µg/ml of compound 2 the spheroid structure was almost totally destroyed. These data demonstrate that compound 2 is able to penetrate the spheroid and destroy its infrastructure (see FIG. 9) and is suggestive that the compound should be able to enter the tumour micro-environment.

References

Craveiro, V. Yang-Hartwich, Y., Holmberg, J. C., Sumi, N. J., Pizzonia, J Grffin, B., Gill S. K., Sliasi, D-A., Azodi, M., Rutherford, T., Alvero, A, B., Mor, G. (2013). "Phenotypic modifications in ovarian cancer stem cells following Paclitaxel treatment" *Cancer Medicine,* 2(6), 751-762.

Alvero A . B., Chen R. Fu H H. Montagna M., Schwartz P. E., Rutherford T., Silasi D. A., Steffensen K. D., Waldstrom M., Visintin I., Mor G. (2009) "Molecular phenotyping of human ovarian cancer stem cells unravels the mechanisms for repair and chemoresistance" *Cell Cycle.* 2009 Jan. 1;8(1):158-66.

Example 4

Pharmacokinetic Testing

A study of the pharmacokinetic behavior of compounds 2, 6, 9, 13 was performed. The results demonstarted that the compounds can be delivered and achieve plasma concentrations with the proposed pharmaceutic window of efficacy.

Figure 10:
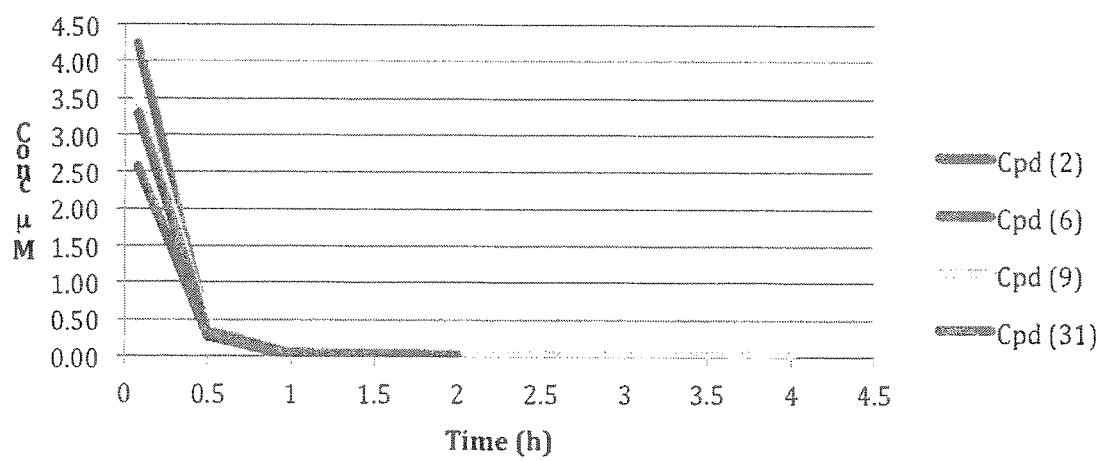
FIG. 10: PK profile of compounds 2, 6, 9 and 13 (which is labelled as 31) at 1 mg/kg delivered in 30% Captisol® formulation.

The study comprised Phase 1, a preformulation study ensuring all compounds were soluble in 30% Captisol® solution and formed a homogenous mixture suitable for i.v delivery. A number of LC-MS methods were developed and partially validated to ensure each analyte could be quantified from the plasma matrix and that there was no interference between any of the analytes. Phase 2 comprised the in-life study whereby Sprague-Dawley rats were acclimatised for three days prior to being injected in the tail vein with a cassette dose of four compounds, each at a final concentration of 1 mg/Kg. A total of three rats were used in the study with blood sampling with anticoagulant tubes at 5 mins, 30 mins, 1 hr, 2 hrs, 4 hrs, 6 hrs and 8 hrs. The third phase of the study was the bioanalysis of the analytes. The blood samples were centrifuged at 1200 rpm for 10 mins at 4° C. After the RBCs and the plasma were separated, the plasma was stored at −80 ° C. until processed and injected into the LC-MS. Samples from individual rats were treated as individual samples with the PK profile generated from the mean of the data from the three rats. The results are shown in FIG. 10.

Example 5

In Vivo Efficacy

Figure 11:
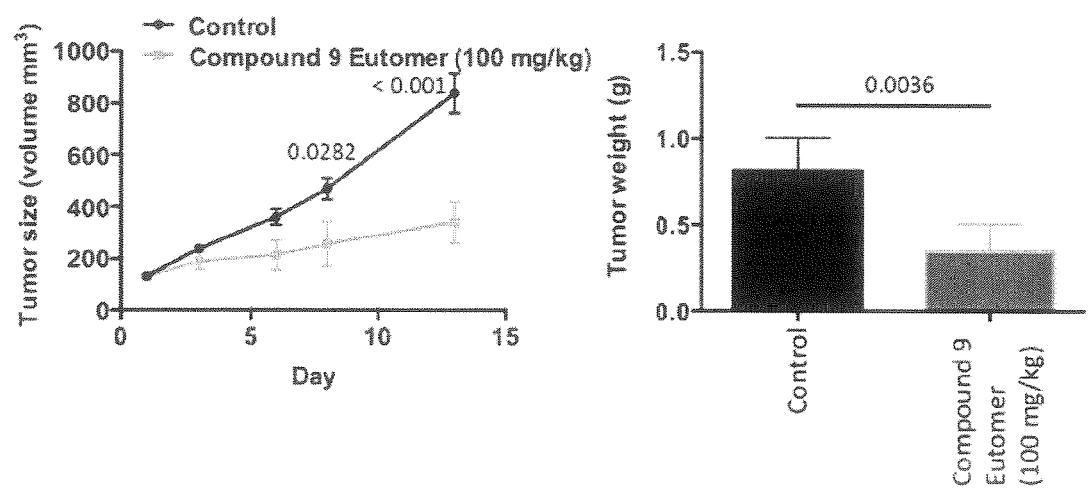
FIG. 11: In vivo efficacy of compound 9 eutomer against a flank model of GBM (U87MG). Using the U87 flank model previously described, mice were divided into two groups, a treatment group (compound 9 eutomer) formulated in a cocoa-butter suppository base and dosed daily at 100 mg/kg —and a suppository control group (n=10 for control and n=4 for compound 9). Mice were observed daily, weighed every third day and euthanized after 12 days of treatment. On termination of the treatment, tumours were excised and weighed. Compound 9 was administered daily at 100 mg/kg in a suppository formulation while control animals were dosed with the suppository formulation only. Tumour growth curves (mean ±SEM) for the extent of treatment (12 days) were significantly different (P values shown). Tumour weight (median and quartiles) was also significantly reduced (P values shown above graph).

Using the U87 flank model model previously described, suppository delivery of the eutomer of compound 9 at 100 mg/kg daily elicited a strong anti-tumour effect. The results are shown in FIG. 11. Two-way ANOVA with Sidak's correction for multiple comparisons indicated that tumour size was significantly smaller by just 7 days post-treatment initiation and this continued through to day 12 (the final time point assessed). The rate of tumour growth was also significantly reduced by the eutomer of compound 9. Tumour weight at end point was significantly reduced by the eutomer of compound 9 compared to Captisol® control (unpaired t test, P=0.0036). Final mouse eights in the treatment and control groups were not significantly different, however 3 mice in the treatment group of an original 7 died (all animals that died were within the lower quartile of animal weight range). These mice also showed significant reduction in tumour growth, although, for consistency, the data from those animals has been removed form all data presented and from statistical analysis. As with the previous dosing schedule, no overt clinical signs of toxicity (i.e. piloerection, morbidity, diarrhea) were noted. Histopathological analysis is ongoing to identify the cause of death. Blood counts were normal.

Example 6

In Vivo Efficacy

The ovarian cancer animal model used to assess the in vivo efficacy of compound 2 consists of intraperitoneal injection of $7 \times 10^6$ mCherry-CD44+ ovarian cancer stem cells into athymic mice. In this model, tumor formation replicates the morphology of human ovarian cancer, giving rise to disseminated tumors comprising both CD44+ and CD44− OCC, confirming that the injected cancer stem cells can form heterogeneous tumors. In this rodent model, tumor progression is characterized by disseminated carcinomatosis where tumors are found in the ovaries, mesentery, peritoneum, diaphragm, liver, pancreas, and spleen. The model also mimics the clinical profile for ovarian cancer and is characterized by an initial partial response to paclitaxel or cisplatin, which is then followed by recurrence and resistance to the original therapy. Tumor progression is monitored by life imaging using a Bruker fluorescence/X-Ray imaging system Vivo FX System (Bruker Corp., Billerica, Mass.) (Craveiro et al. 2013).

Figure 12:
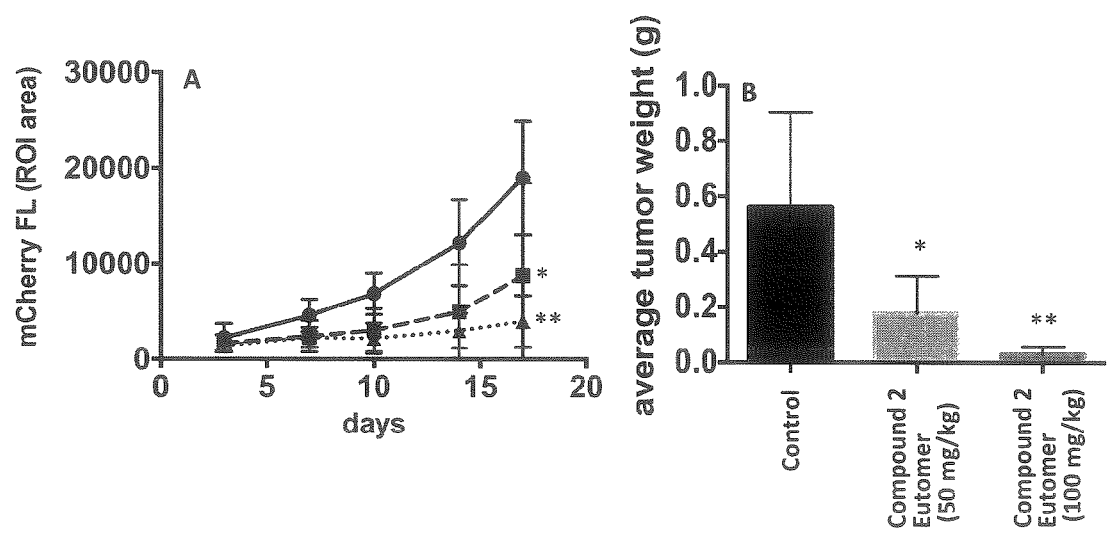
FIG. 12: in vivo efficacy of compound 2 eutomer in an ovarian cancer animal model. Animals were inoculated with OCSC1-F2 m-Cherry cells and then dosed on day 4 post-inoculation with Captisol® formulated compound 2 eutomer using two different regimens (100 mg/kg, i.p., qd, 50 mg/kg, i.p.) and efficacy compared with control. A, Average tumor fluorescence intensity (tumors were visualized every third day using a Vivo FX Imaging system, ROI) ●, Captisol® control; ■, compound 2 eutomer (50 mg/kg i.p. daily); ▲, compound 2 eutomer (100 mg/kg i.p. daily); B. Average terminal tumor burden was assessed by removing and weighing all tumors from both the control and Captisol® formulated compound 2 eutomer treated animals, *, p<0.02; **, p<0.0001; vs respective controls.

Compared to control animals treated with 20% Captisol®, the eutomer of Compound 2 dosed on a daily i.p. schedule formulated in a cyclodextrin elicited a significant, dose-dependent reduction in the rate of tumor proliferation (FIG. 12A) and terminal tumor burden (FIG. 12B). We observed a concentration-dependent response where animals dosed with compound 2 at 50 mg/kg and 100 mg/kg had a 65% and >80% reduction in tumor burden respectively compared with control.

REFERENCE

Craveiro, V., Yang-Hartwich, Y., Holmberg, J. C., Sumi, N. J., Pizzonia, J., Grffin, B., Gill., S. K., Silasi, D-A., Azodi, M., Rutherford, T., Alvero, A, B., Mor, G. (2013). "Phenotypic modifications in ovarian cancer stem cells following Paclitaxel treatment" *Cancer Medicine,* 2(6), 751-762.

The citation of any reference herein should not be construed as an admission that such reference is available as prior art to the present application. Further, the reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endevour to which this specification relates.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps, features, compositions and compounds.

The invention claimed is:

1. A compound selected from the group consisting of:

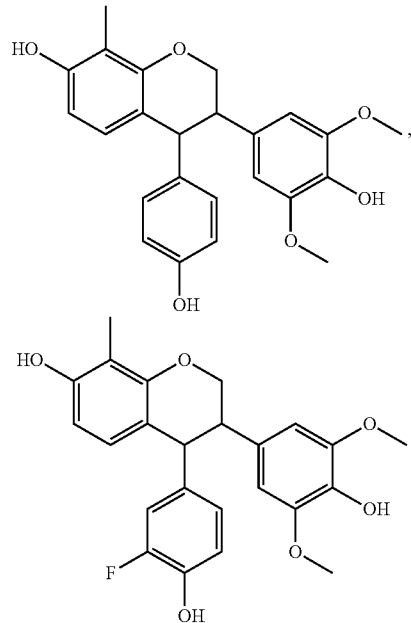

and pharmaceutically acceptable salts thereof.

2. A pharmaceutical composition comprising the compound according to claim 1 together with a pharmaceutically acceptable carrier, diluent or excipient.

3. A method for the treatment of cancer in a subject in need thereof, the method comprising administration to the subject of a therapeutically effective amount of the compound according to claim 1.

4. The method of claim 3, wherein the cancer is a cancer that has recurred.

5. The method of claim 3, wherein the cancer is resistant to one or more chemotherapeutic agents.

6. The method of claim 3, wherein the cancer is selected from the group consisting of: pancreatic cancer, colorectal cancer, melanoma, prostate cancer, brain cancer (including paediatric and adult), ovarian cancer, breast cancer, lung cancer, liver cancer, uterine cancer, neuroblastoma, mesothelioma, malignant ascites and peritoneal cancer.

7. A method for reducing incidences of, or risk of, cancer recurrence in a subject deemed to be at risk of cancer recurrence, the method comprising administration to the subject of an effective amount of the compound according to claim 1.

8. The method of claim 7, wherein the subject deemed to be at risk of cancer recurrence is a subject who is in cancer remission.

9. The method of claim 8, wherein the subject is in remission from ovarian cancer or brain cancer.

10. The method of claim 6, wherein the cancer is ovarian cancer or brain cancer.

11. The method of claim 6, wherein the cancer is brain cancer.

12. The method of claim 11, wherein the brain cancer is glioma.

* * * * *